US011263405B2

United States Patent
Gnanasambandam et al.

(10) Patent No.: US 11,263,405 B2
(45) Date of Patent: Mar. 1, 2022

(54) SYSTEM AND METHOD FOR ANSWERING NATURAL LANGUAGE QUESTIONS POSED BY A USER

(71) Applicant: HEALTHPOINTE SOLUTIONS, INC., Austin, TX (US)

(72) Inventors: Nathan Gnanasambandam, Irvine, CA (US); Mark Henry Anderson, Newport Coast, CA (US)

(73) Assignee: HEALTHPOINTE SOLUTIONS, INC., Austin, TX (US)

( * ) Notice: Subject to any disclaimer, the term of this patent is extended or adjusted under 35 U.S.C. 154(b) by 383 days.

(21) Appl. No.: 16/593,491

(22) Filed: Oct. 4, 2019

(65) Prior Publication Data
US 2020/0117857 A1 Apr. 16, 2020

Related U.S. Application Data

(60) Provisional application No. 62/801,777, filed on Feb. 6, 2019, provisional application No. 62/743,985, filed on Oct. 10, 2018.

(51) Int. Cl.
*G06F 17/00* (2019.01)
*G06F 40/30* (2020.01)
(Continued)

(52) U.S. Cl.
CPC ............ *G06F 40/30* (2020.01); *G06F 40/295* (2020.01); *G06N 5/04* (2013.01); *G16H 10/20* (2018.01); *G16H 50/20* (2018.01); *G16H 70/00* (2018.01)

(58) Field of Classification Search
None
See application file for complete search history.

(56) References Cited

U.S. PATENT DOCUMENTS 5,839,438 A 11/1998 Graettinger et al.
8,271,415 B2 9/2012 Iliff
(Continued)

FOREIGN PATENT DOCUMENTS

JP 2001273362 A 10/2001

OTHER PUBLICATIONS

International Searching Authority, Search Report and Written Opinion for International Application No. PCT/US19/55615, dated Jan. 8, 2020; 10 Pages.
(Continued)

*Primary Examiner* — Satwant K Singh
(74) *Attorney, Agent, or Firm* — Dickinson Wright, PLLC; Stephen A. Mason; Jonathan H. Harder

(57) ABSTRACT

A computer-implemented method for answering natural language medical information questions posed by a user of a medical conversational interface of a cognitive artificial intelligence system, the method comprising: receiving from a medical conversational user interface a user-generated natural language medical information query at an artificial intelligence-based medical conversation cognitive agent; extracting a medical question from the query; compiling a medical conversation language sample; extracting internal medical concepts and medical data from the sample, where the internal medical concepts include descriptions of medical attributes of the medical data entities; inferring a therapeutic intent of the user; generating a therapeutic paradigm logical framework for interpreting of the medical question, wherein logical framework comprises a catalog of medical logical progression paths from the medical question to respective therapeutic answers, each of the logical progression paths includes one or more medical logical linkages from the medical question to a therapeutic path-specific answer, and the medical logical linkages include the internal
(Continued)

medical concepts and external therapeutic paradigm concepts derived from a store of medical subject matter ontology data; selecting a likely medical information path based upon the therapeutic intent of the user; and answering the medical question.

27 Claims, 26 Drawing Sheets

(51) Int. Cl.
| | |
|---|---|
| *G16H 10/20* | (2018.01) |
| *G06F 40/295* | (2020.01) |
| *G16H 50/20* | (2018.01) |
| *G06N 5/04* | (2006.01) |
| *G16H 70/00* | (2018.01) |

(56) References Cited

U.S. PATENT DOCUMENTS

| | | |
|---|---|---|
| 8,337,409 B2 | 12/2012 | Iliff |
| 8,579,812 B2 | 11/2013 | Causevic |
| 8,666,926 B1 | 3/2014 | Nease et al. |
| 9,536,052 B2 | 1/2017 | Amarasingham et al. |
| 10,431,337 B2 * | 10/2019 | Allen ..................... G16H 10/60 |
| 10,431,338 B2 * | 10/2019 | Allen ..................... G16H 70/20 |
| 10,541,053 B2 * | 1/2020 | Sheffer ................. G16H 10/60 |
| 2009/0083231 A1 | 3/2009 | Eberholst et al. |
| 2010/0278420 A1 | 11/2010 | Shet et al. |
| 2012/0029361 A1 | 2/2012 | Addison et al. |
| 2012/0047105 A1 | 2/2012 | Saigal et al. |
| 2012/0129139 A1 | 3/2012 | Partovi |
| 2012/0158633 A1 | 6/2012 | Eder |
| 2012/0239560 A1 | 9/2012 | Pourfallah et al. |
| 2014/0074454 A1 | 3/2014 | Brown et al. |
| 2014/0188511 A1 | 7/2014 | Gaylis et al. |
| 2015/0019248 A1 | 1/2015 | Anand et al. |
| 2015/0193583 A1 | 7/2015 | McNair et al. |
| 2015/0332283 A1 | 11/2015 | Witchey |
| 2016/0171119 A1 * | 6/2016 | Bufe ..................... G06F 3/0484 715/746 |
| 2016/0321406 A1 | 11/2016 | Timmerman et al. |
| 2016/0364534 A1 | 12/2016 | Naji |
| 2017/0076053 A1 | 3/2017 | Sysko et al. |
| 2017/0091397 A1 | 3/2017 | Shah |
| 2017/0132393 A1 | 5/2017 | Natarajan et al. |
| 2018/0025127 A1 * | 1/2018 | Bagchi ................. G06F 16/2455 705/2 |
| 2018/0032514 A1 * | 2/2018 | Venkataraman ........ G06F 16/48 |
| 2018/0089383 A1 * | 3/2018 | Allen ..................... G16H 50/20 |
| 2018/0285879 A1 | 10/2018 | Gadnis et al. |
| 2018/0336317 A1 * | 11/2018 | Carbonell .............. G06Q 20/29 |
| 2019/0252074 A1 | 8/2019 | Datla et al. |
| 2019/0392547 A1 * | 12/2019 | Katouzian ............ G06N 3/0445 |

OTHER PUBLICATIONS

International Searching Authority, Search Report and Written Opinion for International Application No. PCT/US19/55614, dated Jan. 8, 2020; 10 Pages.
International Searching Authority, Search Report and Written Opinion for International Application No. PCT/US19/55617, dated Jan. 8, 2020; 10 Pages.
International Searching Authority, Search Report and Written Opinion for International Application No. PCT/USig/556ig, Mailed on Jan. 10, 2020; 15 Pages.
International Searching Authority, Search Report and Written Opinion for PCT/US20/33284, dated Jul. 29, 2020; 9 pages.
International Searching Authority, Search Report and Written Opinion for PCT Application PCT/US20/33634, dated Aug. 6, 2020; 9 pages.
International Searching Authority, Search Report and Written Opinion for PCT/US20/47477, dated Nov. 20, 2020; 9 pages.
International Searching Authority, International Search Report and Written Opinion for International Application No. PCT/US20/47480, dated Nov. 23, 2020; 10 pages.
International Searching Authority, International Search Report and Written Opinion for International Application No. PCT/US20/47482, dated Nov. 23, 2020; 10 pages.

* cited by examiner

FIG. 8C

SYSTEM AND METHOD FOR ANSWERING NATURAL LANGUAGE QUESTIONS POSED BY A USER

CROSS-REFERENCE TO RELATED APPLICATIONS

This application claims the benefit of U.S. Provisional Application No. 62/743,985 filed Oct. 10, 2018 titled "Population Management for Health," and U.S. Provisional Application No. 62/801,777 filed Feb. 6, 2019 titled "System and Method For Answering Natural Language Questions Posed By A User." Both provisional applications are incorporated by reference herein as if reproduced in full below.

BACKGROUND

Population health management entails aggregating patient data across multiple health information technology resources, analyzing the data with reference to a single patient, and generating actionable items through which care providers can improve both clinical and financial outcomes. A population health management service seeks to improve the health outcomes of a group by improving clinical outcomes while lowering costs.

SUMMARY

A system and method for answering natural language questions posed by a user involves receiving an information query, extracting a question from the information query, compiling a conversation language sample, extracting concepts and data entries, inferring user intent, generating a framework paradigm, selecting a likely information path, and answering the question.

Representative embodiments set forth herein disclosure various techniques for enabling a system and method for answering natural language questions posed by a user.

A According to some embodiments, a computer-implemented method for answering natural language medical information questions posed by a user of a medical conversational interface of a cognitive artificial intelligence system is disclosed. In some embodiments, the method includes receiving from a medical conversational user interface a user-generated natural language medical information query at an artificial intelligence-based medical conversation cognitive agent. In some embodiments, the method further includes extracting from the user-generated natural language medical information query a medical question from a user of the medical conversational user interface. In some embodiments, the method further includes compiling a medical conversation language sample. The medical conversation language sample can include items of health-information-related-text derived from a health-related conversation between the artificial intelligence-based medical conversation cognitive agent and the user. In some embodiments, the method further includes extracting from the medical conversation language sample internal medical concepts and medical data entities present within the medical conversation language sample. The internal medical concepts can include descriptions of medical attributes of the medical data entities. In some embodiments, the method further includes inferring a therapeutic intent of the user from the internal medical concepts and the medical data entities. In some embodiments, the method further includes generating a therapeutic paradigm logical framework for interpreting of the medical question. The therapeutic paradigm logical framework can include a catalog of medical logical progression paths from the medical question to respective therapeutic answers. Each of the medical logical progression paths can include one or more medical logical linkages from the medical question to a therapeutic path-specific answer. The medical logical linkages can include the internal medical concepts and external therapeutic paradigm concepts derived from a store of medical subject matter ontology data. In some embodiments, the method further involves selecting a likely medical information path from among the medical logical progression paths to a likely path-dependent medical information answer based upon the therapeutic intent of the user. In some embodiments, the method further involves answering the medical question by following the likely medical information path to the likely path-dependent medical information answer.

According to some embodiments, a cognitive intelligence platform for answering natural language questions posed by a user of a conversational interface of an artificial intelligence system is disclosed. In some embodiments, the cognitive intelligence platform includes a cognitive agent configured for receiving from a user interface a user-generated natural language query wherein the cognitive agent is an artificial intelligence-based conversation agent. In some embodiments, the cognitive intelligence platform further includes a knowledge cloud containing a store of subject matter ontology data. In some embodiments, the cognitive intelligence platform further includes a critical thinking engine. In some embodiments, the critical thinking engine is configured for extracting from the user-generated natural language query a question from a user of the user interface. In some embodiments, the critical thinking engine is further configured for compiling a language sample. The language sample can include items of text derived from a conversation between the artificial intelligence-based conversation agent and the user. In some embodiments, the critical thinking engine is further configured for extracting from the language sample internal concepts and entities present within the language sample, wherein the internal concepts can include descriptions of attributes of the entities. In some embodiments, the critical thinking engine is further configured for inferring an intent of the user from the internal concepts and the entities. In some embodiments, the critical thinking engine is further configured for generating a logical framework for interpreting of the question. The logical framework can include a catalog of paths from the question to respective answers. Each of the paths can include one or more linkages from the question to a path-specific answer. The linkages can include the internal concepts and external concepts derived from the store of subject matter ontology data. In some embodiments, the critical thinking engine is further configured for selecting a likely path from among the paths to a likely path-dependent answer based upon the intent. In some embodiments, the critical thinking engine is further configured for answering the question by following the likely path to the likely path-dependent answer.

According to some embodiments, a computer program product in a computer-readable medium for answering natural language questions posed by a user of a conversational interface of an artificial intelligence system is disclosed. The computer program product in a computer-readable medium can include instructions, which, when executed, cause a processor of a computer to perform tasks. In some embodiments, these tasks include receiving from a user interface a user-generated natural language query at an artificial intelligence-based conversation agent. In some embodiments, the tasks include extracting from the user-generated natural language query a question from a user of the user interface. In some embodiments, these tasks include compiling a language sample, wherein the language sample includes items of text derived from a conversation between the artificial intelligence-based conversation agent and the user. In some embodiments, the tasks include extracting from the language sample internal concepts and entities present within the language sample, wherein the internal concepts include descriptions of attributes of the entities. In some embodiments, the tasks include inferring an intent of the user from the internal concepts and the entities. In some embodiments, the tasks include generating a logical framework for interpreting of the question. The logical framework can include a catalog of paths from the question to respective answers. Each of the paths can include one or more linkages from the question to a path-specific answer. The linkages can include the internal concepts and external concepts derived from a store of subject matter ontology data. In some embodiments, the tasks include selecting a likely path from among the paths to a likely path-dependent answer based upon the intent. In some embodiments, the tasks include answering the question by following the likely path to the likely path-dependent answer.

According to some embodiments, a method for answering natural language questions posed by a user of a conversational interface of an artificial intelligence system is disclosed. In some embodiments, the method includes receiving from a user interface a user-generated natural language query at an artificial intelligence-based conversation agent. In some embodiments, the method further includes extracting from the user-generated natural language query a question from a user of the user interface. In some embodiments, the method further includes compiling a language sample, wherein the language sample can include items of text derived from a conversation between the artificial intelligence-based conversation agent and the user. In some embodiments, the method further includes extracting from the language sample internal concepts and entities present within the language sample. The internal concepts can include descriptions of attributes of the entities. In some embodiments, the method further includes inferring an intent of the user from the internal concepts and the entities. In some embodiments, the method further includes generating a logical framework for interpreting of the question. The logical framework can include a catalog of paths from the question to respective answers. Each of the paths can include one or more linkages from the question to a path-specific answer. The linkages can include the internal concepts and external concepts derived from a store of subject matter ontology data. In some embodiments, the method further includes selecting a likely path from among the paths to a likely path-dependent answer based upon the intent. In some embodiments, the method further includes answering the question by following the likely path to the likely path-dependent answer.

BRIEF DESCRIPTION OF THE DRAWINGS

For a detailed description of example embodiments, reference will now be made to the accompanying drawings in which:

FIGS. 8A, 8B, 8C, and 8D show aspects of a user interface, in accordance with various embodiments.

NOTATION AND NOMENCLATURE

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

According to some embodiments, a cognitive intelligence platform integrates and consolidates data from various sources and entities and provides a population health management service. The cognitive intelligence platform has the ability to extract concepts, relationships, and draw conclusions from a given text posed in natural language (e.g., a passage, a sentence, a phrase, and a question) by performing conversational analysis which includes analyzing conversational context. For example, the cognitive intelligence platform has the ability to identify the relevance of a posed question to another question.

The benefits provided by the cognitive intelligence platform, in the context of healthcare, include freeing up physicians from focusing on day to day population health management. Thus a physician can focus on her core competency—which includes disease/risk diagnosis and prognosis and patient care. The cognitive intelligence platform provides the functionality of a health coach and includes a physician's directions in accordance with the medical community's recommended care protocols and also builds a systemic knowledge base for health management.

Accordingly, the cognitive intelligence platform implements an intuitive conversational cognitive agent that engages in a question and answering system that is human-like in tone and response. The described cognitive intelligence platform endeavors to compassionately solve goals, questions and challenges. The described methods and systems are described as occurring in the healthcare space, though other areas are also contemplated.

Figure 1:
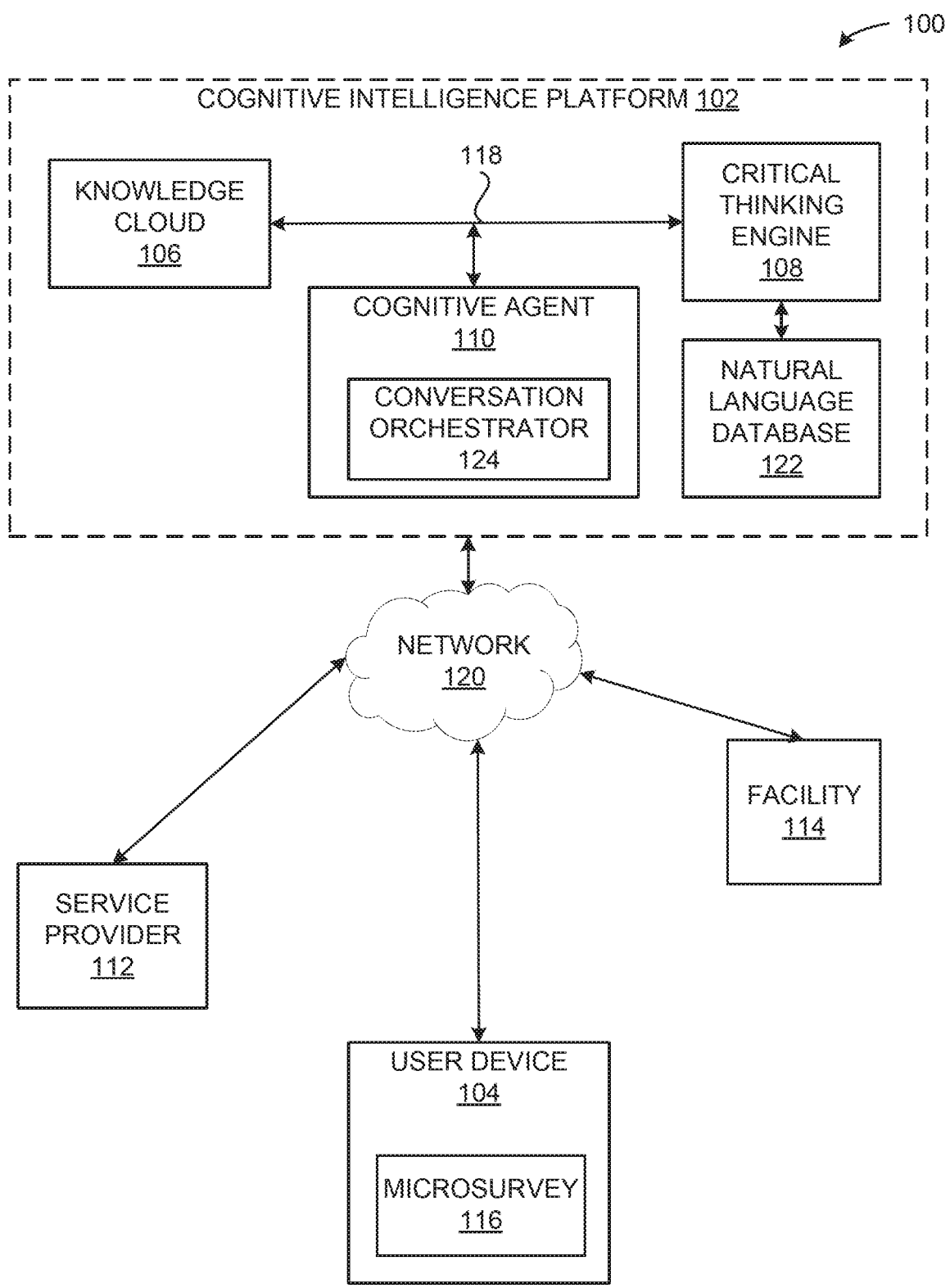
FIG. 1 illustrates, in block diagram form, a system architecture 100 that can be configured to provide a population health management service, in accordance with various embodiments.

FIG. 1 shows a system architecture 100 that can be configured to provide a population health management service, in accordance with various embodiments. Specifically, FIG. 1 illustrates a high-level overview of an overall architecture that includes a cognitive intelligence platform 102 communicably coupled to a user device 104. The cognitive intelligence platform 102 includes several computing devices, where each computing device, respectively, includes at least one processor, at least one memory, and at least one storage (e.g., a hard drive, a solid-state storage device, a mass storage device, and a remote storage device). The individual computing devices can represent any form of a computing device such as a desktop computing device, a rack-mounted computing device, and a server device. The foregoing example computing devices are not meant to be limiting. On the contrary, individual computing devices implementing the cognitive intelligence platform 102 can represent any form of computing device without departing from the scope of this disclosure.

The several computing devices work in conjunction to implement components of the cognitive intelligence platform 102 including: a knowledge cloud 106; a critical thinking engine 108; a natural language database 122; and a cognitive agent 110. The cognitive intelligence platform 102 is not limited to implementing only these components, or in the manner described in FIG. 1. That is, other system architectures can be implemented, with different or additional components, without departing from the scope of this disclosure. The example system architecture 100 illustrates one way to implement the methods and techniques described herein.

The knowledge cloud 106 represents a set of instructions executing within the cognitive intelligence platform 102 that implement a database configured to receive inputs from several sources and entities. For example, some of the sources an entities include a service provider 112, a facility 114, and a microsurvey 116—each described further below.

The critical thinking engine 108 represents a set of instructions executing within the cognitive intelligence platform 102 that execute tasks using artificial intelligence, such as recognizing and interpreting natural language (e.g., performing conversational analysis), and making decisions in a linear manner (e.g., in a manner similar to how the human left brain processes information). Specifically, an ability of the cognitive intelligence platform 102 to understand natural language is powered by the critical thinking engine 108. In various embodiments, the critical thinking engine 108 includes a natural language database 122. The natural language database 112 includes data curated over at least thirty years by linguists and computer data scientists, including data related to speech patterns, speech equivalents, and algorithms directed to parsing sentence structure.

Furthermore, the critical thinking engine 108 is configured to deduce causal relationships given a particular set of data, where the critical thinking engine 108 is capable of taking the individual data in the particular set, arranging the individual data in a logical order, deducing a causal relationship between each of the data, and drawing a conclusion. The ability to deduce a causal relationship and draw a conclusion (referred to herein as a "causal" analysis) is in direct contrast to other implementations of artificial intelligence that mimic the human left brain processes. For example, the other implementations can take the individual data and analyze the data to deduce properties of the data or statistics associated with the data (referred to herein as an "analytical" analysis). However, these other implementations are unable to perform a causal analysis—that is, deduce a causal relationship and draw a conclusion from the particular set of data. As described further below—the critical thinking engine 108 is capable of performing both types of analysis: causal and analytical.

The cognitive agent 110 represents a set of instructions executing within the cognitive intelligence platform 102 that implement a client-facing component of the cognitive intelligence platform 102. The cognitive agent 110 is an interface between the cognitive intelligence platform 102 and the user device 104. And in some embodiments, the cognitive agent 110 includes a conversation orchestrator 124 that determines pieces of communication that are presented to the user device 104 (and the user). When a user of the user device 104 interacts with the cognitive intelligence platform 102, the user interacts with the cognitive agent 110. The several references herein, to the cognitive agent 110 performing a method, can implicate actions performed by the critical thinking engine 108, which accesses data in the knowledge cloud 106 and the natural language database 122.

In various embodiments, the several computing devices executing within the cognitive intelligence platform are communicably coupled by way of a network/bus interface. Furthermore, the various components (e.g., the knowledge cloud 106, the critical thinking engine 108, and the cognitive agent 110), are communicably coupled by one or more inter-host communication protocols 118. In one example, the knowledge cloud 106 is implemented using a first computing device, the critical thinking engine 108 is implemented using a second computing device, and the cognitive agent 110 is implemented using a third computing device, where each of the computing devices are coupled by way of the inter-host communication protocol 118. Although in this example, the individual components are described as executing on separate computing devices this example is not meant to be limiting, the components can be implemented on the same computing device, or partially on the same computing device, without departing from the scope of this disclosure.

The user device 104 represents any form of a computing device, or network of computing devices, e.g., a personal computing device, a smart phone, a tablet, a wearable computing device, a notebook computer, a media player device, and a desktop computing device. The user device 104 includes a processor, at least one memory, and at least one storage. A user uses the user device 104 to input a given text posed in natural language (e.g., typed on a physical keyboard, spoken into a microphone, typed on a touch screen, or combinations thereof) and interacts with the cognitive intelligence platform 102, by way of the cognitive agent 110.

The architecture 100 includes a network 120 that communicatively couples various devices, including the cognitive intelligence platform 102 and the user device 104. The network 120 can include local area network (LAN) and wide area networks (WAN). The network 102 can include wired technologies (e.g., Ethernet®) and wireless technologies (e.g., Wi-Fi®, code division multiple access (CDMA), global system for mobile (GSM), universal mobile telephone service (UMTS), Bluetooth®, and ZigBee®. For example, the user device 104 can use a wired connection or a wireless technology (e.g., Wi-Fi®) to transmit and receive data over the network 120.

Still referring to FIG. 1, the knowledge cloud 106 is configured to receive data from various sources and entities and integrate the data in a database. An example source that provides data to the knowledge could 106 is the service provider 112, an entity that provides a type of service to a user. For example, the service provider 112 can be a health service provider (e.g., a doctor's office, a physical therapist's office, a nurse's office, or a clinical social worker's office), and a financial service provider (e.g., an accountant's office). For purposes of this discussion, the cognitive intelligence platform 102 provides services in the health industry, thus the examples discussed herein are associated with the health industry. However, any service industry can benefit from the disclosure herein, and thus the examples associated with the health industry are not meant to be limiting.

Throughout the course of a relationship between the service provider 112 and a user (e.g., the service provider 112 provides healthcare to a patient), the service provider 112 collects and generates data associated with the patient or the user, including health records that include doctor's notes and prescriptions, billing records, and insurance records. The service provider 112, using a computing device (e.g., a desktop computer or a tablet), provides the data associated with the user to the cognitive intelligence platform 102, and more specifically the knowledge cloud 106.

Another example source that provides data to the knowledge cloud 106 is the facility 114. The facility 114 represents a location owned, operated, or associated with any entity including the service provider 112. As used herein, an entity represents an individual or a collective with a distinct and independent existence. An entity can be legally recognized (e.g., a sole proprietorship, a partnership, a corporation) or less formally recognized in a community. For example, the entity can include a company that owns or operates a gym (facility). Additional examples of the facility 114 include, but is not limited to, a hospital, a trauma center, a clinic, a dentist's office, a pharmacy, a store (including brick and mortar stores and online retailers), an out-patient care center, a specialized care center, a birthing center, a gym, a cafeteria, and a psychiatric care center.

As the facility 114 represents a large number of types of locations, for purposes of this discussion and to orient the reader by way of example, the facility 114 represents the doctor's office or a gym. The facility 114 generates additional data associated with the user such as appointment times, an attendance record (e.g., how often the user goes to the gym), a medical record, a billing record, a purchase record, an order history, and an insurance record. The facility 114, using a computing device (e.g., a desktop computer or a tablet), provides the data associated with the user to the cognitive intelligence platform 102, and more specifically the knowledge cloud 106.

An additional example source that provides data to the knowledge cloud 106 is the microsurvey 116. The microsurvey 116 represents a tool created by the cognitive intelligence platform 102 that enables the knowledge cloud 106 to collect additional data associated with the user. The microsurvey 116 is originally provided by the cognitive intelligence platform 102 (by way of the cognitive agent 110) and the user provides data responsive to the microsurvey 116 using the user device 104. Additional details of the microsurvey 116 are described below.

Yet another example source that provides data to the knowledge cloud 106, is the cognitive intelligence platform 102, itself. In order to address the care needs and well-being of the user, the cognitive intelligence platform 102 collects, analyzes, and processes information from the user, healthcare providers, and other eco-system participants, and consolidates and integrates the information into knowledge. The knowledge can be shared with the user and stored in the knowledge cloud 106.

In various embodiments, the computing devices used by the service provider 112 and the facility 114 are communicatively coupled to the cognitive intelligence platform 102, by way of the network 120. While data is used individually by various entities including: a hospital, practice group, facility, or provider, the data is less frequently integrated and seamlessly shared between the various entities in the current art. The cognitive intelligence platform 102 provides a solution that integrates data from the various entities. That is, the cognitive intelligence platform 102 ingests, processes, and disseminates data and knowledge in an accessible fashion, where the reason for a particular answer or dissemination of data is accessible by a user.

In particular, the cognitive intelligence platform 102 (e.g., by way of the cognitive agent 110 interacting with the user) holistically manages and executes a health plan for durational care and wellness of the user (e.g., a patient or consumer). The health plan includes various aspects of durational management that is coordinated through a care continuum.

The cognitive agent 110 can implement various personas that are customizable. For example, the personas can include knowledgeable (sage), advocate (coach), and witty friend (jester). And in various embodiments, the cognitive agent 110 persists with a user across various interactions (e.g., conversations streams), instead of being transactional or transient. Thus, the cognitive agent 110 engages in dynamic conversations with the user, where the cognitive intelligence platform 102 continuously deciphers topics that a user wants to talk about. The cognitive intelligence platform 102 has relevant conversations with the user by ascertaining topics of interest from a given text posed in a natural language input by the user. Additionally the cognitive agent 110 connects the user to healthcare service providers, hyperlocal health communities, and a variety of services and tools/devices, based on an assessed interest of the user.

As the cognitive agent 110 persists with the user, the cognitive agent 110 can also act as a coach and advocate while delivering pieces of information to the user based on tonal knowledge, human-like empathies, and motivational dialog within a respective conversational stream, where the conversational stream is a technical discussion focused on a specific topic. Overall, in response to a question—e.g., posed by the user in natural language—the cognitive intelligence platform 102 consumes data from and related to the user and computes an answer. The answer is generated using a rationale that makes use of common sense knowledge, domain knowledge, evidence-based medicine guidelines, clinical ontologies, and curated medical advice. Thus, the content displayed by the cognitive intelligence platform 102 (by way of the cognitive agent 110) is customized based on the language used to communicate with the user, as well as factors such as a tone, goal, and depth of topic to be discussed.

Overall, the cognitive intelligence platform 102 is accessible to a user, a hospital system, and physician. Additionally, the cognitive intelligence platform 102 is accessible to paying entities interested in user behavior—e.g., the outcome of physician-consumer interactions in the context of disease or the progress of risk management. Additionally, entities that provides specialized services such as tests, therapies, and clinical processes that need risk based interactions can also receive filtered leads from the cognitive intelligence platform 102 for potential clients.

Conversational Analysis

In various embodiments, the cognitive intelligence platform 102 is configured to perform conversational analysis in a general setting. The topics covered in the general setting is driven by the combination of agents (e.g., cognitive agent 110) selected by a user. In some embodiments, the cognitive intelligence platform 102 uses conversational analysis to identify the intent of the user (e.g., find data, ask a question, search for facts, find references, and find products) and a respective micro-theory in which the intent is logical.

For example, the cognitive intelligence platform 102 applies conversational analysis to decode what the user is asking or stated, where the question or statement is in free form language (e.g., natural language). Prior to determining and sharing knowledge (e.g., with the user or the knowledge cloud 106), using conversational analysis, the cognitive intelligence platform 102 identifies an intent of the user and overall conversational focus.

The cognitive intelligence platform 102 responds to a statement or question according to the conversational focus and steers away from another detected conversational focus so as to focus on a goal defined by the cognitive agent 110. Given an example statement of a user, "I want to fly out tomorrow," the cognitive intelligence platform 102 uses conversational analysis to determine an intent of the statement. Is the user aspiring to be bird-like or does he want to travel? In the former case, the micro-theory is that of human emotions whereas in the latter case, the micro-theory is the world of travel. Answers are provided to the statement depending on the micro-theory in which the intent logically falls.

The cognitive intelligence platform 102 utilize a combination of linguistics, artificial intelligence, and decision trees to decode what a user is asking or stating. The discussion includes methods and system design considerations and results from an existing embodiment. Additional details related to conversational analysis are discussed next.

Analyzing Conversational Context as Part of Conversational Analysis

For purposes of this discussion, the concept of analyzing conversational context as part of conversational analysis is now described. To analyze conversational context, the following steps are taken: 1) obtain text (e.g., receive a question) and perform translations; 2) understand concepts, entities, intents, and micro-theory; 3) relate and search; 4) ascertain the existence of related concepts; 5) logically frame concepts or needs; 6) understand the questions that can be answered from available data; and 7) answer the question. Each of the foregoing steps is discussed next, in turn.

Step 1: Obtain Text/Question and Perform Translations

In various embodiments, the cognitive intelligence platform 102 (FIG. 1) receives a text or question and performs translations as appropriate. The cognitive intelligence platform 102 supports various methods of input including text received from a touch interface (e.g., options presented in a microsurvey), text input through a microphone (e.g., words spoken into the user device), and text typed on a keyboard or on a graphical user interface. Additionally, the cognitive intelligence platform 102 supports multiple languages and auto translation (e.g., from English to Traditional/Simplified Chinese or vice versa).

The example text below is used to described methods in accordance with various embodiments herein:

"One day in January 1913. G. H. Hardy, a famous Cambridge University mathematician received a letter from an Indian named Srinivasa Ramanujan asking him for his opinion of 120 mathematical theorems that Ramanujan said he had discovered. To Hardy, many of the theorems made no sense. Of the others, one or two were already well-known. Ramanujan must be some kind of trickplayer, Hardy decided, and put the letter aside. But all that day the letter kept hanging round Hardy. Might there by something in those wild-looking theorems?

That evening Hardy invited another brilliant Cambridge mathematician, J. E. Littlewood, and the two men set out to assess the Indian's worth. That incident was a turning point in the history of mathematics.

At the time, Ramanujan was an obscure Madras Port Trust clerk. A little more than a year later, he was at Cambridge University, and beginning to be recognized as one of the most amazing mathematicians the world has ever known. Though he died in 1920, much of his work was so far in advance of his time that only in recent years is it beginning to be properly understood.

Indeed, his results are helping solve today's problems in computer science and physics, problems that he could have had no notion of.

For Indians, moreover, Ramanujan has a special significance. Ramanujan, through born in poor and ill-paid accountant's family 100 years ago, has inspired many Indians to adopt mathematics as career.

Much of Ramanujan's work is in number theory, a branch of mathematics that deals with the subtle laws and relationships that govern numbers. Mathematicians describe his results as elegant and beautiful but they are much too complex to be appreciated by laymen.

His life, though, is full of drama and sorrow. It is one of the great romantic stories of mathematics, a distressing reminder that genius can surface and rise in the most unpromising circumstances."

The cognitive intelligence platform 102 analyzes the example text above to detect structural elements within the example text (e.g., paragraphs, sentences, and phrases). In some embodiments, the example text is compared to other sources of text such as dictionaries, and other general fact databases (e.g., Wikipedia) to detect synonyms and common phrases present within the example text.

Step 2: Understand Concept, Entity, Intent, and Micro-Theory

In step 2, the cognitive intelligence platform 102 parses the text to ascertain concepts, entities, intents, and micro-theories. An example output after the cognitive intelligence platform 102 initially parses the text is shown below, where concepts, and entities are shown in bold.

"One day in January 1913. G. H. Hardy, a famous Cambridge University mathematician received a letter from an Indian named Srinivasa Ramanujan asking him for his opinion of 120 mathematical theorems that Ramanujan said he had discovered. To Hardy, many of the theorems made no sense. Of the others, one or two were already well-known. Ramanujan must be some kind of trickplayer, Hardy decided, and put the letter aside. But all that day the letter kept hanging round Hardy. Might there by something in those wild-looking theorems?

That evening Hardy invited another brilliant Cambridge mathematician, J. E. Littlewood, and the two men set out to assess the Indian's worth. That incident was a turning point in the history of mathematics.

At the time, Ramanujan was an obscure Madras Port Trust clerk. A little more than a year later, he was at Cambridge University, and beginning to be recognized as one of the most amazing mathematicians the world has ever known. Though he died in 1920, much of his work was so far in advance of his time that only in recent years is it beginning to be properly understood.

Indeed, his results are helping solve today's problems in computer science and physics, problems that he could have had no notion of.

For Indians, moreover, Ramanujan has a special significance. Ramanujan, through born in poor and ill-paid accountant's family 100 years ago, has inspired many Indians to adopt mathematics as career.

Much of Ramanujan's work is in number theory, a branch of mathematics that deals with the subtle laws and relationships that govern numbers. Mathematicians describe his results as elegant and beautiful but they are much too complex to be appreciated by laymen.

His life, though, is full of drama and sorrow. It is one of the great romantic stories of mathematics, a distressing reminder that genius can surface and rise in the most unpromising circumstances."

For example, the cognitive intelligence platform 102 ascertains that Cambridge is a university—which is a full understanding of the concept. The cognitive intelligence platform (e.g., the cognitive agent 110) understands what humans do in Cambridge, and an example is described below in which the cognitive intelligence platform 102 performs steps to understand a concept.

For example, in the context of the above example, the cognitive agent 110 understands the following concepts and relationships:

Cambridge employed John Edensor Littlewood (1)
Cambridge has the position Ramanujan's position at Cambridge University (2)
Cambridge employed G. H. Hardy. (3)

The cognitive agent 110 also assimilates other understandings to enhance the concepts, such as:

Cambridge has Trinity College as a suborganization. (4)
Cambride is located in Cambridge. (5)
Alan Turing is previously enrolled at Cambridge. (6)
Stephen Hawking attended Cambridge. (7)

The statements (1)-(7) are not picked at random. Instead the cognitive agent 110 dynamically constructs the statements (1)-(7) from logic or logical inferences based on the example text above. Formally, the example statements (1)-(7) are captured as follows:

(#$subOrganizations #$UniversityOfCambridge #$TrinityCollege-Cambridge-England) (8)
(#$placeInCity #$UniversityOfCambridge #$CityofCambridgeEngland) (9)
(#$schooling #$AlanTuring #$UniversityOfCambridge #$PreviouslyEnrolled)(10)
(#$hasAlumni #$UniversityOfCambridge #$StephenHawking) (11)

Step 3: Relate and Search

Next, in step 3, the cognitive agent 110 relates various entities and topics and follows the progression of topics in the example text. Relating includes the cognitive agent 110 understanding the different instances of Hardy are all the same person, and the instances of Hardy are different from the instances of Littlewood. The cognitive agent 110 also understands that the instances Hardy and Littlewood share some similarities—e.g., both are mathematicians and they did some work together at Cambridge on Number Theory. The ability to track this across the example text is referred to as following the topic progression with a context.

Step 4: Ascertain the Existence of Related Concepts

Next, in Step 4, the cognitive agent 110 asserts non-existent concepts or relations to form new knowledge. Step 4 is an optional step for analyzing conversational context. Step 4 enhances the degree to which relationships are understood or different parts of the example text are understood together. If two concepts appear to be separate—e.g., a relationship cannot be graphically drawn or logically expressed between enough sets of concepts—there is a barrier to understanding. The barriers are overcome by expressing additional relationships. The additional relationships can be discovered using strategies like adding common sense or general knowledge sources (e.g., using the common sense data 208) or adding in other sources including a lexical variant database, a dictionary, and a thesaurus.

One example of concept progression from the example text is as follows: the cognitive agent 110 ascertains the phrase "theorems that Ramanujan said he had discovered" is related to the phrase "his results", which is related to "Ramanujan's work is in number theory, a branch of mathematics that deals with the subtle laws and relationships that govern numbers."

Step 5: Logically Frame Concepts or Needs

In Step 5, the cognitive agent 110 determines missing parameters—which can include for example, missing entities, missing elements, and missing nodes—in the logical framework (e.g., with a respective micro-theory). The cognitive agent 110 determines sources of data that can inform the missing parameters. Step 5 can also include the cognitive agent 110 adding common sense reasoning and finding logical paths to solutions.

With regards to the example text, some common sense concepts include:

Mathematicians develop Theorems. (12)
Theorems are hard to comprehend. (13)
Interpretations are not apparent for years. (14)

Applications are developed over time. (15)

Mathematicians collaborate and assess work. (16)

With regards to the example text, some passage concepts include:

Ramanujan did Theorems in Early 20th Century. (17)

Hardy assessed Ramanujan's Theorems. (18)

Hardy collaborated with Littlewood. (19)

Hardy and Littlewood assessed Ramanujan's work (20)

Within the micro-theory of the passage analysis, the cognitive agent 110 understands and catalogs available paths to answer questions. In Step 5, the cognitive agent 110 makes the case that the concepts (12)-(20) are expressed together.

Step 6: Understand the Questions that can be Answered from Available Data In Step 6, the cognitive agent 110 parses sub-intents and entities. Given the example text, the following questions are answerable from the cognitive agent's developed understanding of the example text, where the understanding was developed using information and context ascertained from the example text as well as the common sense data 208 (FIG. 2):

What situation causally contributed to Ramanujan's position at Cambridge? (21)

Does the author of the passage regret that Ramanujan died prematurely? (22)

Does the author of the passage believe that Ramanujan is a mathematical genius?(23)

Based on the information that is understood by the cognitive agent 110, the questions (21)-(23) can be answered.

By using an exploration method such as random walks, the cognitive agent 110 makes a determination as the paths that are plausible and reachable with the context (e.g., micro-theory) of the example text. Upon explorations, the cognitive agent 110 catalogs a set of meaningful questions. The set of meaningful questions are not asked, but instead explored based on the cognitive agent's understanding of the example text.

Given the example text, an example of exploration that yields a positive result is: "a situation X that caused Ramanujan's position." In contrast, an example of exploration that causes irrelevant results is: "a situation Y that caused Cambridge." The cognitive agent 110 is able to deduce that the latter exploration is meaningless, in the context of a micro-theory, because situations do not cause universities. Thus the cognitive agent 110 is able to deduce, there are no answers to Y, but there are answers to X.

Step 7: Answer the Question

In Step 7, the cognitive agent 110 provides a precise answer to a question. For an example question such as: "What situation causally contributed to Ramanujan's position at Cambridge?" the cognitive agent 110 generates a precise answer using the example reasoning:

HardyandLittlewoodsEvaluatingOfRamanujansWork (24)

HardyBeliefThatRamanujanIsAnExpertInMathematics (25)

HardysBeliefThatRamanujanIsAnExpertInMathematicsAndAGenius (26)

In order to generate the above reasoning statements (24)-(26), the cognitive agent 110 utilizes a solver or prover in the context of the example text's micro-theory—and associated facts, logical entities, relations, and assertions. As an additional example, the cognitive agent 110 uses a reasoning library that is optimized for drawing the example conclusions above within the fact, knowledge, and inference space (e.g., work space) that the cognitive agent 110 maintains.

By implementing the steps 1-7, the cognitive agent 110 analyzes conversational context. The described method for analyzing conversation context can also be used for recommending items in conversations streams. A conversational stream is defined herein as a technical discussion focused on specific topics. As related to described examples herein, the specific topics relate to health (e.g., diabetes). Throughout the lifetime of a conversational stream, a cognitive agent 110 collect information over may channels such as chat, voice, specialized applications, web browsers, contact centers, and the like.

By implementing the methods to analyze conversational context, the cognitive agent 110 can recommend a variety of topics and items throughout the lifetime of the conversational stream. Examples of items that can be recommended by the cognitive agent 110 include: surveys, topics of interest, local events, devices or gadgets, dynamically adapted health assessments, nutritional tips, reminders from a health events calendar, and the like.

Accordingly, the cognitive intelligence platform 102 provides a platform that codifies and takes into consideration a set of allowed actions and a set of desired outcomes. The cognitive intelligence platform 102 relates actions, the sequences of subsequent actions (and reactions), desired sub-outcomes, and outcomes, in a way that is transparent and logical (e.g., explainable). The cognitive intelligence platform 102 can plot a next best action sequence and a planning basis (e.g., health care plan template, or a financial goal achievement template), also in a manner that is explainable. The cognitive intelligence platform 102 can utilize a critical thinking engine 108 and a natural language database 122 (e.g., a linguistics and natural language understanding system) to relate conversation material to actions.

For purposes of this discussion, several examples are discussed in which conversational analysis is applied within the field of durational and whole-health management for a user. The discussed embodiments holistically address the care needs and well-being of the user during the course of his life. The methods and systems described herein can also be used in fields outside of whole-health management, including: phone companies that benefits from a cognitive agent; hospital systems or physicians groups that want to coach and educate patients; entities interested in user behavior and the outcome of physician-consumer interactions in terms of a progress of disease or risk management; entities that provide specialized services (e.g., test, therapies, clinical processes) to filter leads; and sellers, merchants, stores and big box retailers that want to understand which product to sell.

Figure 2:
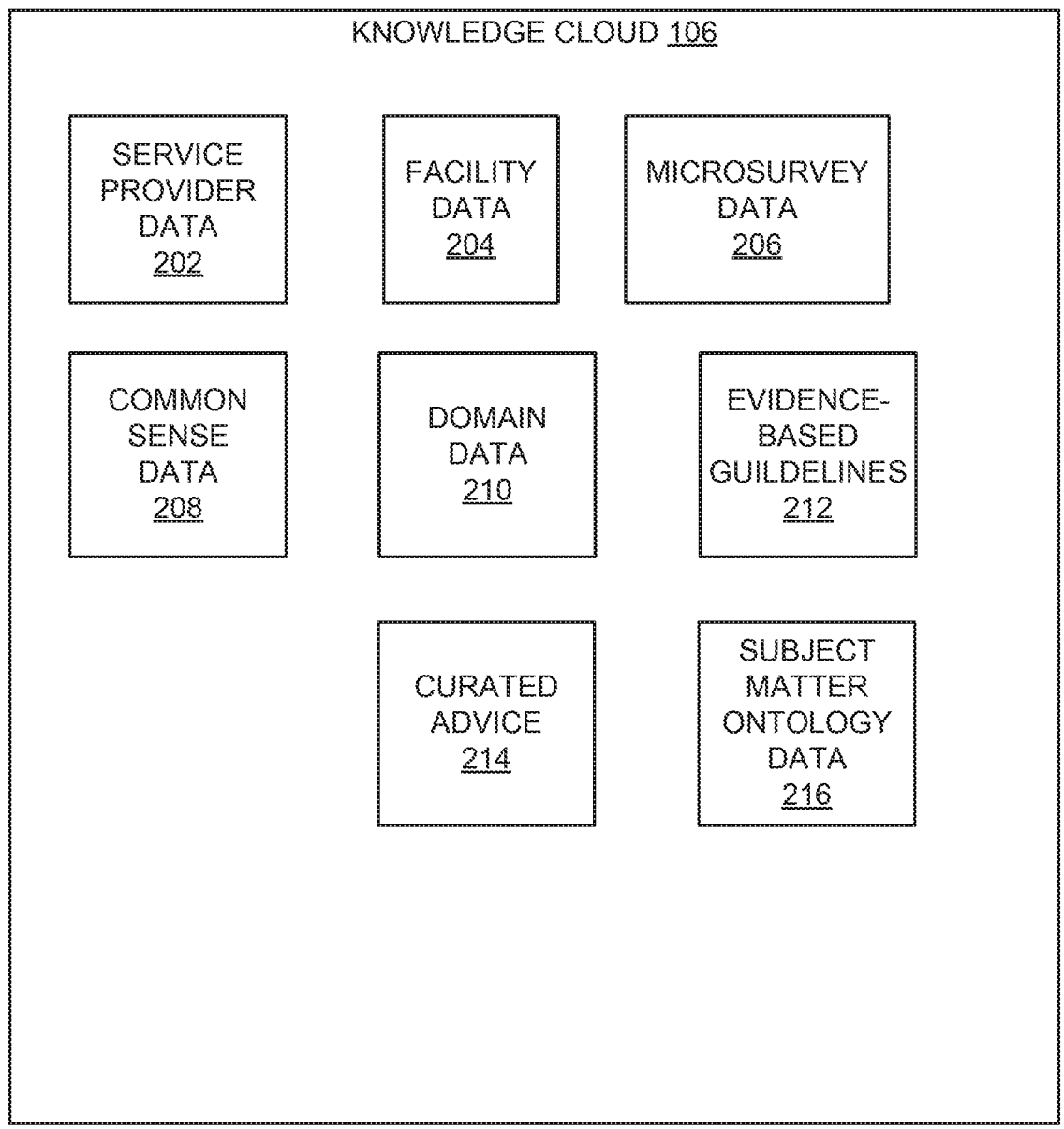
FIG. 2 shows additional details of a knowledge cloud, in accordance with various embodiments.

FIG. 2 shows additional details of a knowledge cloud, in accordance with various embodiments. In particular, FIG. 2 illustrates various types of data received from various sources, including service provider data 202, facility data 204, microsurvey data 206, commonsense data 208, domain data 210, evidence-based guidelines 212, subject matter ontology data 214, and curated advice 216. The types of data represented by the service provider data 202 and the facility data 204 include any type of data generated by the service provider 112 and the facility 114, and the above examples are not meant to be limiting. Thus, the example types of data are not meant to be limiting and other types of data can also be stored within the knowledge cloud 106 without departing from the scope of this disclosure.

The service provider data 202 is data provided by the service provider 112 (described in FIG. 1) and the facility data 204 is data provided by the facility 114 (described in FIG. 1). For example, the service provider data 202 includes medical records of a respective patient of a service provider 112 that is a doctor. In another example, the facility data 204 includes an attendance record of the respective patient, where the facility 114 is a gym. The microsurvey data 206 is data provided by the user device 104 responsive to questions presented in the microsurvey 116 (FIG. 1).

Common sense data 208 is data that has been identified as "common sense", and can include rules that govern a respective concept and used as glue to understand other concepts.

Domain data 210 is data that is specific to a certain domain or subject area. The source of the domain data 210 can include digital libraries. In the healthcare industry, for example, the domain data 210 can include data specific to the various specialties within healthcare such as, obstetrics, anesthesiology, and dermatology, to name a few examples. In the example described herein, the evidence-based guidelines 212 include systematically developed statements to assist practitioner and patient decisions about appropriate health care for specific clinical circumstances.

Curated advice 214 includes advice from experts in a subject matter. The curated advice 214 can include peer-reviewed subject matter, and expert opinions. Subject matter ontology data 216 includes a set of concepts and categories in a subject matter or domain, where the set of concepts and categories capture properties and relationships between the concepts and categories.

Figure 3:
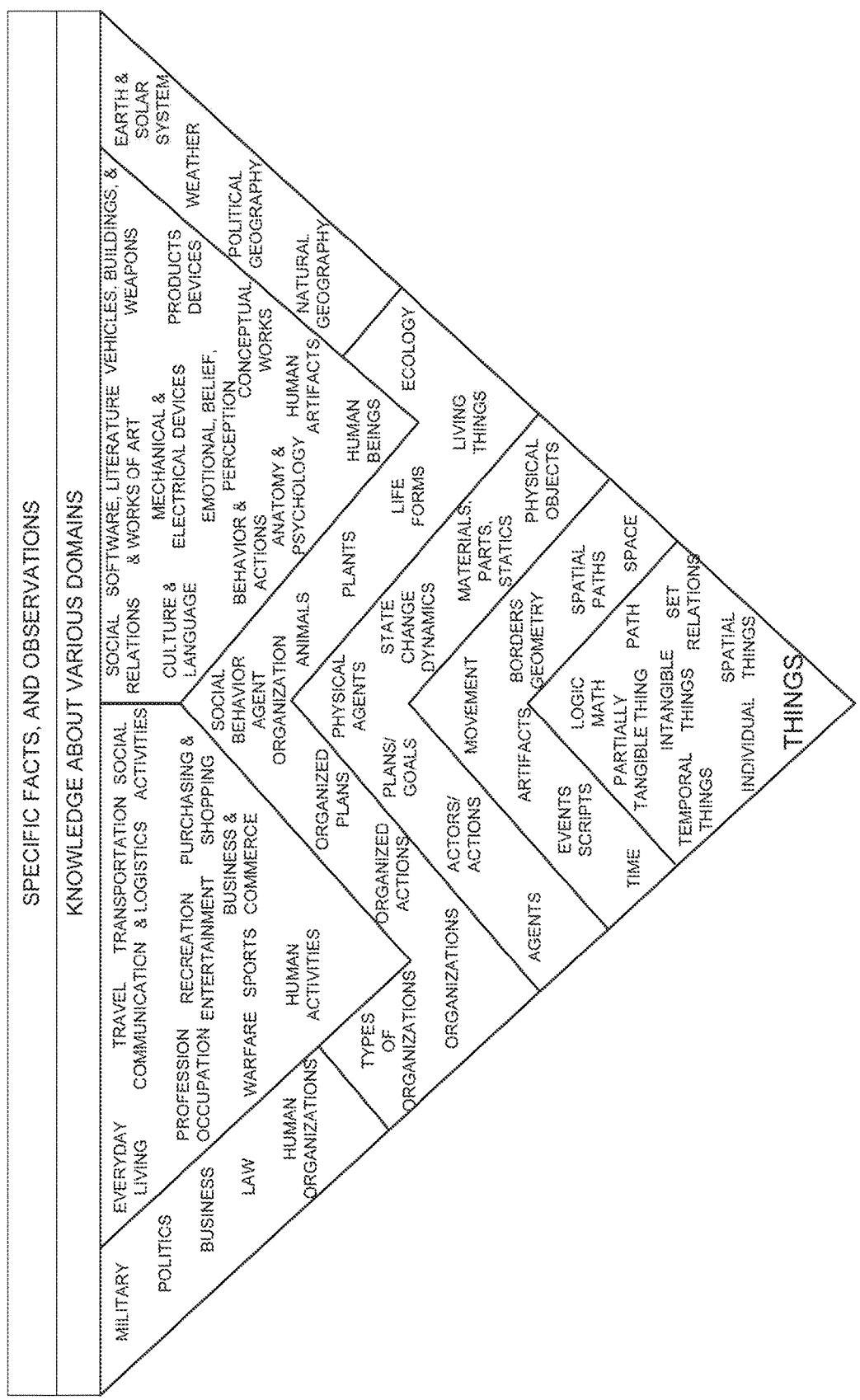
FIG. 3 shows an example subject matter ontology, in accordance with various embodiments.

In particular, FIG. 3 illustrates an example subject matter ontology 300 that is included as part of the subject matter ontology data 216.

Figure 4:
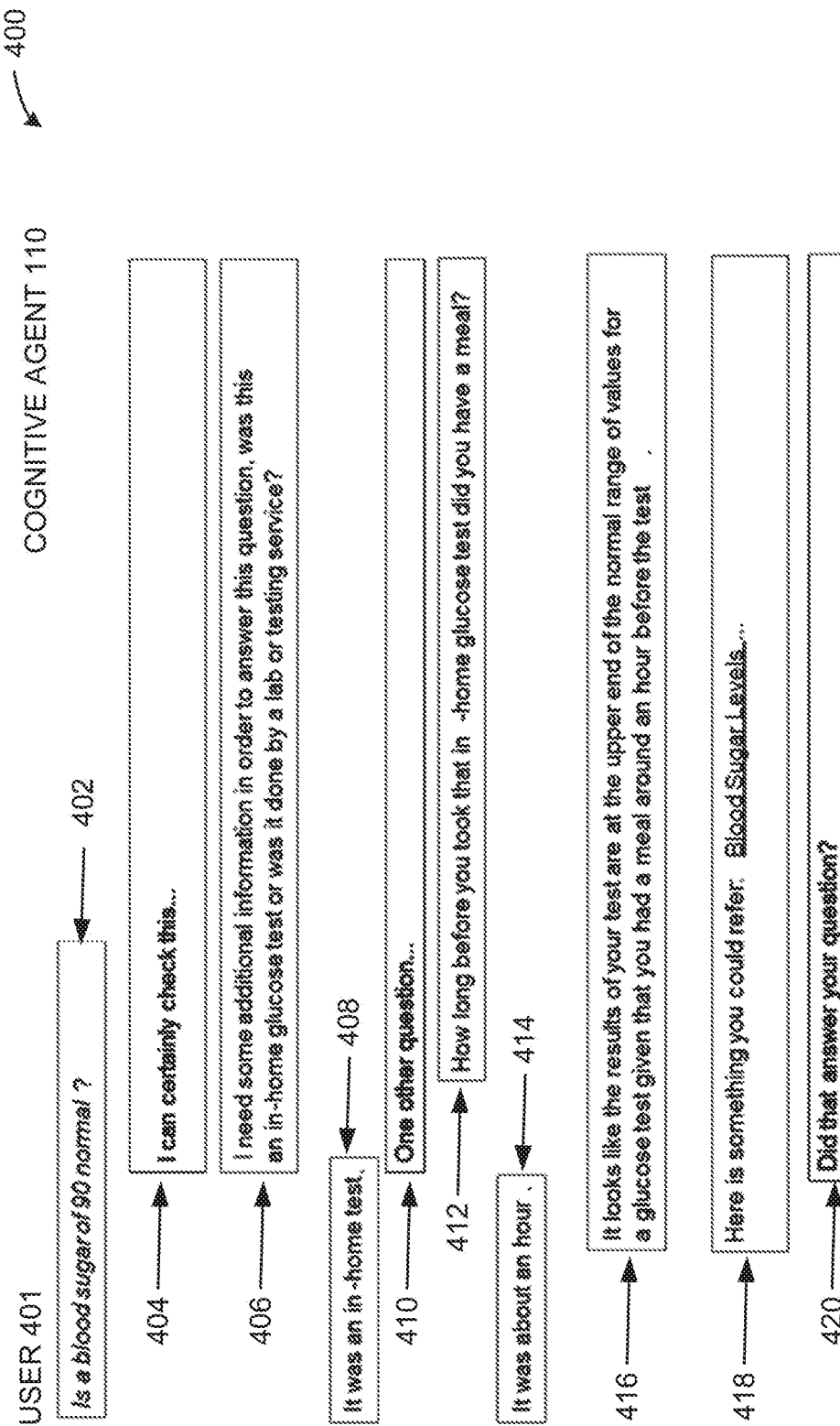
FIG. 4 shows aspects of a conversation, in accordance with various embodiments.

FIG. 4 illustrates aspects of a conversation 400 between a user and the cognitive intelligence platform 102, and more specifically the cognitive agent 110. For purposes of this discussion, the user 401 is a patient of the service provider 112. The user interacts with the cognitive agent 110 using a computing device, a smart phone, or any other device configured to communicate with the cognitive agent 110 (e.g., the user device 104 in FIG. 1). The user can enter text into the device using any known means of input including a keyboard, a touchscreen, and a microphone. The conversation 400 represents an example graphical user interface (GUI) presented to the user 401 on a screen of his computing device.

Initially, the user asks a general question, which is treated by the cognitive agent 110 as an "originating question." The originating question is classified into any number of potential questions ("pursuable questions") that are pursued during the course of a subsequent conversation. In some embodiments, the pursuable questions are identified based on a subject matter domain or goal. In some embodiments, classification techniques are used to analyze language (e.g., such as those outlined in HPS ID20180901-01_method for conversational analysis). Any known text classification technique can be used to analyze language and the originating question. For example, in line 402, the user enters an originating question about a subject matter (e.g., blood sugar) such as: "Is a blood sugar of 90 normal"?

In response to receiving an originating question, the cognitive intelligence platform 102 (e.g., the cognitive agent 110 operating in conjunction with the critical thinking engine 108) performs a first round of analysis (e.g., which includes conversational analysis) of the originating question and, in response to the first round of analysis, creates a workspace and determines a first set of follow up questions.

In various embodiments, the cognitive agent 110 may go through several rounds of analysis executing within the workspace, where a round of analysis includes: identifying parameters, retrieving answers, and consolidating the answers. The created workspace can represent a space where the cognitive agent 110 gathers data and information during the processes of answering the originating question. In various embodiments, each originating question corresponds to a respective workspace. The conversation orchestrator 124 can assess data present within the workspace and query the cognitive agent 110 to determine if additional data or analysis should be performed.

In particular, the first round of analysis is performed at different levels, including analyzing natural language of the text, and analyzing what specifically is being asked about the subject matter (e.g., analyzing conversational context). The first round of analysis is not based solely on a subject matter category within which the originating question is classified. For example, the cognitive intelligence platform 102 does not simply retrieve a predefined list of questions in response to a question that falls within a particular subject matter, e.g., blood sugar. That is, the cognitive intelligence platform 102 does not provide the same list of questions for all questions related to the particular subject matter. Instead, for example, the cognitive intelligence platform 102 creates dynamically formulated questions, curated based on the first round of analysis of the originating question.

In particular, during the first round of analysis, the cognitive agent 110 parses aspects of the originating question into associated parameters. The parameters represent variables useful for answering the originating question. For example, the question "is a blood sugar of 90 normal" may be parsed and associated parameters may include, an age of the inquirer, the source of the value 90 (e.g., in home test or a clinical test), a weight of the inquirer, and a digestive state of the user when the test was taken (e.g., fasting or recently eaten). The parameters identify possible variables that can impact, inform, or direct an answer to the originating question.

For purposes of the example illustrated in FIG. 4, in the first round of analysis, the cognitive intelligence platform 102 inserts each parameter into the workspace associated with the originating question (line 402). Additionally, based on the identified parameters, the cognitive intelligence platform 102 identifies a customized set of follow up questions ("a first set of follow-up questions). The cognitive intelligence platform 102 inserts first set of follow-up questions in the workspace associated with the originating question.

The follow up questions are based on the identified parameters, which in turn are based on the specifics of the originating question (e.g., related to an identified microtheory). Thus the first set of follow-up questions identified in response to, if a blood sugar is normal, will be different from a second set of follow up questions identified in response to a question about how to maintain a steady blood sugar.

After identifying the first set of follow up questions, in this example first round of analysis, the cognitive intelligence platform 102 determines which follow up question can be answered using available data and which follow-up question to present to the user. As described over the next few paragraphs, eventually, the first set of follow-up questions is reduced to a subset ("a second set of follow-up questions") that includes the follow-up questions to present to the user.

In various embodiments, available data is sourced from various locations, including a user account, the knowledge cloud 106, and other sources. Other sources can include a service that supplies identifying information of the user, where the information can include demographics or other characteristics of the user (e.g., a medical condition, a lifestyle). For example, the service can include a doctor's office or a physical therapist's office.

Another example of available data includes the user account. For example, the cognitive intelligence platform 102 determines if the user asking the originating question, is identified. A user can be identified if the user is logged into an account associated with the cognitive intelligence platform 102. User information from the account is a source of available data. The available data is inserted into the workspace of the cognitive agent 110 as a first data.

Another example of available data includes the data stored within the knowledge cloud 106. For example, the available data includes the service provider data 202 (FIG. 2), the facility data 204, the microsurvey data 206, the common sense data 208, the domain data 210, the evidence-based guidelines 212, the curated advice 214, and the subject matter ontology data 216. Additionally data stored within the knowledge cloud 106 includes data generated by the cognitive intelligence platform 102, itself.

Follow up questions presented to the user (the second set of follow-up questions) are asked using natural language and are specifically formulated ("dynamically formulated question") to elicit a response that will inform or fulfill an identified parameter. Each dynamically formulated question can target one parameter at a time. When answers are received from the user in response to a dynamically formulated question, the cognitive intelligence platform 102 inserts the answer into the workspace. In some embodiments, each of the answers received from the user and in response to a dynamically formulated question, is stored in a list of facts. Thus the list of facts include information specifically received from the user, and the list of facts is referred to herein as the second data.

With regards to the second set of follow-up questions (or any set of follow-up questions), the cognitive intelligence platform 102 calculates a relevance index, where the relevance index provides a ranking of the questions in the second set of follow-up questions. The ranking provides values indicative of how relevant a respective follow-up question is to the originating question. To calculate the relevance index, the cognitive intelligence platform 102 can use conversations analysis techniques described in HPS ID20180901-01_method. In some embodiments, the first set or second set of follow up questions is presented to the user in the form of the microsurvey 116.

In this first round of analysis, the cognitive intelligence platform 102 consolidates the first and second data in the workspace and determines if additional parameters need to be identified, or if sufficient information is present in the workspace to answer the originating question. In some embodiments, the cognitive agent 110 (FIG. 1) assesses the data in the workspace and queries the cognitive agent 110 to determine if the cognitive agent 110 needs more data in order to answer the originating question. The conversation orchestrator 124 executes as an interface For a complex originating question, the cognitive intelligence platform 102 can go through several rounds of analysis. For example, in a first round of analysis the cognitive intelligence platform 102 parses the originating question. In a subsequent round of analysis, the cognitive intelligence platform 102 can create a sub question, which is subsequently parsed into parameters in the subsequent round of analysis. The cognitive intelligence platform 102 is smart enough to figure out when all information is present to answer an originating question without explicitly programming or pre-programming the sequence of parameters that need to be asked about.

In some embodiments, the cognitive agent 110 is configured to process two or more conflicting pieces of information or streams of logic. That is, the cognitive agent 110, for a given originating question can create a first chain of logic and a second chain of logic that leads to different answers. The cognitive agent 110 has the capability to assess each chain of logic and provide only one answer. That is, the cognitive agent 110 has the ability to process conflicting information received during a round of analysis.

Additionally, at any given time, the cognitive agent 110 has the ability to share its reasoning (chain of logic) to the user. If the user does not agree with an aspect of the reasoning, the user can provide that feedback which results in affecting change in a way the critical thinking engine 108 analyzed future questions and problems.

Subsequent to determining enough information is present in the workspace to answer the originating question, the cognitive agent 110 answers the question, and additionally can suggest a recommendation or a recommendation (e.g., line 418). The cognitive agent 110 suggests the reference or the recommendation based on the context and questions being discussed in the conversation (e.g., conversation 400). The reference or recommendation serves as additional handout material to the user and is provided for informational purposes. The reference or recommendation often educates the user about the overall topic related to the originating question.

In the example illustrated in FIG. 4, in response to receiving the originating questions (line 402), the cognitive intelligence platform 102 (e.g., the cognitive agent 110 in conjunction with the critical thinking engine 108) parses the originating question to determine at least one parameter: location. The cognitive intelligence platform 102 categorizes this parameter, and a corresponding dynamically formulated question in the second set of follow-up questions. Accordingly, in lines 404 and 406, the cognitive agent 110 responds by notifying the user "I can certainly check this . . . " and asking the dynamically formulated question "I need some additional information in order to answer this question, was this an in-home glucose test or was it done by a lab or testing service?"

The user 401 enters his answer in line 408: "It was an in-home test," which the cognitive agent 110 further analyzes to determine additional parameters: e.g., a digestive state, where the additional parameter and a corresponding dynamically formulated question as an additional second set of follow-up questions. Accordingly, the cognitive agent 110 poses the additional dynamically formulated question in lines 410 and 412: "One other question . . . " and "How long before you took that in-home glucose test did you have a meal?" The user provides additional information in response "it was about an hour" (line 414).

The cognitive agent 110 consolidates all the received responses using the critical thinking engine 108 and the knowledge cloud 106 and determines an answer to the initial question posed in line 402 and proceeds to follow up with a final question to verify the user's initial question was answered. For example, in line 416, the cognitive agent 110 responds: "It looks like the results of your test are at the upper end of the normal range of values for a glucose test given that you had a meal around an hour before the test." The cognitive agent 110 provides additional information (e.g., provided as a link): "Here is something you could refer," (line 418), and follows up with a question "Did that answer your question?" (line 420).

As described above, due to the natural language database 108, in various embodiments, the cognitive agent 110 is able to analyze and respond to questions and statements made by a user 401 in natural language. That is, the user 401 is not restricted to using certain phrases in order for the cognitive agent 110 to understand what a user 401 is saying. Any phrasing, similar to how the user would speak naturally can be input by the user and the cognitive agent 110 has the ability to understand the user.

Figure 5:
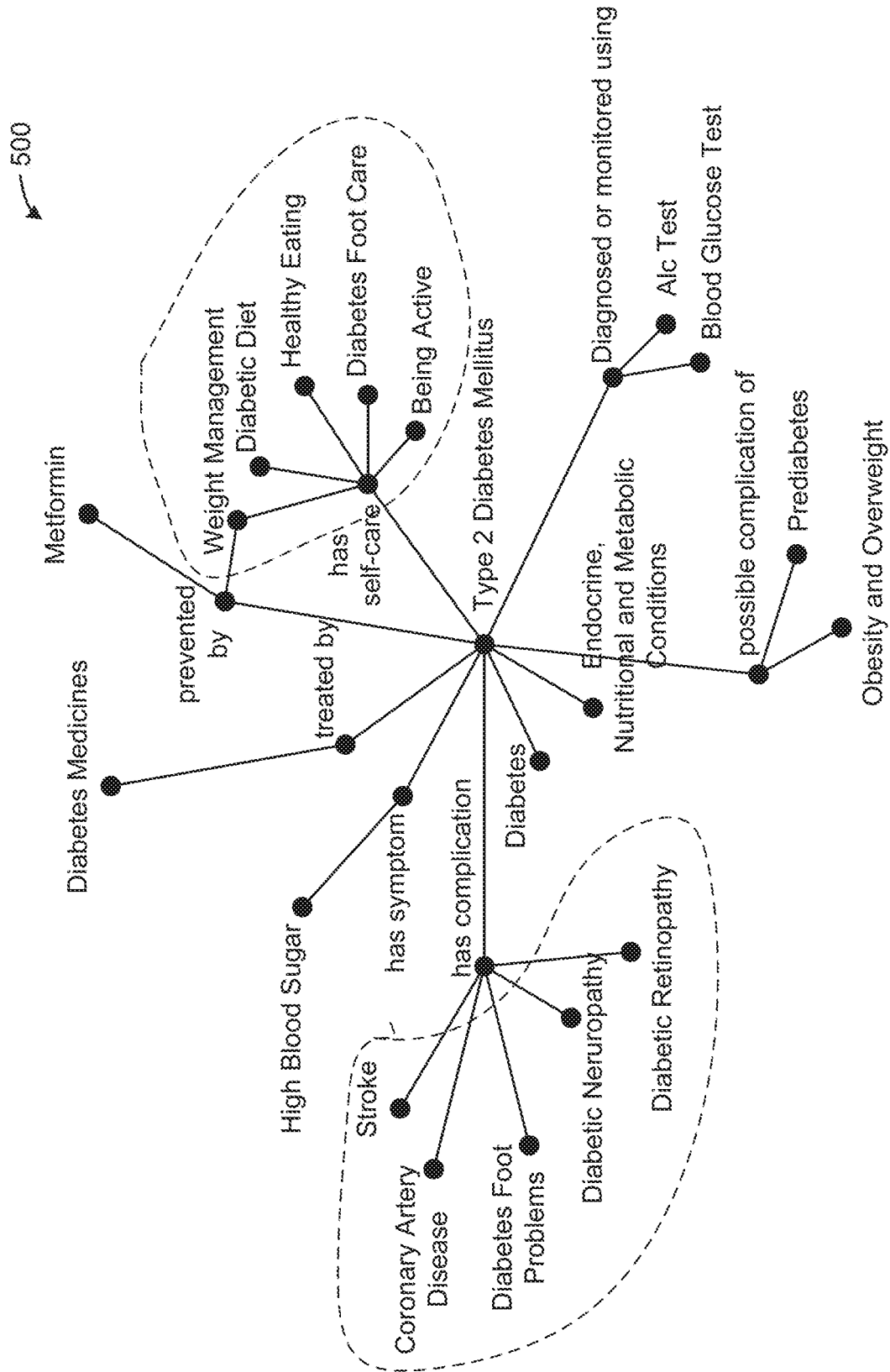
FIG. 5 shows a cognitive map or "knowledge graph", in accordance with various embodiments.

FIG. 5 illustrates a cognitive map or "knowledge graph" 500, in accordance with various embodiments. In particular, the knowledge graph represents a graph traversed by the cognitive intelligence platform 102, when assessing questions from a user with Type 2 diabetes. Individual nodes in the knowledge graph 500 represent a health artifact or relationship that is gleaned from direct interrogation or indirect interactions with the user (by way of the user device 104).

In one embodiment, the cognitive intelligence platform 102 identified parameters for an originating question based on a knowledge graph illustrated in FIG. 5. For example, the cognitive intelligence platform 102 parses the originating question to determine which parameters are present for the originating question. In some embodiments, the cognitive intelligence platform 102 infers the logical structure of the parameters by traversing the knowledge graph 500, and additionally, knowing the logical structure enables the cognitive agent 110 to formulate an explanation as to why the cognitive agent 110 is asking a particular dynamically formulated question.

Figure 6:
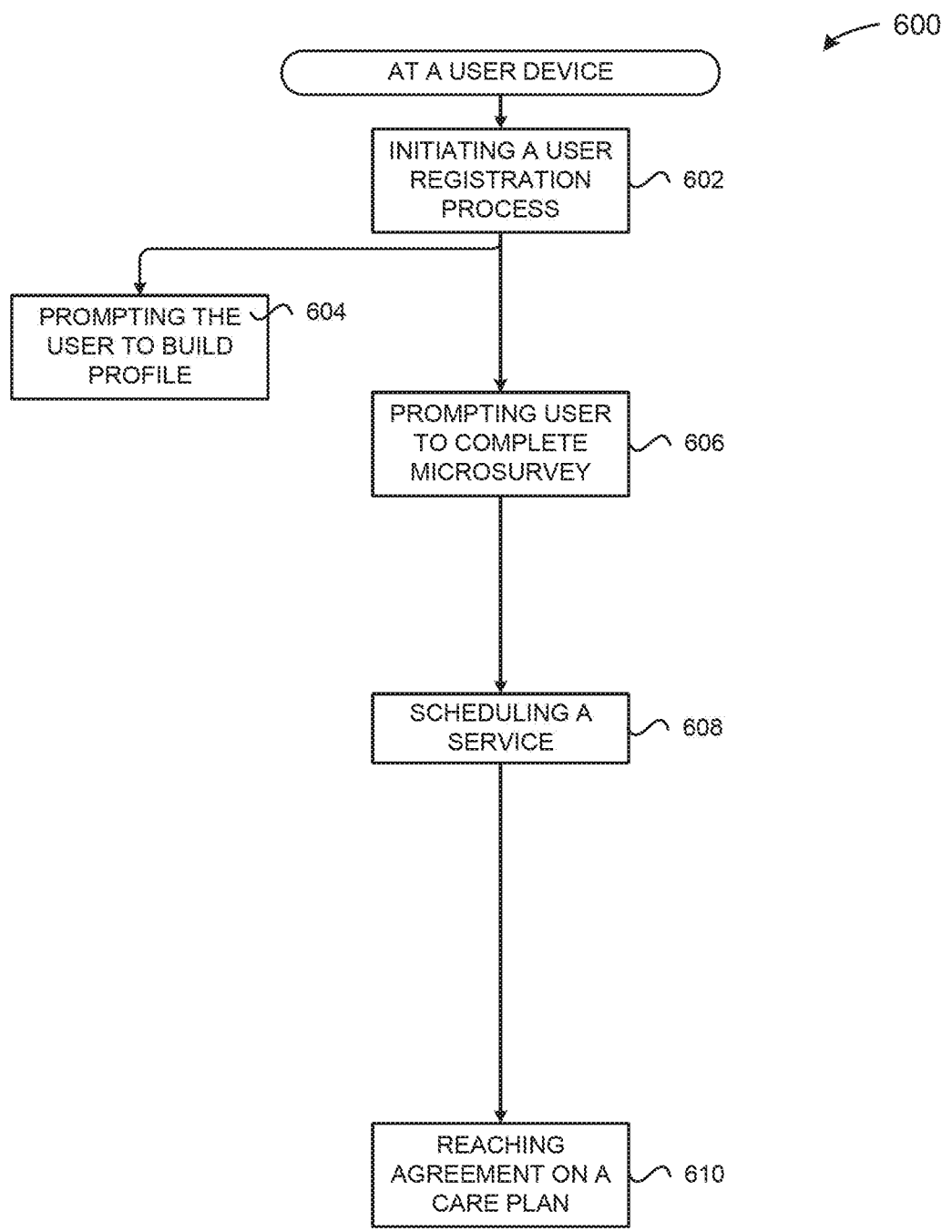
FIG. 6 shows a method, in accordance with various embodiments.

FIG. 6 shows a method, in accordance with various embodiments. The method is performed at a user device (e.g., the user device 102) and in particular, the method is performed by an application executing on the user device 102. The method begins with initiating a user registration process (block 602). The user registration can include tasks such as displaying a GUI asking the user to enter in personal information such as his name and contact information.

Next, the method includes prompting the user to build his profile (block 604). In various embodiments, building his profile includes displaying a GUI asking the user to enter in additional information, such as age, weight, height, and health concerns. In various embodiments, the steps of building a user profile is progressive, where building the user profile takes place over time. In some embodiments, the process of building the user profile is presented as a game. Where a user is presented with a ladder approach to create a "star profile". Aspects of a graphical user interface presented during the profile building step are additionally discussed in FIGS. 8A-8B.

The method contemplates the build profile (block 604) method step is optional. For example, the user may complete building his profile at this method step 604, the user may complete his profile at a later time, or the cognitive intelligence platform 102 builds the user profile over time as more data about the user is received and processed. For example, the user is prompted to build his profile, however, the user fails to enter in information or skips the step. The method proceeds to prompting a user to complete a microsurvey (block 606). In some embodiments, the cognitive agent 110 uses answers received in response to the microsurvey to build the profile of the user. Overall, the data collected through the user registration process is stored and used later as available data to inform answers to missing parameters.

Next, the cognitive agent 110 proceeds to scheduling a service (block 608). The service can be scheduled such that it aligns with a health plan of the user or a protocol that results in a therapeutic goal. Next, the cognitive agent 110 proceeds to reaching agreement on a care plan (block 610).

Figure 7A:
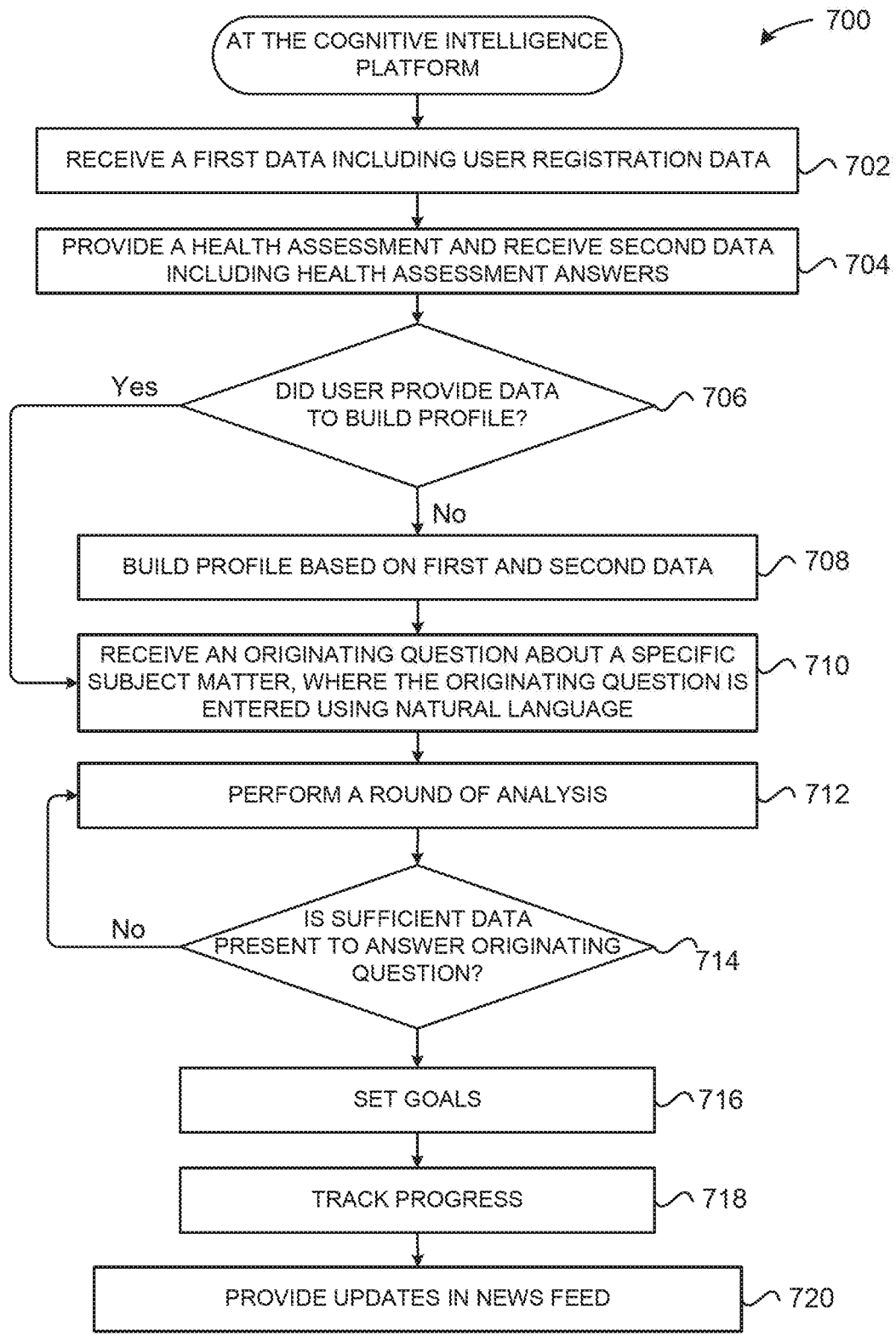
FIGS. 7A, 7B, and 7C show methods, in accordance with various embodiments.
Figure 7B:
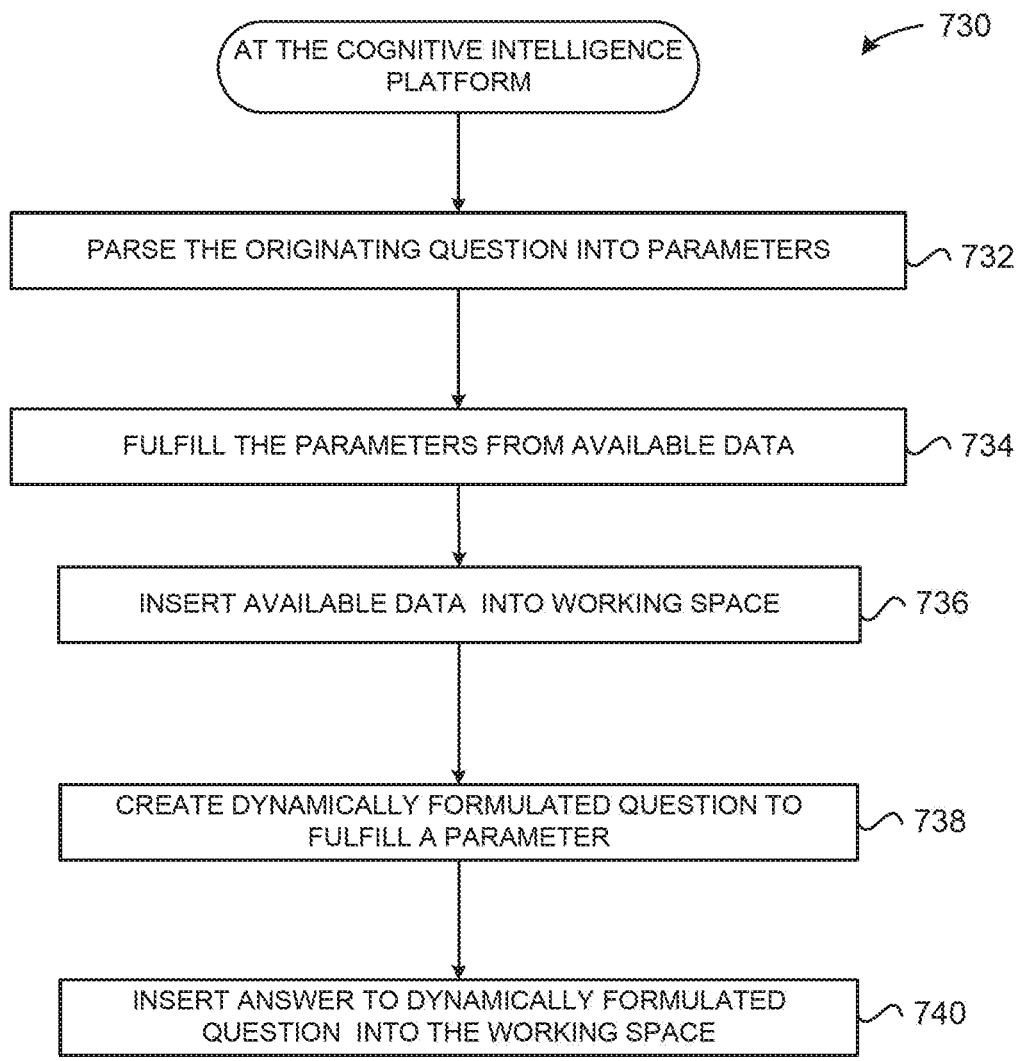
Figure 7C:
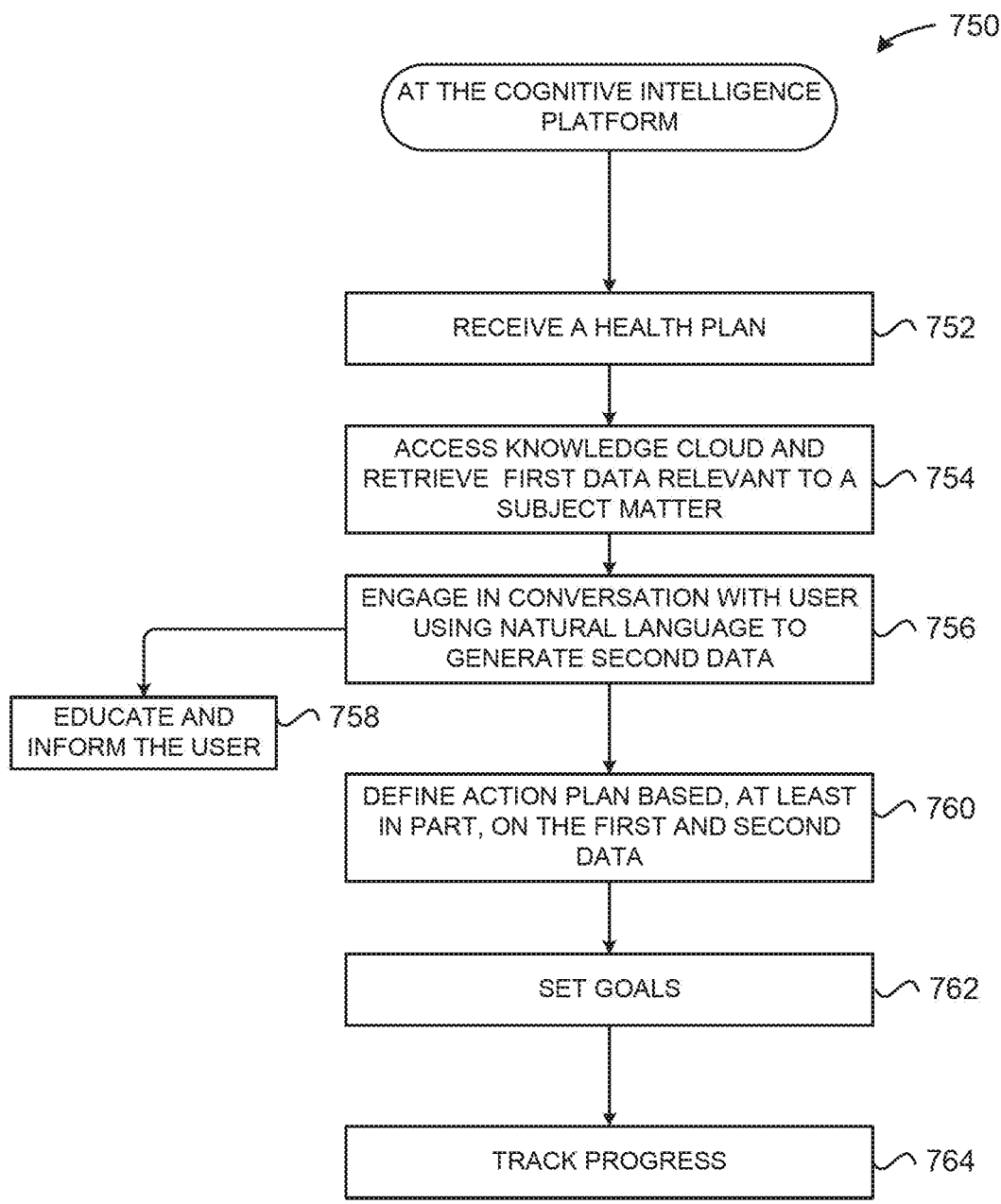

FIGS. 7A, 7B, and 7C, show methods, in accordance with various embodiments. The methods are performed at the cognitive intelligence platform. In particular, in FIG. 7A, the method begins with receiving a first data including user registration data (block 702); and providing a health assessment and receiving second data including health assessment answers (block 704). In various embodiments, the health assessment is a micro-survey with dynamically formulated questions presented to the user.

Next the method determine if the user provided data to build a profile (decision block 706). If the user did not provide data to build the profile, the method proceeds to building profile based on first and second data (block 708). If the user provided data to build the profile, the method proceeds to block 710.

At block 710, the method 700 proceeds to receiving an originating question about a specific subject matter, where the originating question is entered using natural language, and next the method proceeds to performing a round of analysis (block 712). Next, the method determines if sufficient data is present to answer originating questions (decision block 714). If no, the method proceeds to block 712 and the method performs another round of analysis. If yes, the method proceeds to setting goals (block 716), then tracking progress (block 718), and then providing updates in a news feed (block 720).

In FIG. 7B, a method 730 of performing a round of analysis is illustrated. The method begins with parsing the originating question into parameters (block 732); fulfilling the parameters from available data (block 734); inserting available data (first data) into a working space (block 736); creating a dynamically formulated question to fulfill a parameter (block 738); and inserting an answer to the dynamically formulated question into the working space (block 740).

In FIG. 7C, a method 750 is performed at the cognitive intelligence platform. The method begins with receiving a health plan (block 752); accessing the knowledge cloud and retrieving first data relevant to the subject matter (block 754); and engaging in conversation with the user using natural language to general second data (block 756). In various embodiments, the second data can include information such as a user's scheduling preferences, lifestyle choices, and education level. During the process of engaging in conversation, the method includes educating and informing the user (block 758). Next, the method includes defining an action plan based, at least in part, on the first and second data (block 760); setting goals (block 762); and tracking progress (block 764).

FIGS. 8A, 8B, 8C, and 8D illustrate aspects of interactions between a user and the cognitive intelligence platform 102, in accordance with various embodiments. As a user interacts with the GUI, the cognitive intelligence platform 102 continues to build a database of knowledge about the user based on questions asked by the user as well as answers provided by the user (e.g., available data as described in FIG. 4). In particular, FIG. 8A displays a particular screen shot 801 of the user device 104 at a particular instance in time. The screen shot 801 displays a graphical user interface (GUI) with menu items associated with a user's (e.g., Nathan) profile including Messages from the doctor (element 804), Goals (element 806), Trackers (element 808), Health Record (element 810), and Health Plans & Assessments (element 812). The menu item Health Plans & Assessments (element 812), additionally include child menu items: Health Assessments (element 812*a*), Health plans (812*b*).

The screen shot 803 displays the same GUI as in the screen shot 801, however, the user has scrolled down the menu, such that additional menu items below Health Plans & Assessments (element 812) are shown. The additional menu items include Reports (element 814), Health Team (element 816), and Purchases and Services (Element 818). Furthermore, additional menu items include Add your Health Team (element 820) and Read about improving your A1C levels (element 822).

Figure 8A:
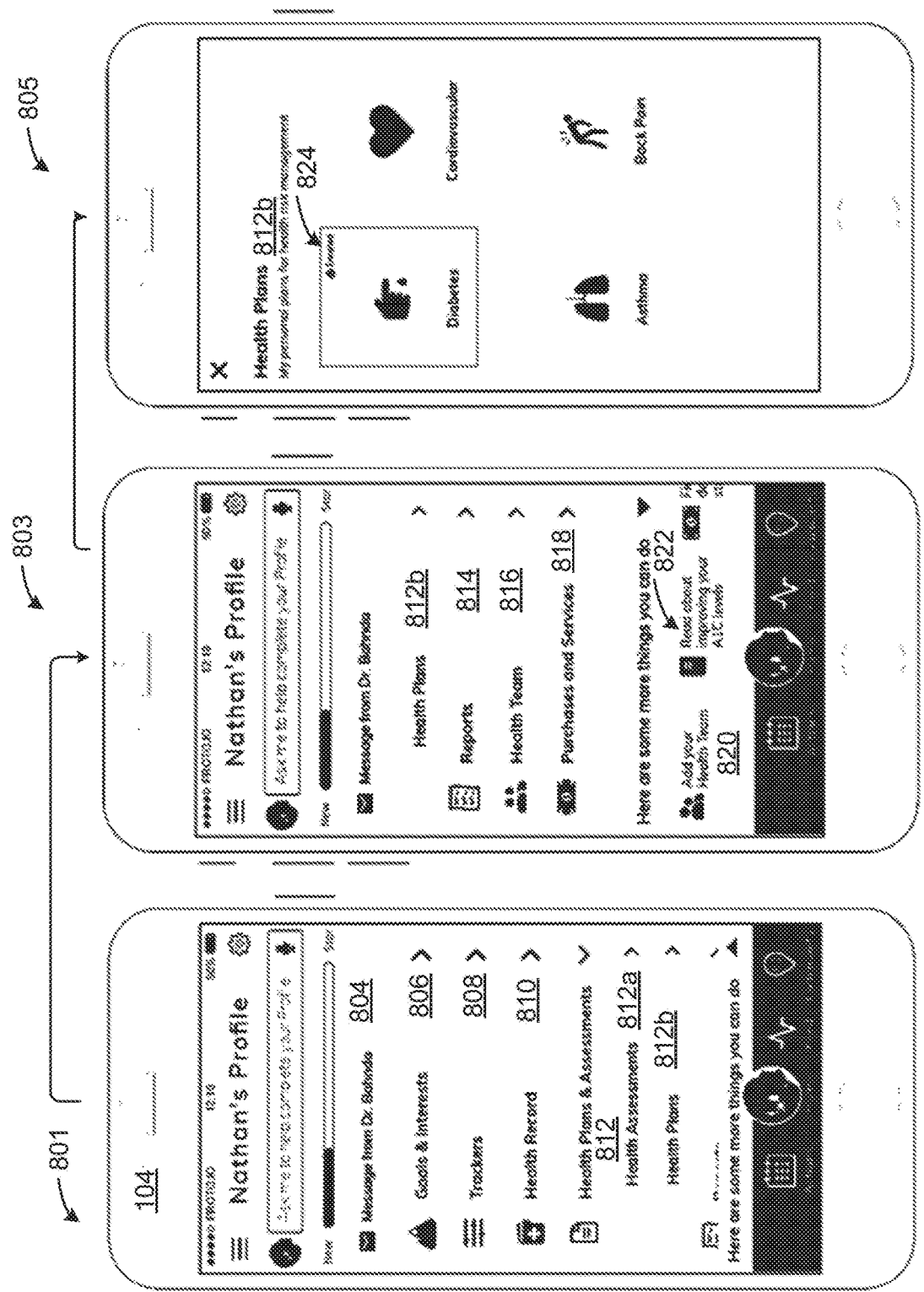

For purposes of the example in FIG. 8A, the user selects the menu item Health Plans (element 812b). Accordingly, in response to the receiving the selection of the menu item Health Plans, types of health plans are shown, as illustrated in screen shot 805. The types of health plans shown with respect to Nathan's profile include: Diabetes (element 824), Cardiovascular, Asthma, and Back Pain. Each type of health plan leads to separate displays. For purposes of this example in FIG. 8A, the user selects the Diabetes (element 824) health plan.

Figure 8B:
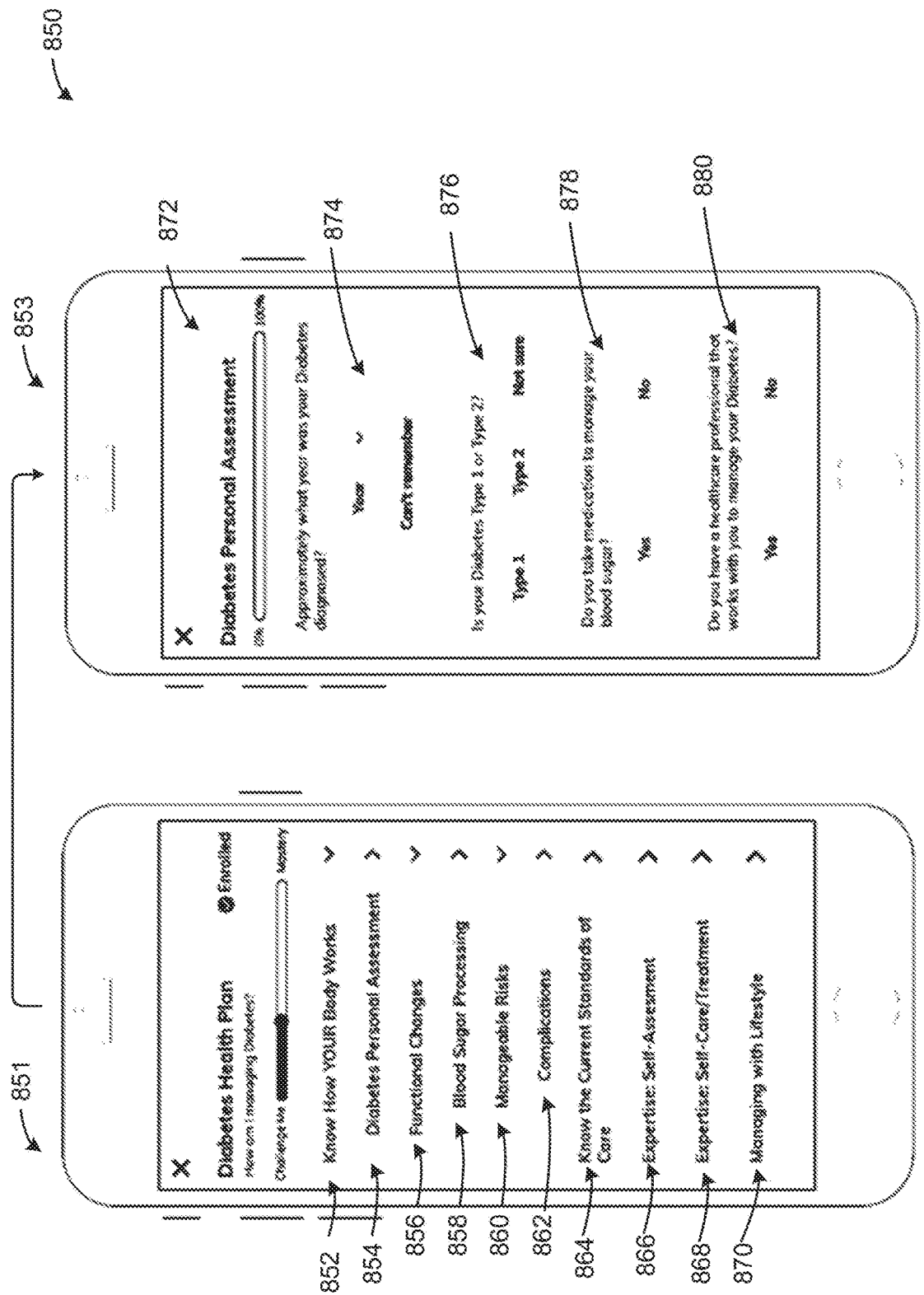

In FIG. 8B, the screenshot 851 is seen in response to the user's selection of Diabetes (element 824). Example elements displayed in screenshot 851 include: Know How YOUR Body Works (element 852); Know the Current Standards of Care (element 864); Expertise: Self-Assessment (element 866); Expertise: Self-Care/Treatment (element 868); and Managing with Lifestyle (element 870). Managing with Lifestyle (element 870) focuses and tracks actions and lifestyle actions that a user can engage in. As a user's daily routine helps to manage diabetes, managing the user's lifestyle is important. The cognitive agent 110 can align a user's respective health plan based on a health assessment at enrollment. In various embodiments, the cognitive agent 110 aligns the respective health plan with an interest of the user, a goal and priority of the user, and lifestyle factors of the user-including exercise, diet and nutrition, and stress reduction.

Each of these elements 852, 864, 866, 868, and 870 can display additional sub-elements depending on a selection of the user. For example, as shown in the screen shot 851, Know How YOUR Body Works (element 852) includes additional sub-elements: Diabetes Personal Assessment (854); and Functional Changes (856). Additional sub-elements under Functional Changes (856) include: Blood Sugar Processing (858) and Manageable Risks (860). Finally, the sub-element Manageable Risks (860) includes an additional sub-element Complications (862). For purposes of this example, the user selects the Diabetes Personal Assessment (854) and the screen shot 853 shows a GUI (872) associated with the Diabetes Personal Assessment.

The Diabetes Personal Assessment includes questions such as "Approximately what year was your Diabetes diagnosed" and corresponding elements a user can select to answer including "Year" and "Can't remember" (element 874). Additional questions include "Is your Diabetes Type 1 or Type 2" and corresponding answers selectable by a user include "Type 1," "Type 2," and "Not sure" (element 876). Another question includes "Do you take medication to manage your blood sugar" and corresponding answers selectable by a user include "Yes" and "No" (element 878). An additional question asks "Do you have a healthcare professional that works with you to manage your Diabetes" and corresponding answers selectable by the user include "Yes" and "No" (element 880).

In various embodiments, the cognitive intelligence platform 102 collects information about the user based on responses provided by the user or questions asked by the user as the user interacts with the GUI. For example, as the user views the screen shot 851, if the user asks if diabetes is curable, this question provides information about the user such as a level of education of the user.

Figure 8C:
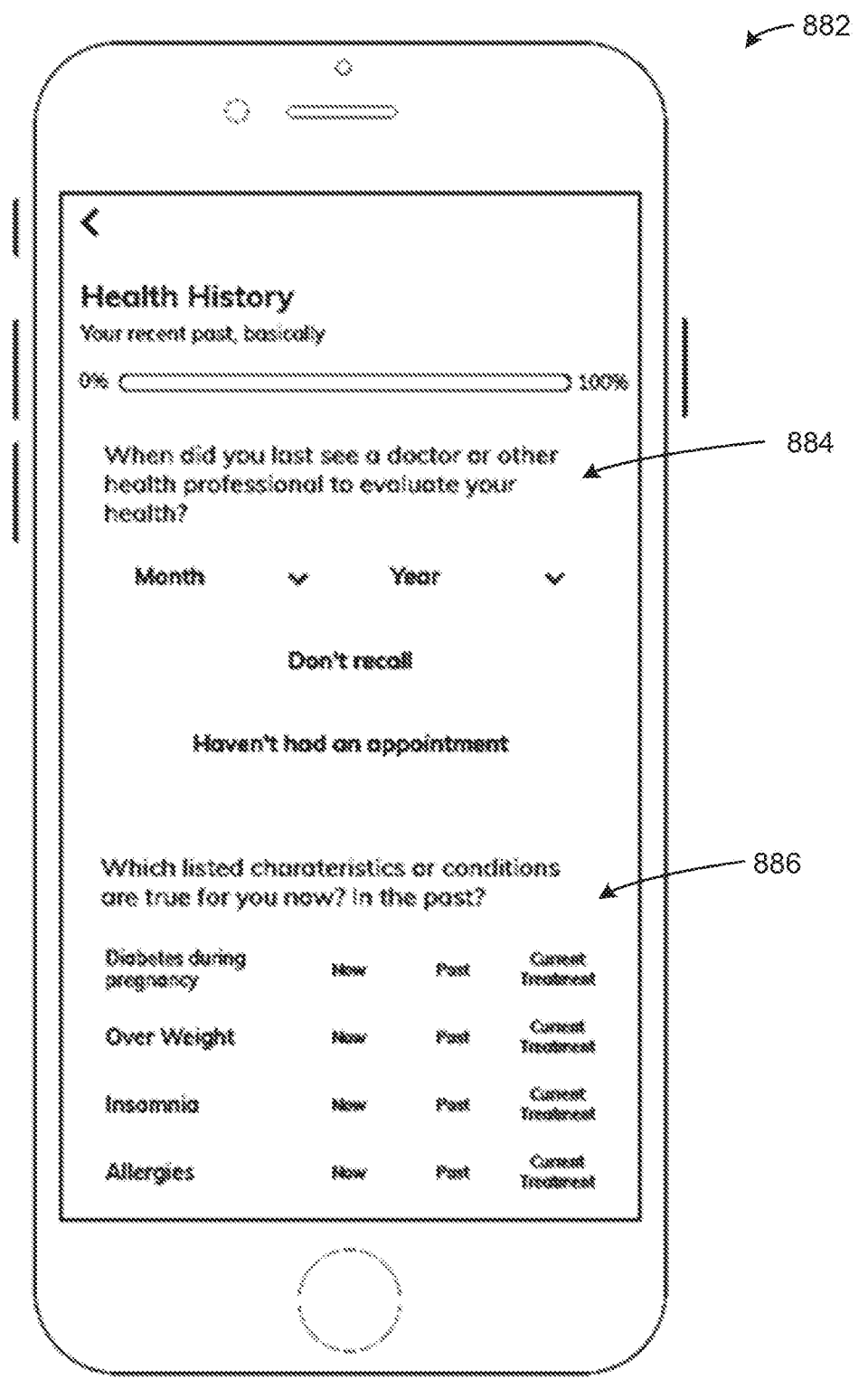

FIG. 8C illustrates aspects of an additional tool—e.g., a microsurvey—provided to the user that helps gather additional information about the user (e.g., available data). In various embodiments, a micro-survey represent a short targeted survey, where the questions presented in the survey are limited to a respective micro-theory. A microsurvey can be created by the cognitive intelligence platform 102 for several different purposes, including: completing a user profile, and informing a missing parameter during the process of answering an originating question.

In FIG. 8C, the microsurvey 882 gathers information related to health history, such as "when did you last see a doctor or other health professional to evaluate your health" where corresponding answers selectable by the user include specifying a month and year, "don't recall," and "haven't had an appointment" (element 884). An additional question asks "Which listed characteristics or conditions are true for you now? In the past?" where corresponding answers selectable by the user include "Diabetes during pregnancy," "Over Weight," "Insomnia," and "Allergies" (element 886). Each of the corresponding answer in element 886 also includes the option to indicate whether the characteristics or conditions are true for the user "Now", "Past," or "Current Treatment."

Figure 8D:
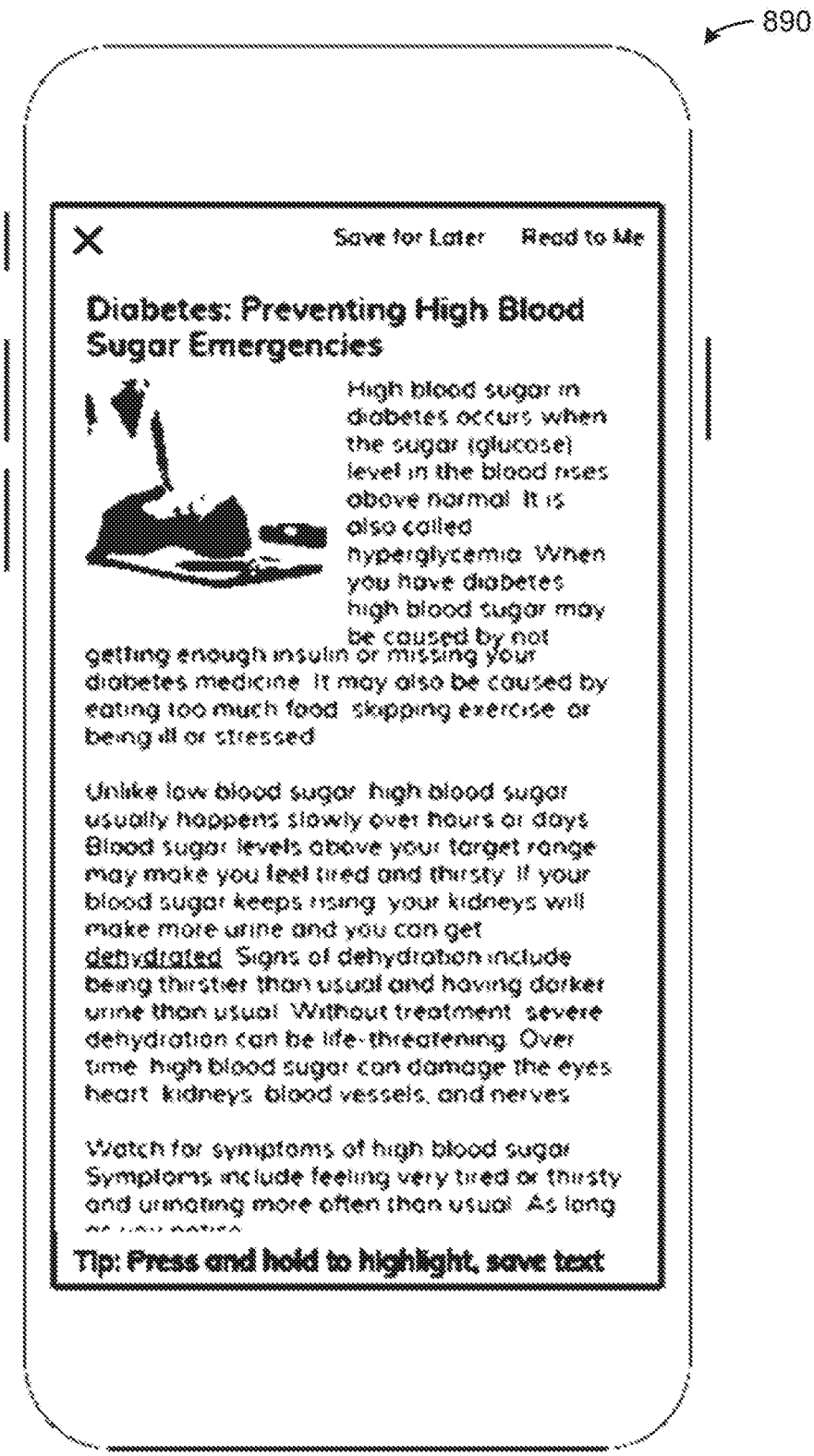

In FIG. 8D, aspects of educating a user are shown in the screen shot 890. The screen shot displays an article titled "Diabetes: Preventing High Blood Sugar Emergencies," and proceeds to describe when high blood sugar occurs and other information related to high blood sugar. The content displayed in the screen shot 890 is searchable and hearable as a podcast.

Accordingly, the cognitive agent 110 can answer a library of questions and provide content for many questions a user has as it related to diabetes. The information provided for purposes of educating a user is based on an overall health plan of the user, which is based on meta data analysis of interactions with the user, and an analysis of the education level of the user.

Figure 9A:
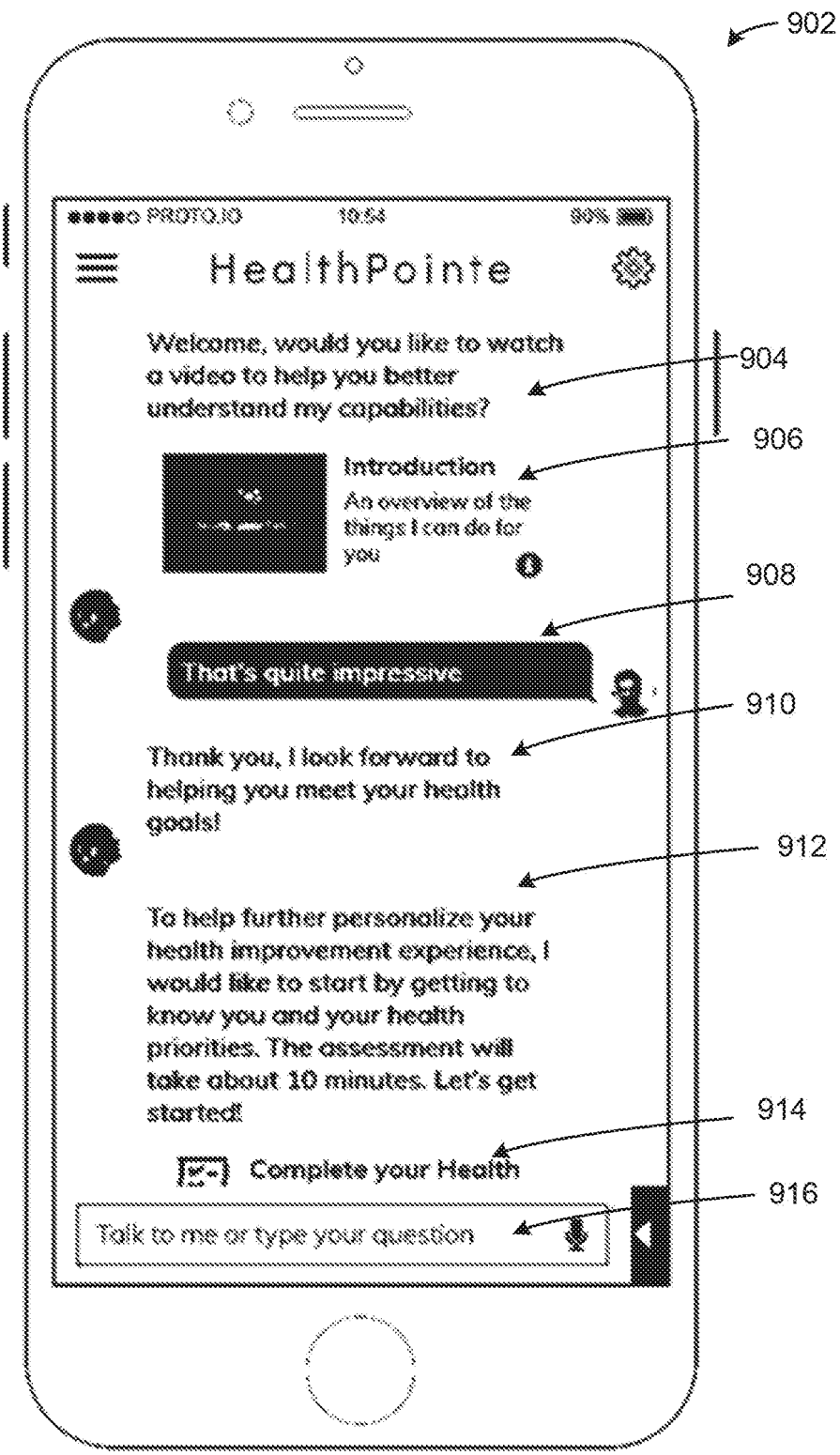
FIGS. 9A and 9B shows aspects of a conversational stream, in accordance with various embodiments.
Figure 9B:
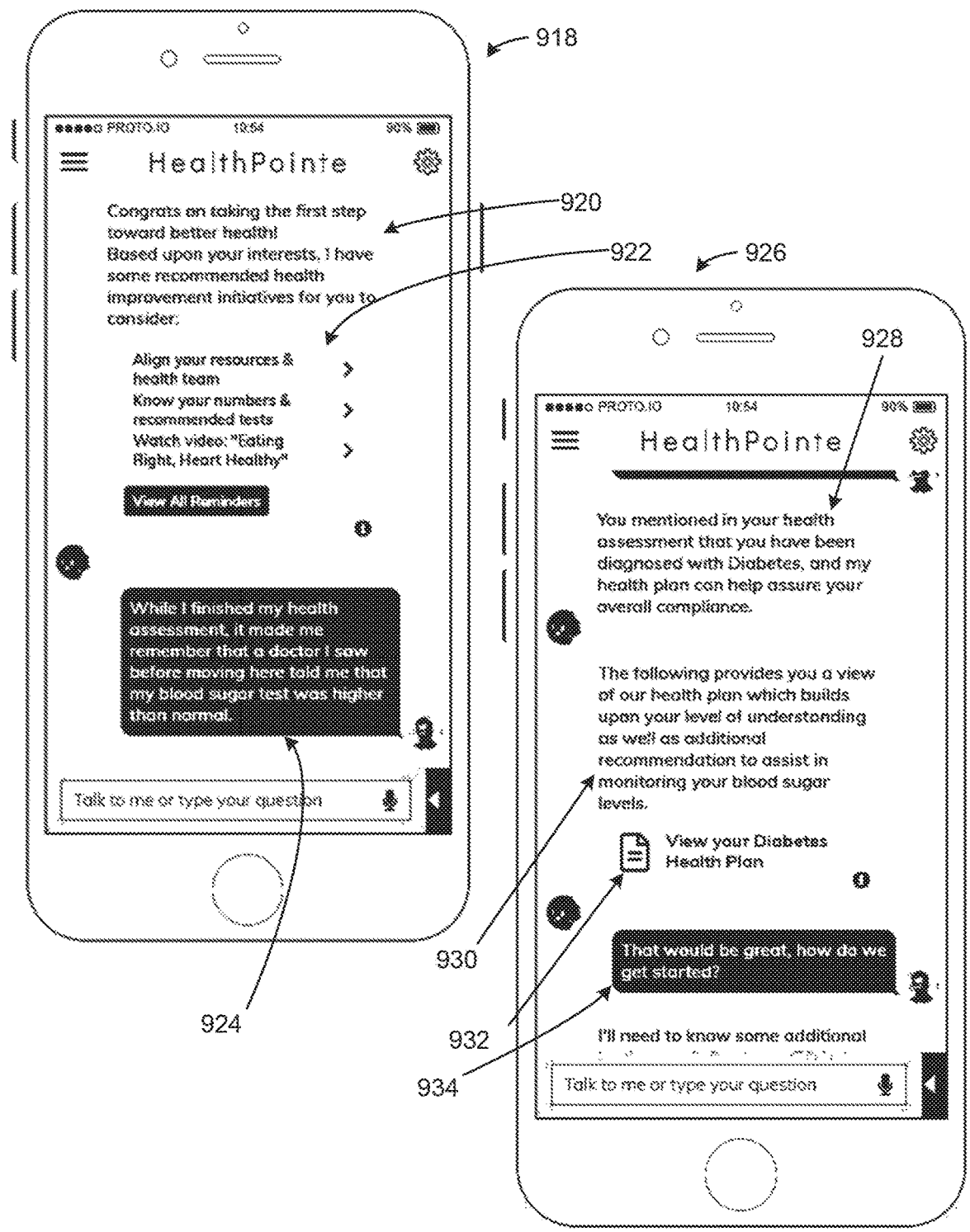

FIGS. 9A-9B illustrate aspects of a conversational stream, in accordance with various embodiments. In particular, FIG. 9A displays an example conversational stream between a user and the cognitive agent 110. The screen shot 902 is an example of a dialogue that unfolds between a user and the cognitive agent 110, after the user has registered with the cognitive intelligence platform 102. In the screen shot 902, the cognitive agent 110 begins by stating "Welcome, would you like to watch a video to help you better understand my capabilities" (element 904). The cognitive agent provides an option to watch the video (element 906). In response, the user inputs text "that's quite impressive" (element 908). In various embodiments, the user inputs text using the input box 916, which instructs the user to "Talk to me or type your question".

Next, the cognitive agent 110 says "Thank you. I look forward to helping you meet your health goals!" (element 910). At this point, the cognitive agent 110 can probe the user for additional data by offering a health assessment survey (e.g., a microsurvey) (element 914). The cognitive agent 110 prompts the user to fill out the health assessment by stating: "To help further personalize your health improvement experience, I would like to start by getting to know you and your health priorities. The assessment will take about 10 minutes. Let's get started!" (element 912).

In FIG. 9B, an additional conversational stream between the user and the cognitive agent 110 is shown. In this example conversational stream, the user previously completed a health assessment survey. The conversational stream can follow the example conversational stream discussed in FIG. 9A.

In the screen shot 918, the cognitive agent acknowledges the user's completion of the health assessment survey (element 920) and provides additional resources to the user (element 922). In element 920, the cognitive agent states: "Congrats on taking the first step toward better health! Based upon your interest, I have some recommended health improvement initiatives for you to consider," and presents the health improvement initiatives. In the example conversational stream, the user gets curious about a particular aspect of his health and states: "While I finished my health assessment, it made me remember that a doctor I saw before moving here told me that my blood sugar test was higher than normal." (element 924). After receiving the statement in element 924, the cognitive agent 110 treats the statement as an originating question and undergoes an initial round of analysis (and additional rounds of analysis as needed) as described above.

The cognitive agent 110 presents an answer as shown in screen shot 926. For example, the cognitive agent 110 states: "You mentioned in your health assessment that you have been diagnosed with Diabetes, and my health plan can help assure your overall compliance" (element 928). The cognitive agent further adds: "The following provides you a view of our health plan which builds upon your level of understanding as well as additional recommendations to assist in monitoring your blood sugar levels" (element 930). The cognitive agent 110 provides the user with the option to view his Diabetes Health Plan (element 932).

The user responds "That would be great, how do we get started" (element 934). The cognitive agent 110 receives the user's response as another originated question and undergoes an initial round of analysis (and additional rounds of analysis as needed) as described above. In the example screen shot 926, the cognitive agent 110 determines additional information is needed and prompts the user for additional information.

Figure 10:
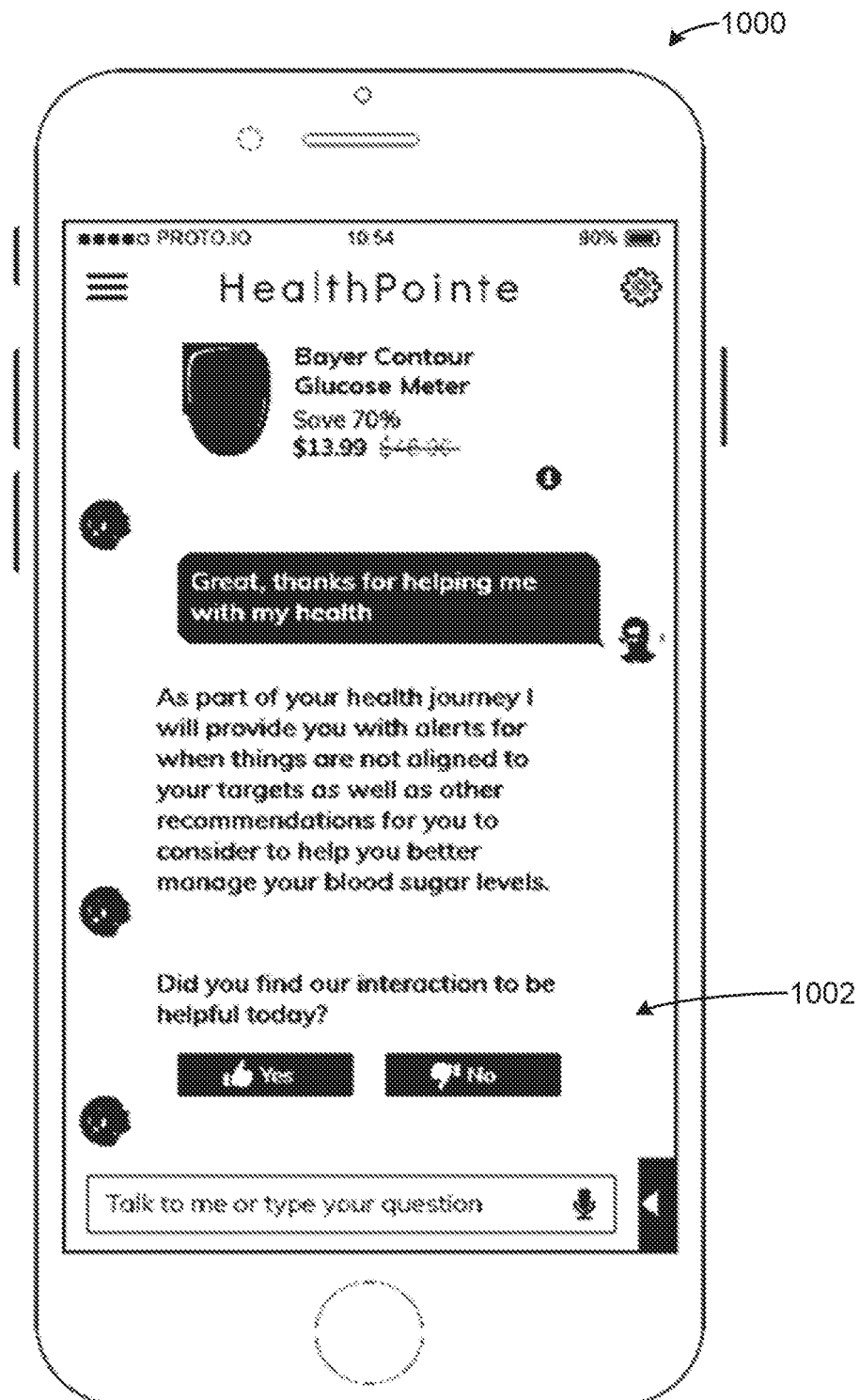
FIG. 10 shows aspects of a conversational stream, in accordance with various embodiments.

FIG. 10 illustrates an additional conversational stream, in accordance with various embodiments. In particular, in the screen shot 1000, the cognitive agent 110 elicit feedback (element 1002) to determine whether the information provided to the user was useful to the user.

Figure 11:
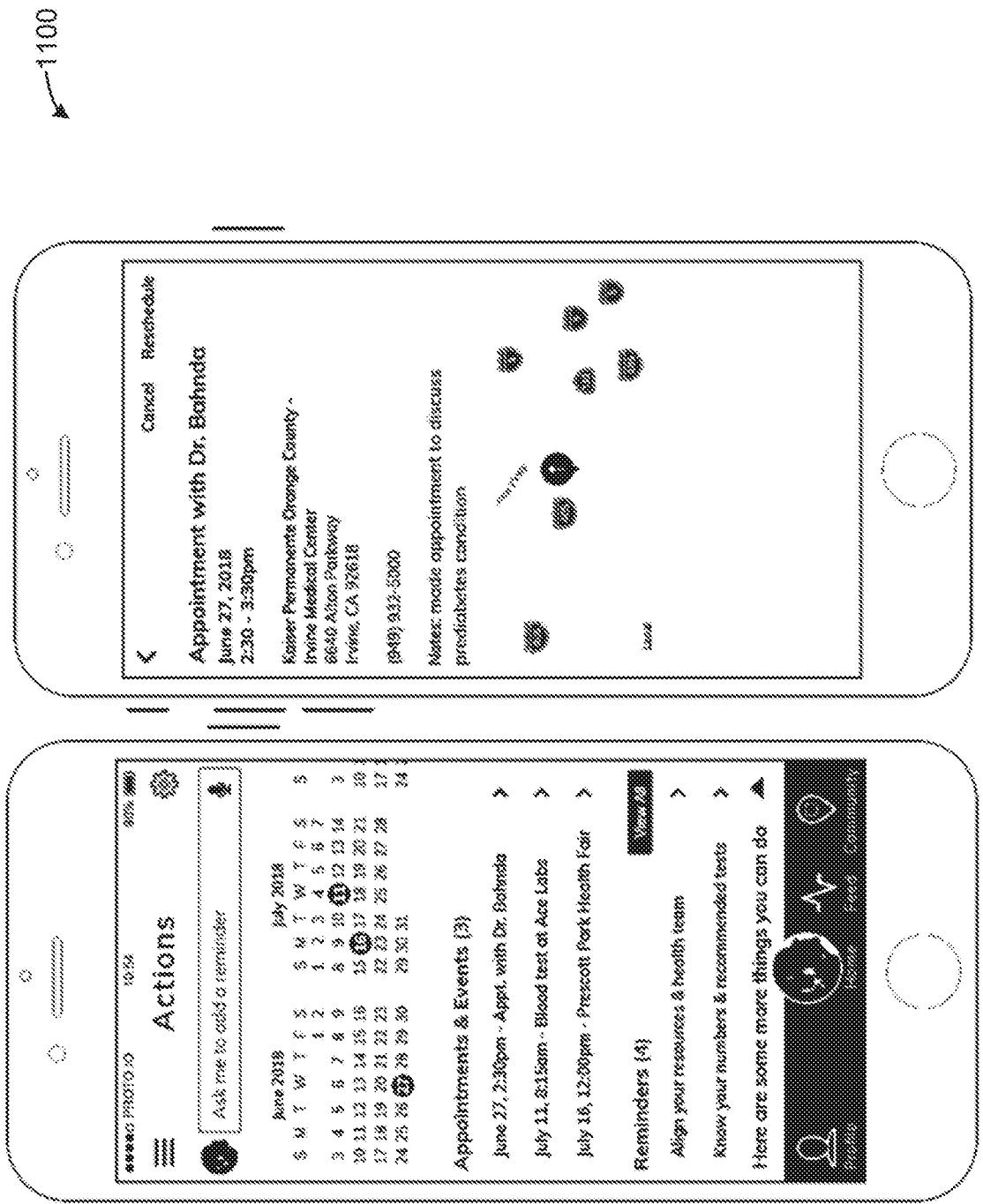
FIG. 11 shows aspects of an action calendar, in accordance with various embodiments.

FIG. 11 illustrates aspects of an action calendar, in accordance with various embodiments. The action calendar is managed through the conversational stream between the cognitive agent 110 and the user. The action calendar aligns to care and wellness protocols, which are personalized to the risk condition or wellness needs of the user. The action calendar is also contextually aligned (e.g., what is being required or searched by the user) and hyper local (e.g., aligned to events and services provided in the local community specific to the user).

Figure 12:
FIG. 12 shows aspects of a feed, in accordance with various embodiments.

FIG. 12 illustrates aspects of a feed, in accordance with various embodiments. The feed allows a user to explore new opportunities and celebrate achieving goals (e.g., therapeutic or wellness goals). The feed provides a searchable interface (element 1202).

The feed provides an interface where the user accesses a personal log of activities the user is involved in. The personal log is searchable. For example, if the user reads an article recommended by the cognitive agent 110 and highlights passages, the highlighted passages are accessible through the search. Additionally, the cognitive agent 110 can initiate a conversational stream focused on subject matter related to the highlighted passages.

The feed provides an interface to celebrate mini achievements and successes in the user's personal goals (e.g., therapeutic or wellness goals). In the feed, the cognitive agent 110 is still available (ribbon 1204) to help search, guide, or steer the user toward a therapeutic or wellness goal.

Figure 13:
FIG. 13 shows aspects of a hyper-local community, in accordance with various embodiments.

FIG. 13 illustrates aspects of a hyper-local community, in accordance with various embodiments. A hyper-local community is a digital community that is health and wellness focused and encourages the user to find opportunities for themselves and get involved in a community that is physically close to the user. The hyper-local community allows a user to access a variety of care and wellness resources within his community and example recommendations include: Nutrition; Physical Activities; Healthcare Providers; Educations; Local Events; Services; Deals and Stores; Charities; and Products offered within the community. The cognitive agent 110 optimizes suggestions which help the user progress towards a goal as opposed to providing open ended access to hyper-local assets. The recommendations are curated and monitored for relevance to the user, based on the user's goals and interactions between the user and the cognitive agent 110.

Accordingly, the cognitive intelligence platform provides several core features including:

1) the ability to identify an appropriate action plan using narrative style interactions that generates data that includes intent and causation and using narrative style interactions;

2) monitoring: integration of offline to online clinical results across the functional medicine clinical standards;

3) the knowledge cloud that includes a comprehensive knowledge base of thousands of health related topics, an educational guide to better health aligned to western and eastern culture;

4) coaching using artificial intelligence; and 5) profile and health store that offers a holistic profile of each consumers health risks and interactions, combined with a repository of services, products, lab tests, devices, deals, supplements, pharmacy & telemedicine.

Figure 14:
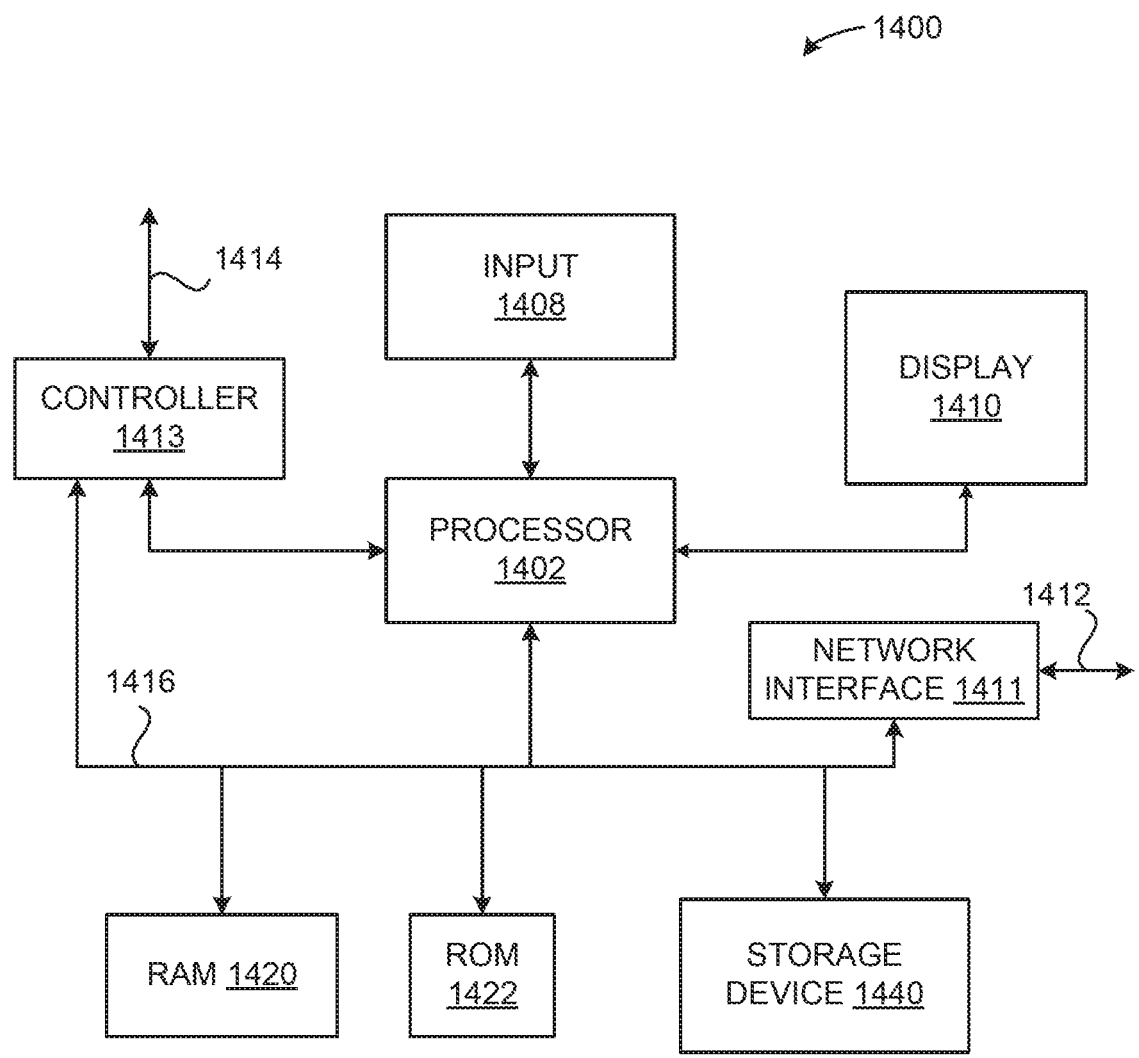
FIG. 14 illustrates a detailed view of a computing device that can represent the computing devices of FIG. 1 used to implement the various platforms and techniques described herein, according to some embodiments.

FIG. 14 illustrates a detailed view of a computing device 1400 that can be used to implement the various components described herein, according to some embodiments. In particular, the detailed view illustrates various components that can be included in the user device 104 illustrated in FIG. 1, as well as the several computing devices implementing the cognitive intelligence platform 102. As shown in FIG. 14, the computing device 1400 can include a processor 1402 that represents a microprocessor or controller for controlling the overall operation of the computing device 1400. The computing device 1400 can also include a user input device 1408 that allows a user of the computing device 1400 to interact with the computing device 1400. For example, the user input device 1408 can take a variety of forms, such as a button, keypad, dial, touch screen, audio input interface, visual/image capture input interface, input in the form of sensor data, and so on. Still further, the computing device 1400 can include a display 1410 that can be controlled by the processor 1402 to display information to the user. A data bus 1416 can facilitate data transfer between at least a storage device 1440, the processor 1402, and a controller 1413. The controller 1413 can be used to interface with and control different equipment through an equipment control bus 1414. The computing device 1400 can also include a network/bus interface 1411 that couples to a data link 1412. In the case of a wireless connection, the network/bus interface 1411 can include a wireless transceiver.

As noted above, the computing device 1400 also includes the storage device 1440, which can comprise a single disk or a collection of disks (e.g., hard drives), and includes a storage management module that manages one or more partitions within the storage device 1440. In some embodiments, storage device 1440 can include flash memory, semiconductor (solid-state) memory or the like. The computing device 1400 can also include a Random-Access Memory (RAM) 1420 and a Read-Only Memory (ROM) 1422. The ROM 1422 can store programs, utilities or processes to be executed in a non-volatile manner. The RAM 1420 can provide volatile data storage, and stores instructions related to the operation of processes and applications executing on the computing device.

Figure 15:
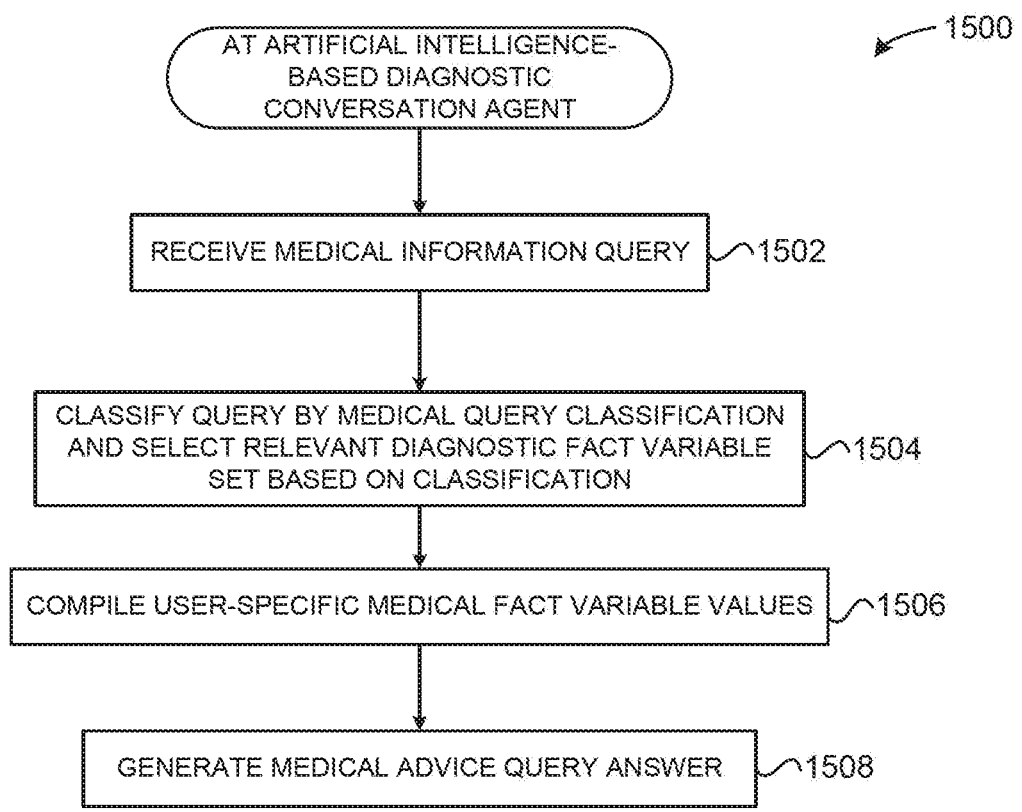
FIG. 15 shows a method, in accordance with various embodiments.

FIG. 15 shows a method (1500), in accordance with various embodiments, for answering a user-generated natural language medical information query based on a diagnostic conversational template.

In the method as shown in FIG. 15, an artificial intelligence-based diagnostic conversation agent receives a user-generated natural language medical information query as entered by a user through a user interface on a computer device (FIG. 15, block 1502). In some embodiments, the artificial intelligence-based diagnostic conversation agent is the conversation agent 110 of FIG. 1. In some embodiments the computer device is the mobile device 104 of FIG. 1. One example of a user-generated natural language medical information query as entered by a user through a user interface is the question "Is a blood sugar of 90 normal?" as shown in line 402 of FIG. 4. In some embodiments, receiving a user-generated natural language medical information query as entered by a user through a user interface on a computer device (FIG. 15, block 1502) is Step 1 as earlier discussed in the context of "Analyzing Conversational Context As Part of Conversational Analysis".

In response to the user-generated natural language medical information query, the artificial intelligence-based diagnostic conversation agent selects a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504). In some embodiments, the artificial intelligence-based diagnostic conversation agent selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504) is accomplished through one or more of Steps 2-6 as earlier discussed in the context of "Analyzing Conversational Context As Part of Conversational Analysis".

FIG. 15 further shows compiling user-specific medical fact variable values for one or more respective medical fact variables of the diagnostic fact variable set (FIG. 15, block 1506). Compiling user-specific medical fact variable values for one or more respective medical fact variables of the diagnostic fact variable set (FIG. 15, block 1506) may include one or more of Steps 2-6 as earlier discussed in the context of "Analyzing Conversational Context As Part of Conversational Analysis".

In response to the user-specific medical fact variable values, the artificial intelligence-based diagnostic conversation agent generates a medical advice query answer in response to the user-generated natural language medical information query (FIG. 15, block 1508). In some embodiments, this is Step 7 as earlier discussed in the context of "Analyzing Conversational Context As Part of Conversational Analysis".

In some embodiments, compiling user-specific medical fact variable values (FIG. 15, block 1506) includes extracting a first set of user-specific medical fact variable values from a local user medical information profile associated with the user-generated natural language medical information query and requesting a second set of user specific medical fact variable values through natural-language questions sent to the user interface on the mobile device (e.g. the microsurvey data 206 of FIG. 2 that came from the microsurvey 116 of FIG. 1). The local user medical information profile can be the profile as generated in FIG. 7A at block 708.

In some embodiments, compiling user-specific medical fact variable values (FIG. 15, block 1506) includes extracting a third set of user-specific medical fact variable values that are lab result values from the local user medical information profile associated with the user generated natural language medical information query. The local user medical information profile can be the profile as generated in FIG. 7A at block 708.

In some embodiments, compiling user-specific medical fact variable values (FIG. 15, block 1506) includes extracting a fourth set of user-specific medical variable values from a remote medical data service profile associated with the local user medical information profile. The remote medical data service profile can be the service provider data 202 of FIG. 2, which can come from the service provider 112 of FIG. 1. The local user medical information profile can be the profile as generated in FIG. 7A at block 708.

In some embodiments, compiling user-specific medical fact variable values (FIG. 15, block 1506) includes extracting a fifth set of user-specific medical variable values from demographic characterizations provided by a remote data service analysis of the local user medical information profile. The remote demographic characterizations can be the service provider data 202 of FIG. 2, which can come from the service provider 112 of FIG. 1. The local user medical information profile can be the profile as generated in FIG. 7A at block 708.

In some embodiments, generating the medical advice query answer (FIG. 15, block 1508) includes providing a treatment action-item recommendation in response to user-specific medical fact values that may be non-responsive to the medical question presented in the user-generated natural language medical information query. Such an action could define an action plan based on the data compiled (FIG. 15, block 1506), as shown in FIG. 7C, block 758.

In some embodiments, generating the medical advice query answer (FIG. 15, block 1506) includes providing a medical education media resource in response to user-specific medical fact variable values that may be non-responsive to the medical question presented in the user-generated natural language medical information query. Such an action could serve to educate and inform the user, as in block 758 of FIG. 7C.

In some embodiments, selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504) includes classifying the user-generated natural language medical information query into one of a set of domain-directed medical query classifications based on relevance to the local user medical information profile associated with the user-generated natural language medical information query. The local user medical information profile can be the profile as generated in FIG. 7A at block 708.

In some embodiments, the method (1500) for answering a user-generated natural language medical information query based on a diagnostic conversational template is implemented as a computer program product in a computer-readable medium.

In some embodiments, the system and method 1500 shown in FIG. 15 and described above is implemented on the computing device 1400 shown in FIG. 14.

Figure 16:
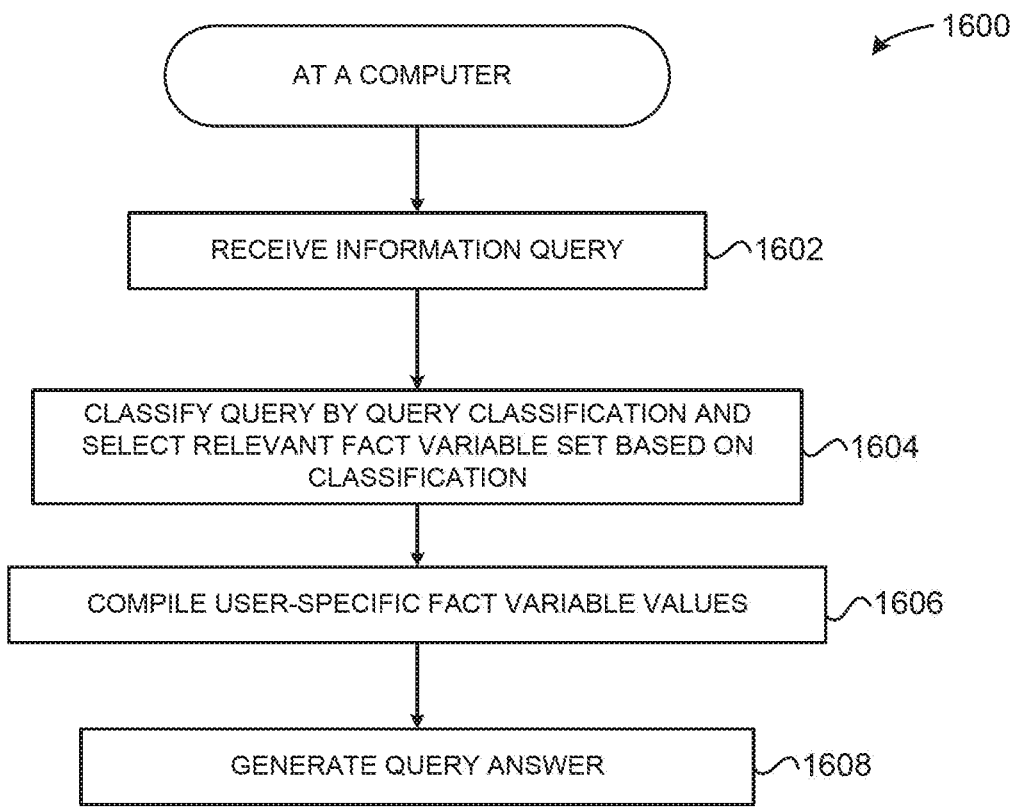
FIG. 16 shows a method, in accordance with various embodiments.

FIG. 16 shows a method (1600), in accordance with various embodiments, for answering a user-generated natural language query based on a conversational template.

In the method as shown in FIG. 16, an artificial intelligence-based conversation agent receives a user-generated natural language query as entered by a user through a user interface (FIG. 16, block 1602). In some embodiments, the artificial intelligence-based conversation agent is the conversation agent 110 of FIG. 1. In some embodiments, the user interface is on a computer device. In some embodiments the computer device is the mobile device 104 of FIG. 1. One example of a user-generated natural language query as entered by a user through a user interface is the question "Is a blood sugar of 90 normal?" as shown in line 402 of FIG. 4. In some embodiments, receiving a user-generated natural language query as entered by a user through a user interface on a computer device (FIG. 16, block 1602) is Step 1 as earlier discussed in the context of "Analyzing Conversational Context As Part of Conversational Analysis".

In response to the user-generated natural language query, the artificial intelligence-based conversation agent selects a fact variable set relevant to generating a query answer for the user-generated natural language query by classifying the user-generated natural language query into one of a set of domain-directed query classifications associated with respective fact variable sets (FIG. 16, block 1604). In some embodiments, the artificial intelligence-based conversation agent selecting a fact variable set relevant to generating a query answer for the user-generated natural language query by classifying the user-generated natural language query into one of a set of domain-directed query classifications associated with respective fact variable sets (FIG. 16, block 1604) is accomplished through one or more of Steps 2-6 as earlier discussed in the context of "Analyzing Conversational Context As Part of Conversational Analysis".

FIG. 16 further shows compiling user-specific variable values for one or more respective fact variables of the fact variable set (FIG. 16, block 1606). Compiling user-specific fact variable values for one or more respective fact variables of the fact variable set (FIG. 16, block 1606) may include one or mor of Steps 2-6 as earlier discussed in the context of "Analyzing Conversational Context As Part of Conversational Analysis".

In response to the user-specific fact variable values, the artificial intelligence-based conversation agent generates a query answer in response to the user-generated natural language query (FIG. 16, block 1608). In some embodiments, this is Step 7 as earlier discussed in the context of "Analyzing Conversational Context As Part of Conversational Analysis".

In some embodiments, compiling user-specific fact variable values (FIG. 16, block 1606) includes extracting a first set of user-specific fact variable values from a local user profile associated with the user-generated natural language query and requesting a second set of user specific variable values through natural-language questions sent to the user interface on the mobile device (e.g. the microsurvey data 206 of FIG. 2 that came from the microsurvey 116 of FIG. 1). The local user profile can be the profile as generated in FIG. 7A at block 708. In some embodiments, the natural language questions sent to the user interface on the mobile device can be a part of a conversation template.

In some embodiments, compiling user-specific fact variable values (FIG. 16, block 1606) includes extracting a third set of user-specific fact variable values that are test result values from the local user profile associated with the user generated natural language query. The local user profile can be the profile as generated in FIG. 7A at block 708. In some embodiments, compiling user-specific fact variable values (FIG. 16, block 1606) includes extracting a fourth set of user-specific variable values from a remote data service profile associated with the local user profile. The remote data service profile can be the service provider data 202 of FIG. 2, which can come from the service provider 112 of FIG. 1. The local user profile can be the profile as generated in FIG. 7A at block 708.

In some embodiments, compiling user-specific fact variable values (FIG. 16, block 1606) includes extracting a fifth set of user-specific variable values from demographic characterizations provided by a remote data service analysis of the local user profile. The remote demographic characterizations can be the service provider data 202 of FIG. 2, which can come from the service provider 112 of FIG. 1. The local user profile can be the profile as generated in FIG. 7A at block 708.

In some embodiments, generating the query answer (FIG. 16, block 1608) includes providing a action-item recommendation in response to user-specific fact values that may be non-responsive to the question presented in the user-generated natural language query. Such an action could define an action plan based on the data compiled (FIG. 16, block 1606), as shown in FIG. 7C, block 758.

In some embodiments, generating the advice query answer (FIG. 16, block 1606) includes providing a education media resource in response to user-specific fact variable values that may be non-responsive to the question presented in the user-generated natural language query. Such an action could serve to educate and inform the user, as in block 758 of FIG. 7C.

In some embodiments, selecting a fact variable set relevant to generating a query answer for the user-generated natural language query by classifying the user-generated natural language query into one of a set of domain-directed query classifications associated with respective fact variable sets (FIG. 16, block 1604) includes classifying the user-generated natural language query into one of a set of domain-directed query classifications based on relevance to the local user profile associated with the user-generated natural language query. The local user profile can be the profile as generated in FIG. 7A at block 708.

In some embodiments, the method (1600) for answering a user-generated natural language query based on a conversational template is implemented as a computer program product in a computer-readable medium.

In some embodiments, the system and method shown in FIG. 16 and described above is implemented in the cognitive intelligence platform 102 shown in FIG. 1.

In the cognitive intelligence platform 102, a cognitive agent 110 is configured for receiving a user-generated natural language query at an artificial intelligence-based conversation agent from a user interface on a user device 104 (FIG. 16, block 1602).

A critical thinking engine 108 is configured for, responsive to content of the user-generated natural language query, selecting a fact variable set relevant to generating a query answer for the user-generated natural language query by classifying the user-generated natural language query into one of a set of domain-directed query classifications associated with respective fact variable sets (FIG. 16, block 1604).

Included is a knowledge cloud 106 that compiles user-specific fact variable values for one or more respective fact variables of the fact variable set (FIG. 16, block 1606).

Responsive to the fact variable values, the cognitive agent 110 is further configured for generating the query answer in response to the user-generated natural language query (FIG. 16, block 1606).

In some embodiments, the system and method 1600 shown in FIG. 16 and described above is implemented on the computing device 1400 shown in FIG. 14.

Figure 17:
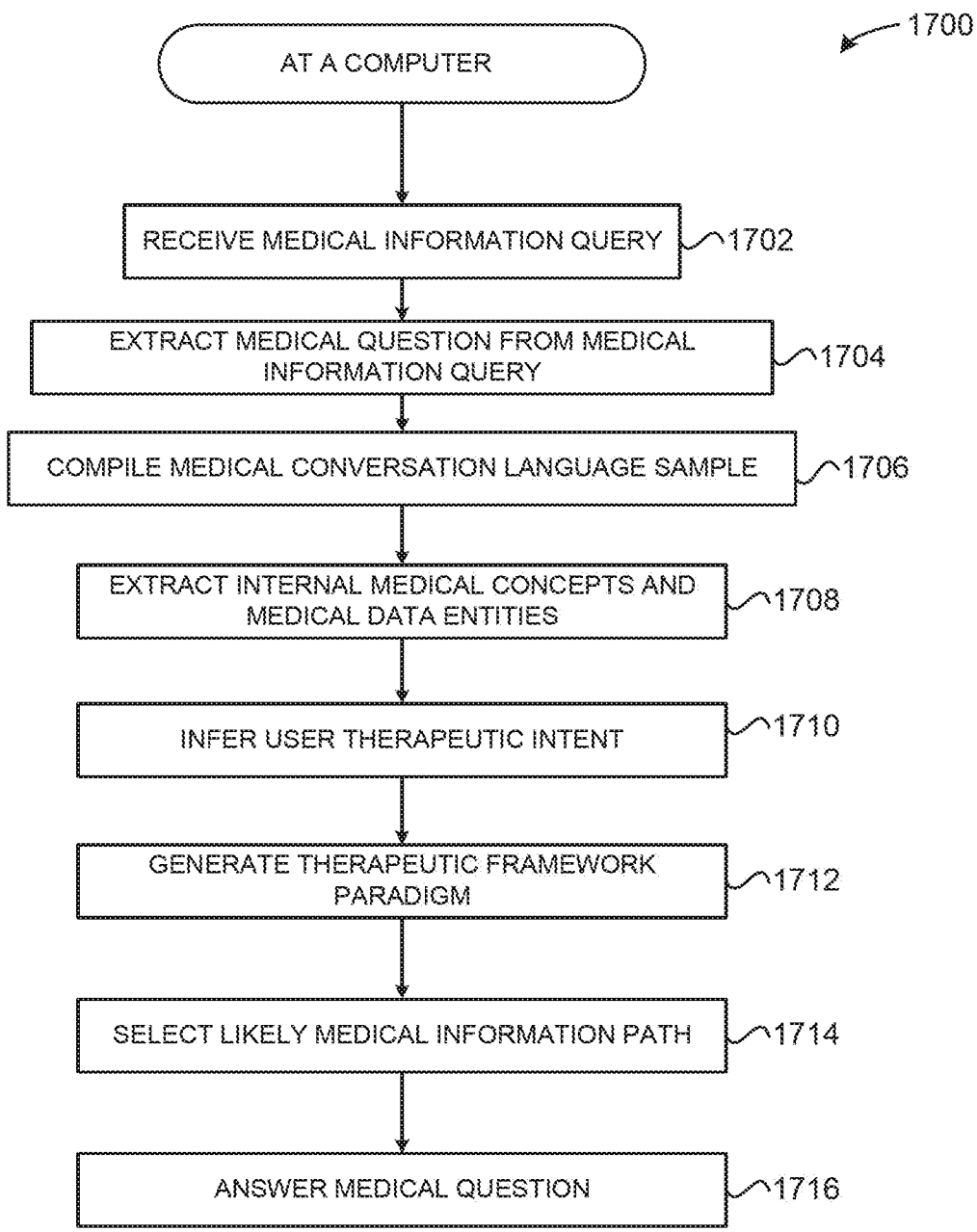
FIG. 17 shows a method, in accordance with various embodiments.

FIG. 17 shows a computer-implemented method 1700 for answering natural language medical information questions posed by a user of a medical conversational interface of a cognitive artificial intelligence system. In some embodiments, the method 1700 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14.

The method 1700 involves receiving a user-generated natural language medical information query from a medical conversational user interface at an artificial intelligence-based medical conversation cognitive agent (block 1702). In some embodiments, receiving a user-generated natural language medical information query from a medical conversational user interface at an artificial intelligence-based medical conversation cognitive agent (block 1702) is performed by a cognitive agent that is a part of the cognitive intelligence platform and is configured for this purpose. In some embodiments, the artificial intelligence-based diagnostic conversation agent is the conversation agent 110 of FIG. 1. One example of a user-generated natural language medical information query is "Is a blood sugar of 90 normal?" as shown in line 402 of FIG. 4. In some embodiments, the user interface is on the mobile device 104 of FIG. 1. In some embodiments, receiving a user-generated natural language medical information query from a medical conversational user interface at an artificial intelligence-based medical conversation cognitive agent (block 1702) is Step 1 as earlier discussed in the context of "Analyzing Conversational Context As Part of Conversational Analysis".

The method 1700 further includes extracting a medical question from a user of the medical conversational user interface from the user-generated natural language medical information query (block 1704). In some embodiments, extracting a medical question from a user of the medical conversational user interface from the user-generated natural language medical information query (block 1704) is performed by a critical thinking engine configured for this purpose. In some embodiments, the critical thinking engine is the critical thinking engine 108 of FIG. 1. In some embodiments, extracting a medical question from a user of the medical conversational user interface from the user-generated natural language medical information query (block 1704) is accomplished through one or more of Steps 2-6 as earlier discussed in the context of "Analyzing Conversational Context As Part of Conversational Analysis".

The method 1700 includes compiling a medical conversation language sample (block 1706). In some embodiments, compiling a medical conversation language sample (block 1706) is performed by a critical thinking engine configured for this purpose. In some embodiments, the critical thinking engine is the critical thinking engine 108 of FIG. 1. The medical conversation language sample can include items of health-information-related-text derived from a health-related conversation between the artificial intelligence-based medical conversation cognitive agent and the user. In some embodiments compiling a medical conversation language sample (block 1706) is accomplished through one or more of Steps 2-6 as earlier discussed in the context of "Analyzing Conversational Context As Part of Conversational Analysis".

The method 1700 involves extracting internal medical concepts and medical data entities from the medical conversation language sample (block 1708). In some embodiments, extracting internal medical concepts and medical data entities from the medical conversation language sample (block 1708) is performed by a critical thinking engine configured for this purpose. In some embodiments, the critical thinking engine is the critical thinking engine 108 of FIG. 1. The internal medical concepts can include descriptions of medical attributes of the medical data entities. In some embodiments, extracting internal medical concepts and medical data entities from the medical conversation language sample (block 1708) is accomplished through one or more of Steps 2-6 as earlier discussed in the context of "Analyzing Conversational Context As Part of Conversational Analysis".

The method 1700 involves inferring a therapeutic intent of the user from the internal medical concepts and the medical data entities (block 1710). In some embodiments, inferring a therapeutic intent of the user from the internal medical concepts and the medical data entities (block 1710) is performed by a critical thinking engine configured for this purpose. In some embodiments, the critical thinking engine is the critical thinking engine 108 of FIG. 1. In some embodiments, inferring a therapeutic intent of the user from the internal medical concepts and the medical data entities (block 1710) is accomplished as in Step 2 as earlier discussed in the context of "Analyzing Conversational Context As Part of Conversational Analysis".

The method 1700 includes generating a therapeutic paradigm logical framework 1800 for interpreting of the medical question (block 1712). In some embodiments, generating a therapeutic paradigm logical framework 1800 for interpreting of the medical question (block 1712) is performed by a critical thinking engine configured for this purpose. In some embodiments, the critical thinking engine is the critical thinking engine 108 of FIG. 1. In some embodiments, generating a therapeutic paradigm logical framework 1800 for interpreting of the medical question (block 1712) is accomplished as in Step 5 as earlier discussed in the context of "Analyzing Conversational Context As Part of Conversational Analysis".

Figure 18:
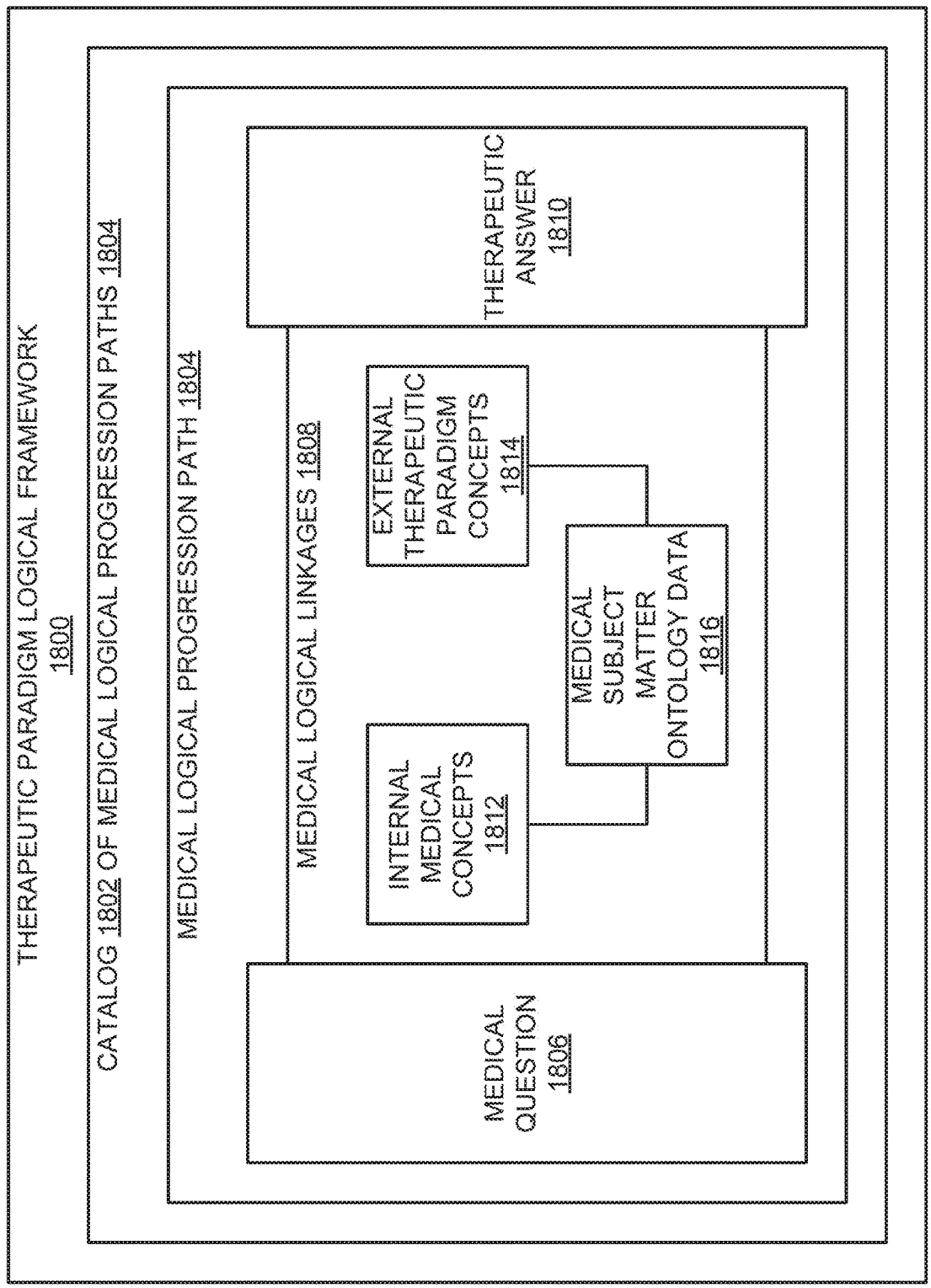
FIG. 18 shows a therapeutic paradigm logical framework, in accordance with various embodiments

FIG. 18 shows an example therapeutic paradigm logical framework 1800. The therapeutic paradigm logical framework 1800 includes a catalog 1802 of medical logical progression paths 1804 from the medical question 1806 to respective therapeutic answers 1810.

Each of the medical logical progression paths 1804 can include one or more medical logical linkages 1808 from the medical question 1806 to a therapeutic path-specific answer 1810.

The medical logical linkages 1808 can include the internal medical concepts 1812 and external therapeutic paradigm concepts 1814 derived from a store of medical subject matter ontology data 1816. In some embodiments, the store of subject matter ontology data 1816 is contained in a knowledge cloud. In some embodiments, the knowledge cloud is the knowledge cloud 102 of FIGS. 1 and 2. In some embodiments, the subject matter ontology data 1816 is the subject matter ontology data 216 of FIG. 2. In some embodiments, the subject matter ontology data 1816 includes the subject matter ontology 300 of FIG. 3.

The method 1700 shown in FIG. 17 further includes selecting a likely medical information path from among the medical logical progression paths 1804 to a likely path-dependent medical information answer based at least in part upon the therapeutic intent of the user (block 1714). In some embodiments, selecting a likely medical information path from among the medical logical progression paths 1804 to a likely path-dependent medical information answer based at least in part upon the therapeutic intent of the user (block 1714 is performed by a critical thinking engine configured for this purpose. In some embodiments, the critical thinking engine is the critical thinking engine 108 of FIG. 1. The selection can also be based in part upon the sufficiency of medical diagnostic data to complete the medical logical linkages 1808. In some embodiments, selection can also be based in part upon the sufficiency of medical diagnostic data to complete the medical logical linkages 1808 can be performed by a critical thinking engine that is further configured for this purpose. In some embodiments, the critical thinking engine is the critical thinking engine 108 of FIG. 1. The medical diagnostic data can include user-specific medical diagnostic data. The selection can also be based in part upon treatment sub-intents including tactical constituents related to the therapeutic intent of the user by the store of medical subject matter ontology data 1816. In some embodiments, selection based in part upon treatment sub-intents including tactical constituents related to the therapeutic intent of the user by the store of medical subject matter ontology data 1816 can be performed by a critical thinking engine further configured for this purpose. In some embodiments, the critical thinking engine is the critical thinking engine 108 of FIG. 1. The selection can further occur after requesting additional medical diagnostic data from the user. An example of requesting additional medical diagnostic data from the user is shown in FIG. 4 on line 406 "I need some additional information in order to answer this question, was this an in-home glucose test or was it done by a lab or testing service". In some embodiments, the process of selection after requesting additional medical diagnostic data from the user can be performed by a critical thinking engine further configured for this purpose. In some embodiments, the critical thinking engine is the critical thinking engine 108 of FIG. 1. In some embodiments, selecting a likely medical information path from among the medical logical progression paths 1804 to a likely path-dependent medical information answer based at least in part upon the therapeutic intent of the user (block 1714) is accomplished through one or more of Steps 5-6 as earlier discussed in the context of "Analyzing Conversational Context As Part of Conversational Analysis".

The method 1700 involves answering the medical question by following the likely medical information path to the likely path-dependent medical information answer (block 1716). In some embodiments, answering the medical question by following the likely medical information path to the likely path-dependent medical information answer (block 1716) is performed by a critical thinking engine configured for this purpose. In some embodiments, the critical thinking engine is the critical thinking engine 108 of FIG. 1. In some embodiments, answering the medical question by following the likely medical information path to the likely path-dependent medical information answer (block 1716) is accomplished as in Step 7 as earlier discussed in the context of "Analyzing Conversational Context As Part of Conversational Analysis".

The method 1700 can further include relating medical inference groups of the internal medical concepts. In some embodiments, relating medical inference groups of the internal medical concepts is performed by a critical thinking engine further configured for this purpose. In some embodiments, the critical thinking engine is the critical thinking engine 108 of FIG. 1. Relating medical inference groups of the internal medical concepts can be based at least in part on shared medical data entities for which each internal medical concept of a medical inference group of internal medical concepts describes a respective medical data attribute. In some embodiments, relating medical inference groups of the internal medical concepts based at least in part on shared medical data entities for which each internal medical concept of a medical inference group of internal medical concepts describes a respective medical data attribute can be performed by a critical thinking engine further configured for this purpose. In some embodiments, the critical thinking engine is the critical thinking engine 108 of FIG. 1.

In some embodiments, the method 1700 of FIG. 17 is implemented as a computer program product in a computer-readable medium.

Figure 19:
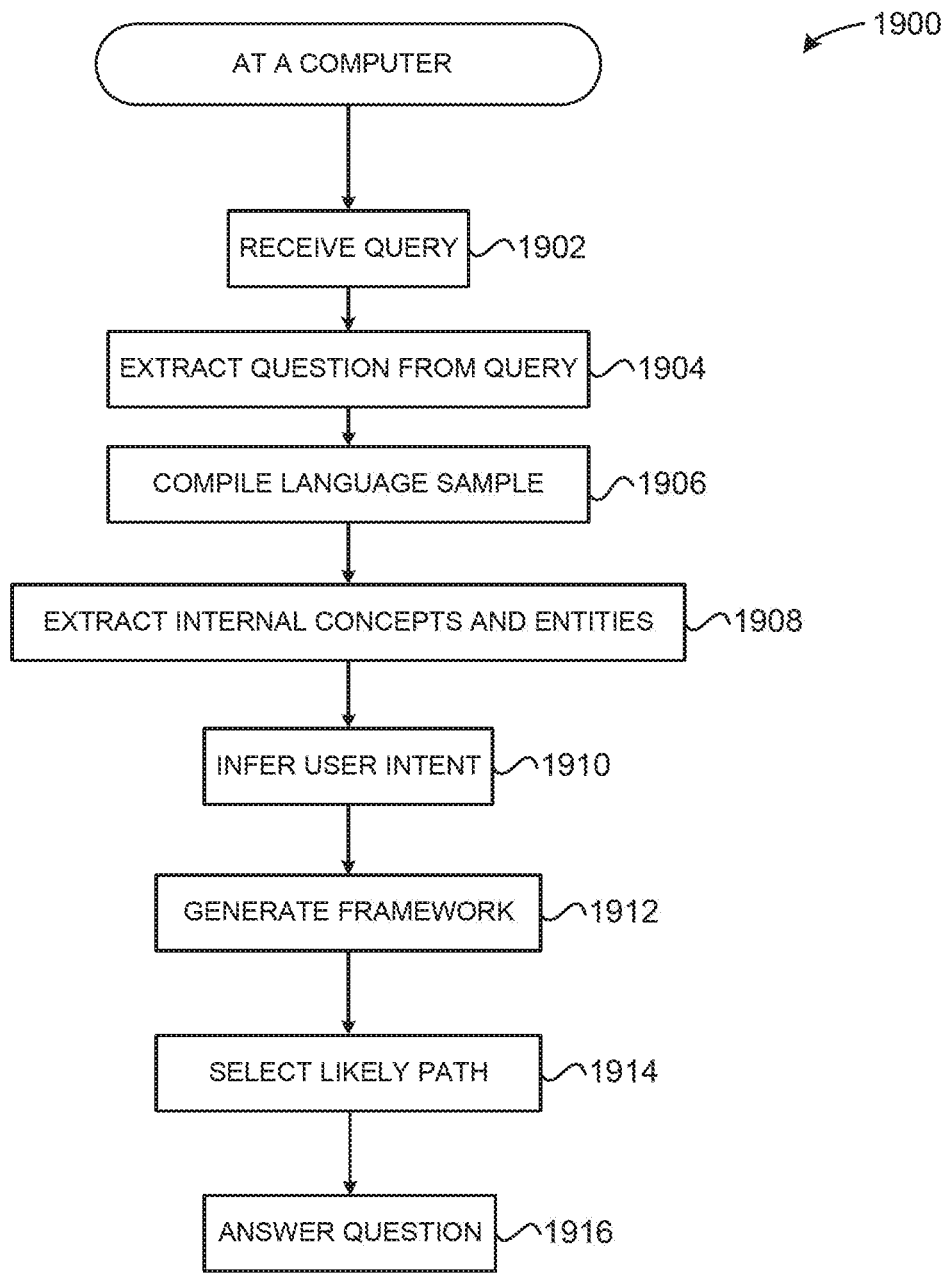
FIG. 19 shows a method, in accordance with various embodiments.

FIG. 19 shows a computer-implemented method 1900 for answering natural language questions posed by a user of a conversational interface of an artificial intelligence system. In some embodiments, the method 1900 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14.

The method 1900 involves receiving a user-generated natural language query at an artificial intelligence-based conversation agent (block 1902). In some embodiments, receiving a user-generated natural language query from a conversational user interface at an artificial intelligence-based conversation cognitive agent (block 1902) is performed by a cognitive agent that is a part of the cognitive intelligence platform and is configured for this purpose. In some embodiments, the artificial intelligence-based conversation agent is the conversation agent 110 of FIG. 1. One example of a user-generated natural language query is "Is a blood sugar of 90 normal?" as shown in line 402 of FIG. 4. In some embodiments, the user interface is on the mobile device 104 of FIG. 1. In some embodiments, receiving a user-generated natural language query from a conversational user interface at an artificial intelligence-based conversation cognitive agent (block 1902) is Step 1 as earlier discussed in the context of "Analyzing Conversational Context As Part of Conversational Analysis".

The method 1900 further includes extracting a question from a user of the conversational user interface from the user-generated natural language query (block 1904). In some embodiments, extracting a question from a user of the conversational user interface from the user-generated natural language query (block 1904) is performed by a critical thinking engine configured for this purpose. In some embodiments, the critical thinking engine is the critical thinking engine 108 of FIG. 1. In some embodiments, extracting a question from a user of the conversational user interface from the user-generated natural language query (block 1904) is accomplished through one or more of Steps 2-6 as earlier discussed in the context of "Analyzing Conversational Context As Part of Conversational Analysis".

The method 1900 includes compiling a language sample (block 1906). In some embodiments, compiling a language sample (block 1906) is performed by a critical thinking engine configured for this purpose. In some embodiments, the critical thinking engine is the critical thinking engine 108 of FIG. 1. The language sample can include items of health-information-related-text derived from a health-related conversation between the artificial intelligence-based conversation cognitive agent and the user. In some embodiments compiling a language sample (block 1906) is accomplished through one or more of Steps 2-6 as earlier discussed in the context of "Analyzing Conversational Context As Part of Conversational Analysis".

The method 1900 involves extracting internal concepts and entities from the language sample (block 1908). In some embodiments, extracting internal concepts and entities from the language sample (block 1908) is performed by a critical thinking engine configured for this purpose. In some embodiments, the critical thinking engine is the critical thinking engine 108 of FIG. 1. The internal concepts can include descriptions of attributes of the entities. In some embodiments, extracting internal concepts and entities from the language sample (block 1908) is accomplished through one or more of Steps 2-6 as earlier discussed in the context of "Analyzing Conversational Context As Part of Conversational Analysis".

The method 1900 involves inferring an intent of the user from the internal concepts and the entities (block 1910). In some embodiments, inferring an intent of the user from the internal concepts and the entities (block 1910) is performed by a critical thinking engine configured for this purpose. In some embodiments, the critical thinking engine is the critical thinking engine 108 of FIG. 1. In some embodiments, inferring an intent of the user from the internal concepts and the entities (block 1910) is accomplished as in Step 2 as earlier discussed in the context of "Analyzing Conversational Context As Part of Conversational Analysis".

The method 1900 includes generating a logical framework 2000 for interpreting of the question (block 1912). In some embodiments, generating a logical framework 2000 for interpreting of the question (block 1912) is performed by a critical thinking engine configured for this purpose. In some embodiments, the critical thinking engine is the critical thinking engine 108 of FIG. 1. In some embodiments, generating a logical framework 2000 for interpreting of the question (block 1912) is accomplished as in Step 5 as earlier discussed in the context of "Analyzing Conversational Context As Part of Conversational Analysis".

Figure 20:
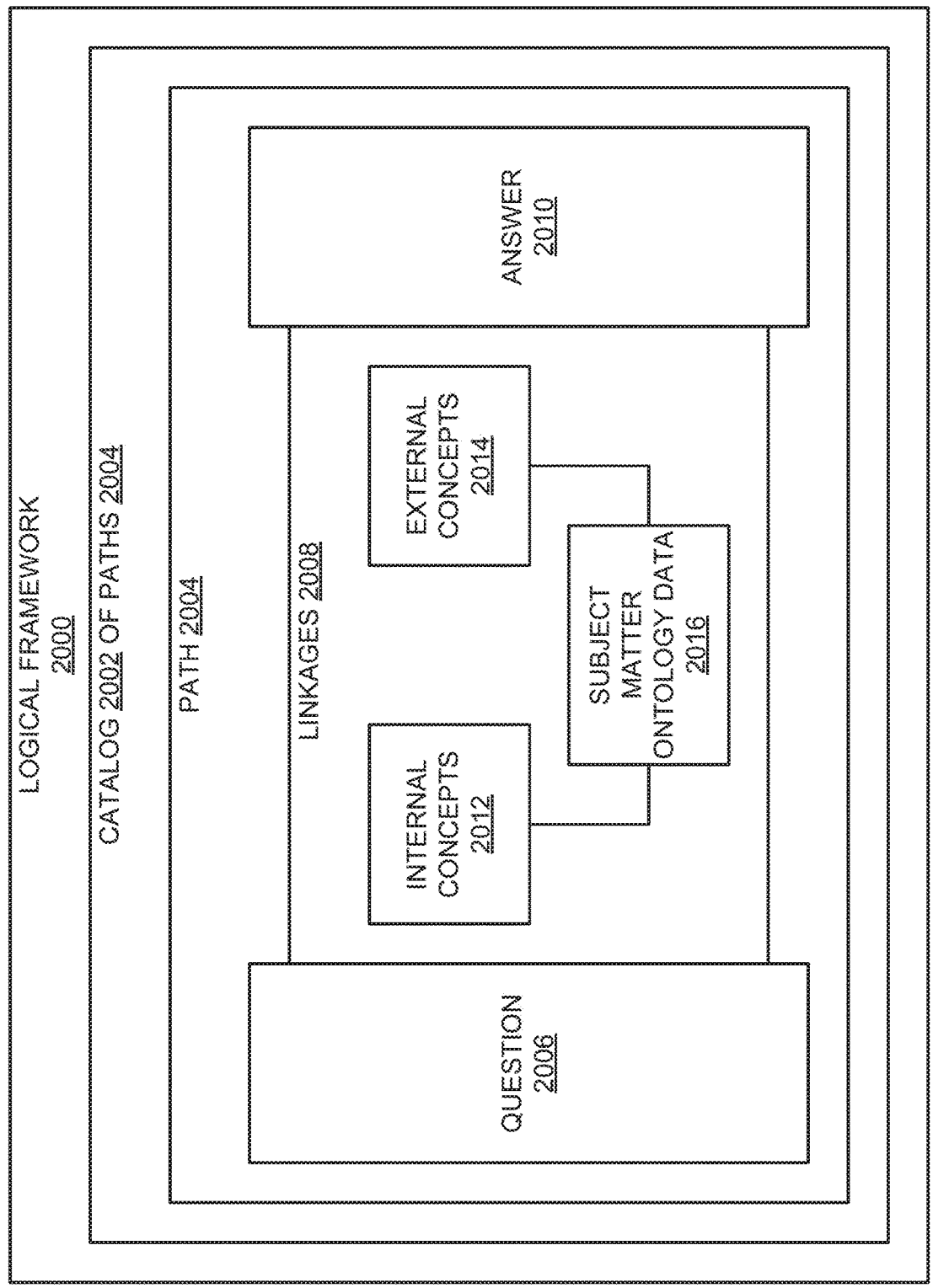
FIG. 20 shows a paradigm logical framework, in accordance with various embodiments.

FIG. 20 shows an example logical framework 2000. The logical framework 2000 includes a catalog 2002 of paths 2004 from the question 2006 to respective answers 2010.

Each of the paths 2004 can include one or more linkages 2008 from the question 2006 to a path-specific answer 2010.

The linkages 2008 can include the internal concepts 2012 and external concepts 2014 derived from a store of subject matter ontology data 2016. In some embodiments, the store of subject matter ontology data 2016 is contained in a knowledge cloud. In some embodiments, the knowledge cloud is the knowledge cloud 102 of FIGS. 1 and 2. In some embodiments, the subject matter ontology data 2016 is the subject matter ontology data 216 of FIG. 2. In some embodiments, the subject matter ontology data 2016 includes the subject matter ontology 300 of FIG. 3.

The method 1900 shown in FIG. 19 further includes selecting a likely path from among the paths 2004 to a likely path-dependent answer based at least in part upon the intent of the user (block 1914). In some embodiments, selecting a likely path from among the paths 2004 to a likely path-dependent answer based at least in part upon the intent of the user (block 1914 is performed by a critical thinking engine configured for this purpose. In some embodiments, the critical thinking engine is the critical thinking engine 108 of FIG. 1. The selection can also be based in part upon the sufficiency of data to complete the linkages 2008. In some embodiments, selection can also be based in part upon the sufficiency of data to complete the linkages 2008 can be performed by a critical thinking engine that is further configured for this purpose. In some embodiments, the critical thinking engine is the critical thinking engine 108 of FIG. 1. The data can include user-specific data. The selection can also be based in part upon treatment sub-intents including tactical constituents related to the intent of the user by the store of subject matter ontology data 2016. In some embodiments, selection based in part upon treatment sub-intents including tactical constituents related to the intent of the user by the store of subject matter ontology data 2016 can be performed by a critical thinking engine further configured for this purpose. In some embodiments, the critical thinking engine is the critical thinking engine 108 of FIG. 1. The selection can further occur after requesting additional data from the user. An example of requesting additional data from the user is shown in FIG. 4 on line 406 "I need some additional information in order to answer this question, was this an in-home glucose test or was it done by a lab or testing service". In some embodiments, the process of selection after requesting additional data from the user can be performed by a critical thinking engine further configured for this purpose. In some embodiments, the critical thinking engine is the critical thinking engine 108 of FIG. 1. In some embodiments, selecting a likely path from among the paths 2004 to a likely path-dependent answer based at least in part upon the intent of the user (block 1914) is accomplished through one or more of Steps 5-6 as earlier discussed in the context of "Analyzing Conversational Context As Part of Conversational Analysis".

The method 1900 involves answering the question by following the likely path to the likely path-dependent answer (block 1916). In some embodiments, answering the question by following the likely path to the likely path-dependent answer (block 1916) is performed by a critical thinking engine configured for this purpose. In some embodiments, the critical thinking engine is the critical thinking engine 108 of FIG. 1. In some embodiments, answering the question by following the likely path to the likely path-dependent answer (block 1916) is accomplished as in Step 7 as earlier discussed in the context of "Analyzing Conversational Context As Part of Conversational Analysis".

The method 1900 can further include relating inference groups of the internal concepts. In some embodiments, relating inference groups of the internal concepts is performed by a critical thinking engine further configured for this purpose. In some embodiments, the critical thinking engine is the critical thinking engine 108 of FIG. 1. Relating inference groups of the internal concepts can be based at least in part on shared entities for which each internal concept of an inference group of internal concepts describes a respective data attribute. In some embodiments, relating inference groups of the internal concepts based at least in part on shared entities for which each internal concept of an inference group of internal concepts describes a respective data attribute can be performed by a critical thinking engine further configured for this purpose. In some embodiments, the critical thinking engine is the critical thinking engine 108 of FIG. 1.

In some embodiments, the method 1900 of FIG. 19 is implemented as a computer program product in a computer-readable medium.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium. The computer readable medium is any data storage device that can store data which can thereafter be read by a computer system. Examples of the computer readable medium include read-only memory, random-access memory, CD-ROMs, DVDs, magnetic tape, hard disk drives, solid-state drives, and optical data storage devices. The computer readable medium can also be distributed over network-coupled computer systems so that the computer readable code is stored and executed in a distributed fashion.

Consistent with the above disclosure, the examples of systems and method enumerated in the following clauses are specifically contemplated and are intended as a non-limiting set of examples.

Clause 1. A cognitive intelligence platform, comprising:
a first system configured to execute a knowledge cloud, the first system comprising:
a first processor; and
a first memory coupled to the first processor, the first memory storing instructions that cause the knowledge cloud to:
receive inputs from medical facilities; and
receive inputs from service providers;
a second system configured to implement a critical thinking engine, the critical thinking engine communicably coupled to the knowledge cloud, the second system comprising:
a second processor; and
a second memory coupled to the second processor, the second memory storing instructions that cause the critical thinking engine to receive inputs from the knowledge cloud; and
a third system configured to implement a cognitive agent, the cognitive agent communicably coupled to the critical thinking engine and the knowledge cloud, the third system comprising:
a third processor; and
a third memory coupled to the third processor, the third memory storing instructions that cause the cognitive agent to:
receive an originating question from a user related to a subject matter;
execute, using the critical thinking engine, a first round of analysis to generate an answer; and
provide the answer to the user including a recommendation associated with the subject matter.

Clause 2. The cognitive intelligence platform of any preceding clause, wherein the second memory stores instructions that further cause the critical thinking engine to:
receive a first information;
receive a second information that contradicts the first information; and
process the first information and second information.

Clause 3. The cognitive intelligence platform of any preceding clause, wherein the second memory stores instructions that further cause the critical thinking engine to:
parse the originating question;
retrieve data from the knowledge cloud; and
perform a causal analysis of the data in view of the originating question, wherein the causal analysis, in part, informs the answer.

Clause 4. The cognitive intelligence platform of any preceding clause, wherein the second memory stores instructions that further cause the critical thinking engine to:
receive the originating question from the cognitive agent;
assess a first chain of logic associated with the originating question;
assess a second chain of logic associated with the originating question; and
provide the answer to the cognitive agent, wherein the answer is associated with the first chain of logic.

Clause 5. The cognitive intelligence platform of any preceding clause, wherein the third memory stores instructions that further cause the cognitive agent to communicate a logical argument that leads to a conclusion, wherein the conclusion, in part, informs the recommendation associated with the subject matter.

Clause 6. The cognitive intelligence platform of any preceding clause, wherein the third memory stores instructions that further cause the cognitive agent to:
render for display, to the user, a chain of logic that leads to the conclusion;
receive, from the user, an adjustment to the chain of logic; and
affect change in the critical thinking engine.

Clause 7. The cognitive intelligence platform of any preceding clause, wherein the third memory stores instructions that further cause the cognitive agent to:
render for display a micro survey;
receive data associated with the micro survey, wherein the data, in part, informs the recommendation associated with the subject matter.

Clause 8. The cognitive intelligence platform of any preceding clause, wherein when the cognitive agent provides the answer to the user, the third memory causes the cognitive agent to integrate data from at least three selected from the group consisting of: a micro survey, a physician's office, common sense knowledge, domain knowledge, an evidence-based medicine guideline, a clinical ontology, and curated medical advice.

Clause 9. A system comprising:
a knowledge cloud;
a critical thinking engine, the critical thinking engine communicably coupled to the knowledge cloud; and
a cognitive agent, the cognitive agent communicably coupled to the critical thinking engine and the knowledge cloud, wherein the cognitive agent is configured to interact with a user using natural language.

Clause 10. The system of any preceding clause, wherein the cognitive agent interacts with the user using at least one selected from the group consisting of: touch-based input, audio input, and typed input.

Clause 11. The system of claim any preceding clause, wherein the critical thinking engine is configured to:
receive a first information;
receive a second information that contradicts the first information; and
process the first information and the second information.

Clause 12. The system of any preceding clause, wherein the cognitive agent is configured to:
- receive an originating question from the user related to a subject matter;
- execute, using the critical thinking engine, a logical reasoning to generate an answer; and
- provide the answer to the user including a recommendation associated with the subject matter.

Clause 13. The system of any preceding clause, wherein the critical thinking engine is configured to:
- parse the originating question;
- retrieve data from the knowledge cloud; and
- perform a causal analysis of the data in view of the originating question, wherein the causal analysis, in part informs the answer.

Clause 14. The system of any preceding clause, wherein the critical thinking engine is configured to:
- receive the originating question from the cognitive agent;
- assess a first chain of logic associated with the originating question;
- assess a second chain of logic associated with the originating question; and
- provide the answer to the cognitive agent, wherein the answer is associated with the first chain of logic.

Clause 15. The system of any preceding clause, wherein the cognitive agent is further configured to render for display a chain of logic that leads to a conclusion, wherein the conclusion, in part, informs the answer.

Clause 16. A computer readable media storing instructions that are executable by a processor to cause a computer to execute operations comprising:
- executing a cognitive intelligence platform that further comprises:
  - a knowledge cloud;
  - a critical thinking engine communicably coupled to the knowledge cloud; and
  - a cognitive agent communicably coupled to the critical thinking engine and the knowledge cloud, wherein the cognitive agent is configured to:
    - receive an originating question from a user related to a subject matter;
    - execute, using the critical thinking engine, a logical reasoning to generate an answer; and
    - provide the answer to the user including a recommendation associated with the subject matter.

Clause 17. The computer-readable media of any preceding clause, wherein the cognitive agent executing within the cognitive intelligence platform is further configured to:
- render for display a micro survey;
- receive data associated with the micro survey, wherein the data, in part, informs the recommendation associated with the subject matter.

Clause 18. The computer-readable media of any preceding clause, wherein the critical thinking engine executing within the cognitive intelligence platform is further configured to:
- receive the originating question from the cognitive agent;
- assess a first chain of logic associated with the originating question to create a first answer;
- assess a second chain of logic associated with the originating question to create a second answer, wherein the first answer contradicts the second answer; and
- provide the first answer to the cognitive agent, wherein the first answer is the answer provided to the user.

Clause 19. The computer-readable media of any preceding clause, wherein the cognitive agent executing within the cognitive intelligence platform is further configured to render for display the first chain of logic to the user.

Clause 20. The computer-readable media of any preceding clause, wherein the cognitive agent executing within the cognitive intelligence platform is further configured to integrate data from at least three selected from the group consisting of: a micro survey, a physician's office, common sense knowledge, domain knowledge, an evidence-based medicine guideline, a clinical ontology, and curated medical advice.

Clause 21. A computer-implemented method for answering a user-generated natural language medical information query based on a diagnostic conversational template, the method comprising:
- receiving a user-generated natural language medical information query at an artificial intelligence-based diagnostic conversation agent from a user interface on a mobile device;
- responsive to content of the user-generated natural language medical information query, selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets;
- compiling user-specific medical fact variable values for one or more respective medical fact variables of the diagnostic fact variable set, wherein the compiling user-specific medical fact variable values for one or more respective medical fact variables of the diagnostic fact variable set further comprises:
  - extracting a first set of user-specific medical fact variable values from a local user medical information profile associated with the user-generated natural language medical information query, and
  - requesting a second set of user-specific medical fact variable values through natural-language questions sent to the user interface on the mobile device; and
- responsive to the user-specific medical fact variable values, generating a medical advice query answer in response to the user-generated natural language medical information query.

Clause 22. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:
- extracting a third set of user-specific medical fact variable values comprising lab result values from the local user medical information profile associated with the user-generated natural language medical information query.

Clause 23. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:
- extracting a fourth set of user-specific medical fact variable values from a remote medical data service profile associated with the local user medical information profile.

Clause 24. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:
  extracting a fifth set of user-specific medical fact variable values derived from demographic characterizations provided by a remote data service analysis of the local user medical information profile.

Clause 25. The computer-implemented method for answering a user-generated natural language medical information query based on a diagnostic conversational template of any preceding clause, wherein the generating the medical advice query answer in response to the user-generated natural language medical information query further comprises providing, in addition to text responsive to a medical question presented in the user-generated natural language medical information query, a treatment action-item recommendation responsive to user-specific medical fact variable values and non-responsive to the medical question presented in the user-generated natural language medical information query.

Clause 26. The computer-implemented method for answering a user-generated natural language medical information query based on a diagnostic conversational template of any preceding clause, wherein the generating the medical advice query answer in response to the user-generated natural language medical information query further comprises providing, in addition to text responsive to a medical question presented in the user-generated natural language medical information query, a medical education media resource responsive to the user-specific medical fact variable values and non-responsive to the medical question presented in the user-generated natural language medical information query.

Clause 27. The computer-implemented method for answering a user-generated natural language medical information query based on a diagnostic conversational template of any preceding clause, wherein selecting a diagnostic fact variable set relevant to generating a medical advice query answer for the user-generated natural language medical information query by classifying the user-generated natural language medical information query into one of a set of domain-directed medical query classifications associated with respective diagnostic fact variable set further comprises classifying the user-generated natural language medical information query into one of a set of domain-directed medical query classifications based on relevance to the local user medical information profile associated with the user-generated natural language medical information query.

Clause 28. A computer program product in a computer-readable medium for answering a user-generated natural language query, the computer program product in a computer-readable medium comprising program instructions which, when executed, cause a processor of a computer to perform:
  receiving a user-generated natural language query at an artificial intelligence-based conversation agent from a user interface;
  responsive to content of the user-generated natural language query, selecting a fact variable set relevant to generating a query answer for the user-generated natural language query by classifying the user-generated natural language query into one of a set of domain-directed query classifications associated with respective fact variable sets;
  compiling user-specific fact variable values for one or more respective fact variables of the fact variable set; and
  responsive to the fact variable values, generating the query answer in response to the user-generated natural language query.

Clause 29. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:
  extracting a first set of user-specific fact variable values from a local user profile associated with the user-generated natural language query; and
  requesting a second set of user-specific fact variable values through a conversational template comprising natural-language questions sent to the user interface on a mobile device.

Clause 30. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:
  extracting a third set of user-specific fact variable values from a remote data service profile associated with the local user profile.

Clause 31. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:
  extracting a fourth set of user-specific fact variable values derived from demographic characterizations provided by a remote data service analysis of the local user profile.

Clause 32. The computer program product in a computer-readable medium for answering a user-generated natural language query of any preceding clause, wherein program instructions which, when executed, cause the processor of the computer to perform the generating the query answer in response to the user-generated natural language query further comprise program instructions which, when executed, cause the processor of the computer to perform providing, in addition to text responsive to a question presented in the user-generated natural language query, an action-item recommendation responsive to the fact variable values and non-responsive to the question presented in the user-generated natural language query.

Clause 33. The computer program product in a computer-readable medium for answering a user-generated natural language query of any preceding clause, wherein the program instructions which, when executed, cause the processor of the computer to perform generating the query answer in response to the user-generated natural language query further comprise program instructions which, when executed, cause the processor of the computer to perform providing, in addition to text responsive to a question presented in the user-generated natural language query, an education media resource responsive to the fact variable values and non-responsive to the question presented in the user-generated natural language query.

Clause 34. The computer program product in a computer-readable medium for answering a user-generated natural language query of any preceding clause, wherein the program instructions which, when executed, cause the processor of the computer to perform selecting a fact variable set relevant to generating a query answer for the user-generated natural language query by classifying the user-generated natural language query into one of a set of domain-directed query classifications associated with respective fact variable sets further comprise program instructions which, when executed, cause the processor of the computer to perform classifying the user-generated natural language query into one of a set of domain-directed query classifications based on relevance to a local user profile associated with the user-generated natural language query.

Clause 35. A cognitive intelligence platform for answering a user-generated natural language query, the cognitive intelligence platform comprising:
  a cognitive agent configured for receiving a user-generated natural language query at an artificial intelligence-based conversation agent from a user interface;
  a critical thinking engine configured for, responsive to content of the user-generated natural language query, selecting a fact variable set relevant to generating a query answer for the user-generated natural language query by classifying the user-generated natural language query into one of a set of domain-directed query classifications associated with respective fact variable sets; and
  a knowledge cloud compiling user-specific fact variable values for one or more respective fact variables of the fact variable set; and
  wherein, responsive to the fact variable values, the cognitive agent is further configured for generating the query answer in response to the user-generated natural language query.

Clause 36. The cognitive intelligence platform of any preceding clause, wherein the knowledge cloud is further configured for:
  extracting a first set of user-specific fact variable values from a local user profile associated with the user-generated natural language query; and
  requesting a second set of user-specific fact variable values through a conversational template comprising natural-language questions sent to the user interface on a mobile device.

Clause 37. The cognitive intelligence platform of any preceding clause, wherein the knowledge cloud is further configured for:
  extracting a third set of user-specific fact variable values from a remote data service profile associated with the local user profile.

Clause 38. The cognitive intelligence platform of any preceding clause, wherein the knowledge cloud is further configured for:
  extracting a fourth set of user-specific fact variable values derived from demographic characterizations provided by a remote data service analysis of the local user profile.

Clause 39. The cognitive intelligence platform of any preceding clause, wherein cognitive agent is further configured for providing, in addition to text responsive to a question presented in the user-generated natural language query, an action-item recommendation responsive to the fact variable values and non-responsive to the question presented in the user-generated natural language query.

Clause 40. The cognitive intelligence platform of any preceding clause, wherein the critical thinking engine is further configured for providing, in addition to text responsive to a question presented in the user-generated natural language query, an education media resource responsive to the fact variable values and non-responsive to the question presented in the user-generated natural language query.

Clause 41. A computer-implemented method for answering a user-generated natural language query, the method comprising:
  receiving a user-generated natural language query at an artificial intelligence-based conversation agent from a user interface;
  responsive to content of the user-generated natural language query, selecting a fact variable set relevant to generating a query answer for the user-generated natural language query by classifying the user-generated natural language query into one of a set of domain-directed query classifications associated with respective fact variable sets;
  compiling user-specific fact variable values for one or more respective fact variables of the fact variable set; and
  responsive to the fact variable values, generating the query answer in response to the user-generated natural language query.

Clause 42. The method of any preceding clause, wherein the compiling user-specific fact variable values for one or more respective fact variables of the fact variable set further comprises:
  extracting a first set of user-specific fact variable values from a local user profile associated with the user-generated natural language query; and
  requesting a second set of user-specific fact variable values through a conversational template comprising natural-language questions sent to the user interface on a mobile device.

Clause 43. The method of any preceding clause, wherein the compiling user-specific fact variable values for one or more respective fact variables of the fact variable set further comprises:
  extracting a third set of user-specific fact variable values from a remote data service profile associated with the local user profile.

Clause 44. The method of any preceding clause, wherein the compiling user-specific fact variable values for one or more respective fact variables of the fact variable set further comprises:
  extracting a fourth set of user-specific fact variable values derived from demographic characterizations provided by a remote data service analysis of the local user profile.

Clause 45. The method of any preceding clause, wherein the generating the query answer in response to the user-generated natural language query further comprises providing, in addition to text responsive to a question presented in the user-generated natural language query, an action-item recommendation responsive to the fact variable values and non-responsive to the question presented in the user-generated natural language query.

Clause 46. The method of any preceding clause, wherein the generating the query answer in response to the user-generated natural language query further comprises providing, in addition to text responsive to a question presented in the user-generated natural language query, an education media resource responsive to the fact variable values and non-responsive to the question presented in the user-generated natural language query.

Clause 47. The method of any preceding clause, wherein selecting a fact variable set relevant to generating a query answer for the user-generated natural language query by classifying the user-generated natural language query into one of a set of domain-directed query classifications associated with respective fact variable sets further comprises classifying the user-generated natural language query into one of a set of domain-directed query classifications based on relevance to a local user profile associated with the user-generated natural language query.

Clause 48. A computer-implemented method for answering natural language medical information questions posed by a user of a medical conversational interface of a cognitive artificial intelligence system, the method comprising:
  receiving from a medical conversational user interface a user-generated natural language medical information query at an artificial intelligence-based medical conversation cognitive agent;
  extracting from the user-generated natural language medical information query a medical question from a user of the medical conversational user interface;
  compiling a medical conversation language sample, wherein the medical conversation language sample comprises items of health-information-related-text derived from a health-related conversation between the artificial intelligence-based medical conversation cognitive agent and the user;
  extracting from the medical conversation language sample internal medical concepts and medical data entities present within the medical conversation language sample, wherein the internal medical concepts comprise descriptions of medical attributes of the medical data entities;
  inferring a therapeutic intent of the user from the internal medical concepts and the medical data entities;
  generating a therapeutic paradigm logical framework for interpreting of the medical question, wherein
    the therapeutic paradigm logical framework comprises a catalog of medical logical progression paths from the medical question to respective therapeutic answers,
    each of the medical logical progression paths comprises one or more medical logical linkages from the medical question to a therapeutic path-specific answer, and
    the medical logical linkages comprise the internal medical concepts and external therapeutic paradigm concepts derived from a store of medical subject matter ontology data;
  selecting a likely medical information path from among the medical logical progression paths to a likely path-dependent medical information answer based upon the therapeutic intent of the user; and
  answering the medical question by following the likely medical information path to the likely path-dependent medical information answer.

Clause 49. The computer-implemented method for answering natural language medical information questions posed by a user of a medical conversational interface of a cognitive artificial intelligence system of any of any of the preceding clauses, further comprising relating medical inference groups of the internal medical concepts.

Clause 50. The computer-implemented method for answering natural language medical information questions posed by a user of a medical conversational interface of a cognitive artificial intelligence system of any of any of the preceding clauses, wherein the relating medical inference groups of the internal medical concepts further comprises relating groups of the internal medical concepts based at least in part on shared medical data entities for which each internal medical concept of a medical inference group of internal medical concepts describes a respective medical data attribute.

Clause 51. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon the therapeutic intent of the user and in part upon sufficiency of medical diagnostic data to complete the medical logical linkages.

Clause 52. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer after requesting additional medical diagnostic data from the user.

Clause 53. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon treatment sub-intents comprising tactical constituents related to the therapeutic intent of the user by the store of medical subject matter ontology data.

Clause 54. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon the therapeutic intent of the user and in part upon sufficiency of medical diagnostic data to complete the medical logical linkages, wherein the medical diagnostic data to complete the medical logical linkages includes user-specific medical diagnostic data.

Clause 55. A cognitive intelligence platform for answering natural language questions posed by a user of a conversational interface of an artificial intelligence system, the cognitive intelligence platform comprising:
- a cognitive agent configured for receiving from a user interface a user-generated natural language query, wherein the cognitive agent is an artificial intelligence-based conversation agent;
- a knowledge cloud containing a store of subject matter ontology data;
- a critical thinking engine configured for:
  - extracting from the user-generated natural language query a question from a user of the user interface,
  - compiling a language sample, wherein the language sample comprises items of text derived from a conversation between the artificial intelligence-based conversation agent and the user,
  - extracting from the language sample internal concepts and entities present within the language sample, wherein the internal concepts comprise descriptions of attributes of the entities,
  - inferring an intent of the user from the internal concepts and the entities,
  - generating a logical framework for interpreting of the question, wherein
    - the logical framework comprises a catalog of paths from the question to respective answers,
    - each of the paths comprises one or more linkages from the question to a path-specific answer, and
    - the linkages comprise the internal concepts and external concepts derived from the store of subject matter ontology data,
  - selecting a likely path from among the paths to a likely path-dependent answer based upon the intent, and
  - answering the question by following the likely path to the likely path-dependent answer.

Clause 56. The cognitive intelligence platform for answering natural language questions posed by a user of a conversational interface of an artificial intelligence system of any of the preceding clauses, wherein the critical thinking engine is further configured for relating groups of the internal concepts.

Clause 57. The cognitive intelligence platform for answering natural language questions posed by a user of a conversational interface of an artificial intelligence system of any of the preceding clauses, wherein the critical thinking engine is further configured for relating groups of the internal concepts by relating groups of the internal concepts based at least in part on shared entities for which each internal concept of a group of internal concepts describes a respective attribute.

Clause 58. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer based in part upon the intent and in part upon sufficiency of data to complete the linkages.

Clause 59. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer after requesting additional data from the user.

Clause 60. The cognitive intelligence platform for answering natural language questions posed by a user of a conversational interface of an artificial intelligence system of 8, wherein the critical thinking engine is further configured for selecting a likely path from among the paths to a likely path-dependent answer based upon the intent further comprises selecting a likely path from among the paths to a likely path-dependent answer based in part upon sub-intents comprising tactical constituents related to the intent by the store of subject matter ontology data.

Clause 61. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer based in part upon the intent and in part upon sufficiency of data to complete the linkages, wherein the data to complete the linkages includes user-specific data.

Clause 62. A computer program product in a computer-readable medium for answering natural language questions posed by a user of a conversational interface of an artificial intelligence system, the computer program product in a computer-readable medium comprising instructions, which, when executed, cause a processor of a computer to perform:
- receiving from a user interface a user-generated natural language query at an artificial intelligence-based conversation agent;
- extracting from the user-generated natural language query a question from a user of the user interface;
- compiling a language sample, wherein the language sample comprises items of text derived from a conversation between the artificial intelligence-based conversation agent and the user;
- extracting from the language sample internal concepts and entities present within the language sample, wherein the internal concepts comprise descriptions of attributes of the entities;
- inferring an intent of the user from the internal concepts and the entities;
- generating a logical framework for interpreting of the question, wherein
  - the logical framework comprises a catalog of paths from the question to respective answers,
  - each of the paths comprises one or more linkages from the question to a path-specific answer, and
  - the linkages comprise the internal concepts and external concepts derived from a store of subject matter ontology data;
- selecting a likely path from among the paths to a likely path-dependent answer based upon the intent; and
- answering the question by following the likely path to the likely path-dependent answer.

Clause 63. The computer program product in a computer-readable medium for answering natural language questions posed by a user of a conversational interface of an artificial intelligence system of any of the preceding clauses, further comprising instructions, which, when executed, cause the processor of the computer to perform relating groups of the internal concepts.

Clause 64. The computer program product in a computer-readable medium for answering natural language questions posed by a user of a conversational interface of an artificial intelligence system of any of the preceding clauses, wherein the instructions, which, when executed, cause the processor of the computer to perform relating groups of the internal concepts further comprise instructions, which, when executed, cause the processor of the computer to perform relating groups of the internal concepts based at least in part on shared entities for which each internal concept of a group of internal concepts describes a respective attribute.

Clause 65. The computer program product in a computer-readable medium for answering natural language questions posed by a user of a conversational interface of an artificial intelligence system of any of the preceding clauses, wherein the instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer based in part upon the intent and in part upon sufficiency of data to complete the linkages.

Clause 66. The computer program product in a computer-readable medium for answering natural language questions posed by a user of a conversational interface of an artificial intelligence system of any of the preceding clauses, wherein instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer after requesting additional data from the user.

Clause 67. The computer program product in a computer-readable medium for answering natural language questions posed by a user of a conversational interface of an artificial intelligence system of any of the preceding clauses, wherein the instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer based in part upon sub-intents comprising tactical constituents related to the intent by the store of subject matter ontology data.

Clause 68. A method for answering natural language questions posed by a user of a conversational interface of an artificial intelligence system, the method comprising:
receiving from a user interface a user-generated natural language query at an artificial intelligence-based conversation agent;
extracting from the user-generated natural language query a question from a user of the user interface;
compiling a language sample, wherein the language sample comprises items of text derived from a conversation between the artificial intelligence-based conversation agent and the user;
extracting from the language sample internal concepts and entities present within the language sample, wherein the internal concepts comprise descriptions of attributes of the entities;
inferring an intent of the user from the internal concepts and the entities;
generating a logical framework for interpreting of the question, wherein
the logical framework comprises a catalog of paths from the question to respective answers,
each of the paths comprises one or more linkages from the question to a path-specific answer, and
the linkages comprise the internal concepts and external concepts derived from a store of subject matter ontology data;
selecting a likely path from among the paths to a likely path-dependent answer based upon the intent; and
answering the question by following the likely path to the likely path-dependent answer.

Clause 69. The method for answering natural language questions posed by a user of a conversational interface of an artificial intelligence system of any of the preceding clauses, further comprising relating groups of the internal concepts.

Clause 70. The method for answering natural language questions posed by a user of a conversational interface of an artificial intelligence system of any of the preceding clauses, wherein the relating groups of the internal concepts further comprises relating groups of the internal concepts based at least in part on shared entities for which each internal concept of a group of internal concepts describes a respective attribute.

Clause 71. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon the intent and in part upon sufficiency of data to complete the linkages.

Clause 72. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer after requesting additional data from the user.

Clause 73. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon sub-intents comprising tactical constituents related to the intent by the store of subject matter ontology data.

Clause 74. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon the intent and in part upon sufficiency of data to complete the linkages, wherein the data to complete the linkages includes user-specific data.

The foregoing description, for purposes of explanation, used specific nomenclature to provide a thorough understanding of the described embodiments. However, it should be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A computer-implemented method for answering natural language medical information questions posed by a user of a medical conversational interface of a cognitive artificial intelligence system, the method comprising:
   receiving from a medical conversational user interface a user-generated natural language medical information query at an artificial intelligence-based medical conversation cognitive agent;
   extracting from the user-generated natural language medical information query a medical question from a user of the medical conversational user interface;
   compiling a medical conversation language sample, wherein the medical conversation language sample comprises items of health-information-related-text derived from a health-related conversation between the artificial intelligence-based medical conversation cognitive agent and the user;
   extracting from the medical conversation language sample internal medical concepts and medical data entities present within the medical conversation language sample, wherein the internal medical concepts comprise descriptions of medical attributes of the medical data entities;
   inferring a therapeutic intent of the user from the internal medical concepts and the medical data entities;
   generating a therapeutic paradigm logical framework for interpreting of the medical question, wherein
   the therapeutic paradigm logical framework comprises a catalog of medical logical progression paths from the medical question to respective therapeutic answers,
   each of the medical logical progression paths comprises one or more medical logical linkages from the medical question to a therapeutic path-specific answer, and
   the medical logical linkages comprise the internal medical concepts and external therapeutic paradigm concepts derived from a store of medical subject matter ontology data;
   selecting a likely medical information path from among the medical logical progression paths to a likely path-dependent medical information answer based upon the therapeutic intent of the user; and
   answering the medical question by following the likely medical information path to the likely path-dependent medical information answer.

2. The computer-implemented method for answering natural language medical information questions posed by a user of a medical conversational interface of a cognitive artificial intelligence system of claim 1, further comprising relating medical inference groups of the internal medical concepts.

3. The computer-implemented method for answering natural language medical information questions posed by a user of a medical conversational interface of a cognitive artificial intelligence system of claim 2, wherein the relating medical inference groups of the internal medical concepts further comprises relating groups of the internal medical concepts based at least in part on shared medical data entities for which each internal medical concept of a medical inference group of internal medical concepts describes a respective medical data attribute.

4. The computer-implemented method for answering natural language medical information questions posed by a user of a medical conversational interface of a cognitive artificial intelligence system of claim 1, wherein selecting a likely medical information path from among the medical logical progression paths to a likely path-dependent medical information answer based upon the intent further comprises selecting a likely medical information path from among the medical logical progression paths to a likely path-dependent medical information answer based in part upon the therapeutic intent of the user and in part upon sufficiency of medical diagnostic data to complete the medical logical linkages.

5. The computer-implemented method for answering natural language medical information questions posed by a user of a medical conversational interface of a cognitive artificial intelligence system of claim 1, wherein selecting a likely medical information path from among the medical logical progression paths to a likely path-dependent medical information answer based upon the intent further comprises selecting a likely medical information path from among the medical logical progression paths to a likely path-dependent medical information answer after requesting additional medical diagnostic data from the user.

6. The computer-implemented method for answering natural language medical information questions posed by a user of a medical conversational interface of a cognitive artificial intelligence system of claim 1, wherein selecting a likely medical information path from among the medical logical progression paths to a likely path-dependent medical information answer based upon the intent further comprises selecting a likely medical information path from among the medical logical progression paths to a likely path-dependent medical information answer based in part upon treatment sub-intents comprising tactical constituents related to the therapeutic intent of the user by the store of medical subject matter ontology data.

7. The computer-implemented method for answering natural language medical information questions posed by a user of a medical conversational interface of a cognitive artificial intelligence system of claim 1, wherein selecting a likely medical information path from among the medical logical progression paths to a likely path-dependent medical information answer based upon the intent further comprises selecting a likely medical information path from among the medical logical progression paths to a likely path-dependent medical information answer based in part upon the therapeutic intent of the user and in part upon sufficiency of medical diagnostic data to complete the medical logical linkages, wherein the medical diagnostic data to complete the medical logical linkages includes user-specific medical diagnostic data.

8. A cognitive intelligence platform for answering natural language questions posed by a user of a conversational interface of an artificial intelligence system, the cognitive intelligence platform comprising:

a cognitive agent configured for receiving from a user interface a user-generated natural language query, wherein the cognitive agent is an artificial intelligence-based conversation agent;

a knowledge cloud containing a store of subject matter ontology data;

a critical thinking engine configured for:
- extracting from the user-generated natural language query a question from a user of the user interface,
- compiling a language sample, wherein the language sample comprises items of text derived from a conversation between the artificial intelligence-based conversation agent and the user,
- extracting from the language sample internal concepts and entities present within the language sample, wherein the internal concepts comprise descriptions of attributes of the entities,
- inferring an intent of the user from the internal concepts and the entities,
- generating a logical framework for interpreting of the question, wherein
  - the logical framework comprises a catalog of paths from the question to respective answers,
  - each of the paths comprises one or more linkages from the question to a path-specific answer, and
  - the linkages comprise the internal concepts and external concepts derived from the store of subject matter ontology data,
- selecting a likely path from among the paths to a likely path-dependent answer based upon the intent, and
- answering the question by following the likely path to the likely path-dependent answer.

9. The cognitive intelligence platform for answering natural language questions posed by a user of a conversational interface of an artificial intelligence system of claim 8, wherein the critical thinking engine is further configured for relating groups of the internal concepts.

10. The cognitive intelligence platform for answering natural language questions posed by a user of a conversational interface of an artificial intelligence system of claim 8, wherein the critical thinking engine is further configured for relating groups of the internal concepts by relating groups of the internal concepts based at least in part on shared entities for which each internal concept of a group of internal concepts describes a respective attribute.

11. The cognitive intelligence platform for answering natural language questions posed by a user of a conversational interface of an artificial intelligence system of claim 8, wherein the critical thinking engine is further configured for selecting a likely path from among the paths to a likely path-dependent answer based upon the intent further comprises selecting a likely path from among the paths to a likely path-dependent answer based in part upon the intent and in part upon sufficiency of data to complete the linkages.

12. The cognitive intelligence platform for answering natural language questions posed by a user of a conversational interface of an artificial intelligence system of claim 8, wherein the critical thinking engine is further configured for selecting a likely path from among the paths to a likely path-dependent answer based upon the intent further comprises selecting a likely path from among the paths to a likely path-dependent answer after requesting additional data from the user.

13. The cognitive intelligence platform for answering natural language questions posed by a user of a conversational interface of an artificial intelligence system of claim 8, wherein the critical thinking engine is further configured for selecting a likely path from among the paths to a likely path-dependent answer based upon the intent further comprises selecting a likely path from among the paths to a likely path-dependent answer based in part upon sub-intents comprising tactical constituents related to the intent by the store of subject matter ontology data.

14. The cognitive intelligence platform for answering natural language questions posed by a user of a conversational interface of an artificial intelligence system of claim 8, wherein the critical thinking engine is further configured for selecting a likely path from among the paths to a likely path-dependent answer based upon the intent further comprises selecting a likely path from among the paths to a likely path-dependent answer based in part upon the intent and in part upon sufficiency of data to complete the linkages, wherein the data to complete the linkages includes user-specific data.

15. A computer program product in a non-transitory computer-readable medium for answering natural language questions posed by a user of a conversational interface of an artificial intelligence system, the computer program product in a computer-readable medium comprising instructions, which, when executed, cause a processor of a computer to perform:
- receiving from a user interface a user-generated natural language query at an artificial intelligence-based conversation agent;
- extracting from the user-generated natural language query a question from a user of the user interface;
- compiling a language sample, wherein the language sample comprises items of text derived from a conversation between the artificial intelligence-based conversation agent and the user;
- extracting from the language sample internal concepts and entities present within the language sample, wherein the internal concepts comprise descriptions of attributes of the entities;
- inferring an intent of the user from the internal concepts and the entities;
- generating a logical framework for interpreting of the question, wherein
  - the logical framework comprises a catalog of paths from the question to respective answers,
  - each of the paths comprises one or more linkages from the question to a path-specific answer, and
  - the linkages comprise the internal concepts and external concepts derived from a store of subject matter ontology data;
- selecting a likely path from among the paths to a likely path-dependent answer based upon the intent; and
- answering the question by following the likely path to the likely path-dependent answer.

16. The computer program product in a non-transitory computer-readable medium for answering natural language questions posed by a user of a conversational interface of an artificial intelligence system of claim 15, further comprising instructions, which, when executed, cause the processor of the computer to perform relating groups of the internal concepts.

17. The computer program product in a non-transitory computer-readable medium for answering natural language questions posed by a user of a conversational interface of an artificial intelligence system of claim 16, wherein the instructions, which, when executed, cause the processor of the computer to perform relating groups of the internal concepts further comprise instructions, which, when executed, cause the processor of the computer to perform relating groups of the internal concepts based at least in part on shared entities for which each internal concept of a group of internal concepts describes a respective attribute.

18. The computer program product in a non-transitory computer-readable medium for answering natural language questions posed by a user of a conversational interface of an artificial intelligence system of claim 15, wherein the instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer based in part upon the intent and in part upon sufficiency of data to complete the linkages.

19. The computer program product in a non-transitory computer-readable medium for answering natural language questions posed by a user of a conversational interface of an artificial intelligence system of claim 15, wherein instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer after requesting additional data from the user.

20. The computer program product in a non-transitory computer-readable medium for answering natural language questions posed by a user of a conversational interface of an artificial intelligence system of claim 15, wherein the instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer based in part upon sub-intents comprising tactical constituents related to the intent by the store of subject matter ontology data.

21. A method for answering natural language questions posed by a user of a conversational interface of an artificial intelligence system, the method comprising:
receiving from a user interface a user-generated natural language query at an artificial intelligence-based conversation agent;
extracting from the user-generated natural language query a question from a user of the user interface;
compiling a language sample, wherein the language sample comprises items of text derived from a conversation between the artificial intelligence-based conversation agent and the user;
extracting from the language sample internal concepts and entities present within the language sample, wherein the internal concepts comprise descriptions of attributes of the entities;
inferring an intent of the user from the internal concepts and the entities;
generating a logical framework for interpreting of the question, wherein
the logical framework comprises a catalog of paths from the question to respective answers,
each of the paths comprises one or more linkages from the question to a path-specific answer, and
the linkages comprise the internal concepts and external concepts derived from a store of subject matter ontology data;
selecting a likely path from among the paths to a likely path-dependent answer based upon the intent; and
answering the question by following the likely path to the likely path-dependent answer.

22. The method for answering natural language questions posed by a user of a conversational interface of an artificial intelligence system of claim 21, further comprising relating groups of the internal concepts.

23. The method for answering natural language questions posed by a user of a conversational interface of an artificial intelligence system of claim 22, wherein the relating groups of the internal concepts further comprises relating groups of the internal concepts based at least in part on shared entities for which each internal concept of a group of internal concepts describes a respective attribute.

24. The method for answering natural language questions posed by a user of a conversational interface of an artificial intelligence system of claim 21, wherein selecting a likely path from among the paths to a likely path-dependent answer based upon the intent further comprises selecting a likely path from among the paths to a likely path-dependent answer based in part upon the intent and in part upon sufficiency of data to complete the linkages.

25. The method for answering natural language questions posed by a user of a conversational interface of an artificial intelligence system of claim 21, wherein selecting a likely path from among the paths to a likely path-dependent answer based upon the intent further comprises selecting a likely path from among the paths to a likely path-dependent answer after requesting additional data from the user.

26. The method for answering natural language questions posed by a user of a conversational interface of an artificial intelligence system of claim 21, wherein selecting a likely path from among the paths to a likely path-dependent answer based upon the intent further comprises selecting a likely path from among the paths to a likely path-dependent answer based in part upon sub-intents comprising tactical constituents related to the intent by the store of subject matter ontology data.

27. The method for answering natural language questions posed by a user of a conversational interface of an artificial intelligence system of claim 21, wherein selecting a likely path from among the paths to a likely path-dependent answer based upon the intent further comprises selecting a likely path from among the paths to a likely path-dependent answer based in part upon the intent and in part upon sufficiency of data to complete the linkages, wherein the data to complete the linkages includes user-specific data.

* * * * *